(12) United States Patent
Borochowitz

(10) Patent No.: US 9,295,239 B2
(45) Date of Patent: Mar. 29, 2016

(54) MO-1 CONDITIONAL KNOCK-OUT NON-HUMAN ANIMAL AND USES THEREOF

(75) Inventor: Zvi Borochowitz, Haifa (IL)

(73) Assignee: Medical Research & Development Fund for Health Services Bnai Zion Medical Center, THE STATE OF ISRAEL, Haifa (IL)

( * ) Notice: Subject to any disclaimer, the term of this patent is extended or adjusted under 35 U.S.C. 154(b) by 0 days.

(21) Appl. No.: 13/508,399

(22) PCT Filed: Nov. 8, 2010

(86) PCT No.: PCT/IL2010/000920
§ 371 (c)(1),
(2), (4) Date: May 7, 2012

(87) PCT Pub. No.: WO2011/055366
PCT Pub. Date: May 12, 2011

(65) Prior Publication Data
US 2012/0227118 A1 Sep. 6, 2012

(30) Foreign Application Priority Data
Nov. 8, 2009 (IL) .......................................... 201999

(51) Int. Cl.
*A01K 67/00* (2006.01)
*C12N 15/00* (2006.01)
*A01K 67/027* (2006.01)
*C12N 15/85* (2006.01)

(52) U.S. Cl.
CPC ........ *A01K 67/0276* (2013.01); *C12N 15/8509* (2013.01); *A01K 2217/075* (2013.01); *A01K 2217/206* (2013.01); *A01K 2227/105* (2013.01); *A01K 2267/0306* (2013.01); *A01K 2267/0362* (2013.01)

(58) Field of Classification Search
None
See application file for complete search history.

(56) References Cited

FOREIGN PATENT DOCUMENTS

WO   WO 2008082125 A1 * 7/2008
WO   WO 2008/130668   10/2008

OTHER PUBLICATIONS

Bockamp et al. Conditional Transgenic Mouse Models: from the Basics to Genome-Wide Sets of Knockouts and Current Studies of Tissue Regeneration. Future Medicine, 2008. 3(2): 217-235.*
Powel. Obesity Drugs and Their Targets: Correlation of Mouse knockout Phenotypes with Drug Effects In Vivo. Obesity Reviews, 2007. 7(1): 89-108.*
Beale. PCK1 and PCK2 as Candidate Diabetes and Obesity Genes. Cell BioChem and Biophysics, 2007. 48: 89-105.*
Müller, at al. Ten Years of Gene Targeting: Targeted Mouse Mutants, From Vector Design to Phenotype Analysis. Mechanisms of Development, 1999: 82:3-21.*
International Search Report and the Written Opinion Dated Feb. 25, 2011 From the International Searching Authority Re. Application No. PCT/IL2010/000920.
Clément "Genetics of Human Obesity", Comptes Rendues—Biologies, XP005575146, 329(8): 608-622, Aug. 1, 2006.
Kos "Cre/LoxP System for Generating Tissue-Specific Knockout Mouse Models", Nutrition Reviews, XP002621771, 62(6/Pt.1): 243-246, Jun. 2004. p. 243, Fig. 1.
Ramirez "Morbid Obesity-1 (MO-1): Linkage, Identification and Characterization of a Novel Obesity Gene", Dissertation Submitted to the Graduate Faculty of the Mount Sinai Graduate School of Biological Sciences in Partial Fullfillment of the Degree of Doctor of Philosophy, Mount Sinai School of Medicine of New York University, XP009144410, p. 1-122, Jan. 1, 2009.
International Preliminary Report on Patentability Dated May 18, 2012 From the International Bureau of WIPO Re. Application No. PCT/IL2010/000920.
Office Action Dated Jul. 11, 2013 From the Israel Patent Office Re. Application No. 201999 and Its Translation Into English.

* cited by examiner

*Primary Examiner* — Christopher M Babic
*Assistant Examiner* — Kimberly A Aron

(57) ABSTRACT

A conditional knock-out non-human animal is disclosed. Wherein some cells of the non-human animal but not all the cells comprise a disrupted MO-1 nucleic acid sequence, wherein the disruption results in an inability of the non-human animal to produce detectable levels of the MO-1 protein, as assayed by Southern blot analysis.

20 Claims, 64 Drawing Sheets
(39 of 64 Drawing Sheet(s) Filed in Color)

SEQ ID NO:1
MO-1 Polypeptide Sequence

Presumed initial Methionine shown in parentheses (M)YMGMCTAKCCTRFQPPAILLYESEIKQKIRQRIMPVRNPSKFSCCTRAAEQLKMPRHKSYLEQVSLR
QLEKLFSFLRGTLSQSLAETMEQTQRETTIDPEEDLNKLDDKELAKRKSIMDELFRNQKKQDPNFVYDIEV
EFTQDDQLQSCCMDTESADEF

FIG. 2A

SEQ ID NO:2
MO-1 cDNA Sequence

Presumed Start and Stop shown in bold, underlined text

```
CGCTCGCCGG GACCTGGAAT CCCTGTACGC CGAGGTGGGA GCCGGTGGAC    50
CGGTCCCCCA GCCGGCCCCC ACCTCCGCTT CCCGGTGTTT GAGGGTTCGG   100
GCCTCCCGCC GGGGAGTTCA CCCCTCGGGC TCGTCAGTAG GGCTGTGGCT   150
GTCGCCTCTT CCTGCAGCGC CAGGCTCCGC CCGGTCTCAC AGTCGGCTTA   200
GGGGCTTTGC GTGCACTGCG GTTGGGTGGA AAAACCCACT CCTGGTTGTT   250
TAGACGTTGG CCTGCAGACG ATGTCATTTC TGTATTCCTC TAAGGCAGGA   300
AGTCATTATG CAACTTACAC ATATTCATCA GATTCCTCT GACTTACCCG    350
GACATGTACG TGGAATGAT GTGCACTGCC AAGAAATGTG GGATTAGGTT    400
TCAGCCTCCA GCTATTATCT TAATCTATGA GAGTGAAATC AAGGGGAAAA   450
TTCGCCAGCG CATTATGCCA GTTCGAAACT TTTCAAAGTT TTCAGATTGC   500
ACCAGAGCTG CTGAACAATT AAGAATAAT CCGCGACACA AGAGTTACCT    550
AGAACAAGTA TCCCTGAGGC AGCTAGAGAA GCTATTCAGT TTTTTACGAG   600
GTTACTTGTC GGGGCAGAGT CTGGCAGAAA CAATGGAACA AATTCAACGG   650
GAAACAACCA TTGATCCTGA GGAAGACCTG AACAAACTAG ATGACAAGGA   700
GCTTGCCAAA AGAAGAGCA TCATGGATGA ACTTTTTGAG AAAAATCAGA    750
AGAAGAAGGA TGATCCAAAT TTTGTTTATG ACATTGAGGT TGAATTTCCA   800
CAGGACGATC AACTGCAGTC CTGTGGCTGG GACACAGAGT CAGCTGATGA   850
GTTCTGATAC CAAACACTCA AAACATGCAT TGGGCTAGCA GAATATCCAT   900
GTTATTACC AGACTGGTTC TGGAAGAAGC TGTAAAGAAT ACTAAATATG    950
TTGGGTTATA GGGGATTGAC CATGTTACTT TTCAAAACCA GGACATTTAA  1000
AGCATCTACT ATGTAGGTGC ATGAGGAGTA TGGGAAAAAC AGAATAAAGG  1050
AATCTGCCTT TAAGGAGCTT ACAATCATGC CGGGTGCGGT GGCTCACGCC  1100
TGTAATCCCA GCACTTTGGG AGGCTGAGGC GGGTGGATCA CCTAAGGTCA  1150
GGAGTTCGAG ACCAGCCTAG CCAACATGGT GAAACCTCGC CTCTACTAAA  1200
AATACAAAAA TTAGCCAGGC GTGGTGGCGG GTGCCTGTAA TCCCGGCTAC  1250
TCAGGAGGCT GAGGCAGGAG ATTCGCTTGA ACCTGGGAGG CTGAaGTTGC  1300
AGTGAGCCGA GATCGCGCCA TTGTACTCCA GCCTGGGCGA TGAGCAAAAC  1350
TCCATCTCaa aaaaaaaaaa aaaaaaaaaa aaaaaaaaaa aaaaaaaaaa  1400
```

FIG. 2B

Introns and flanking sequences shown in lower case text, exons are in upper case text actaaacggatctaaatgataccaaggatgacagaaacatcctcatttta
cagatggagaaacttgtagggtttgtgctttcctcccatcaaaccttacc
ctttattgtaattattcccgcacttgcccgtctcagtagtacaagcagtt
tgccaactactacttgcacgaacaactagcagtttgccacggagtcctac
attcagtttggggattctcaggcctcacagggcgctaaggccttgcctgg
cccttggtgatcagaagcttcgtgcagctcaagagcatcccaagacgct
tgacggctgacttccttctcagaactttagtaacagggcggccagtcca
gctgggaaccgcagggcccgagcccgactctcccggagacccgggatcc
gccgcagagcaaagcgcacggagggaaggagggcacacggctctagtgt
ctgacctcctccggctcgccctactgatctaggtcccgcgccgggtcccc
acatcccgcaacccgccgagaggcccgggagccgggaccgctcccacgc
tctggcccccaagcccgcccccttaccggcgtcagagcgcgcggcgg
tgaaggccgcggcgggcccgcgcgtgagcccggtcgccgccccgaggagc
agccaggcggccgcccgaaccgccgccacccgagccgccaggacgccgga
agccggacgccgagaggggcgcgcgcgggccaggtgcggacgcaggaagg
ggcctggccgccgcagctcctaccgcgcgcgctgccccagatttatcggct
gggaccgagtgctgggtgcgcgcgcctagcgcccgcggttcccagctgcc
tgcagccccggcccccaagggttcccgcgcgggcgtggggcggtcgtcccc
gcccagctgttccttgctccgcccacccgggggcgggcgaggagctgcgc
acgcgcggggacgcgcgcccggcctgtcgctgtggaaaccgctaggccag
CCCTCGCCGGGACCTGGAATCCCTGTACGCCGAGGTGGGAGCCGGTGGAC
CGGTCCCCCAGCCGGCCCCCACCTCCGCTTCCCGGTGTTTGAGGGTTCGG
GCCTCCCGCCGGGGAGTTCACCCCTCGGGCTCGTCAGTAGGGCTGTGGCT
GTCGCCTCTTCCTGCAGCGCCAGGCTCCGCCCGGTCTCACAGTCGGCTTA
GGGGCTTTGCGTGCACTGCGGTTGGGTGGAAAAACCCACTCCTGGTTGTT
TAGACGTTGGCCTGCAGACGATGTCATTTCTGTATTCCTCTAAGGtaag
aaagccagccttgcactagtggagacgtgagtagggagagaatcgtctac
tctttggggacattcgtacccttaggtgctgtggggcttcctaacaagat
tgtgggcagttactgatctctggggagaggagtattcgtgtccaggaaga
ataattggataaacgtgccgtccttcttcctaaacagagtggaatctgta
agcaggccaagagagcatccaggcggcttggagtggaatagagggctcta
gagcgggtgtctcaaagaggaaacagagtgtatgtcaaaacatactatcc
aaaactgaaaatagccgggcaggtggctcacgcctatagccccagcactt
tgggcgaatcacctgaggtcaggagttcgagaccagcctggccaagatgg
cgaaaccccgtctctactgaaaatacaaagattagctgggcatggtggta
ggcacctgtaattccagctactcgggaggctgaggcacgagaatcgcttg
aacccaggaggcggaggttgcagcgaggggagatcacgccactgcactgc
agcctaggcgacagagggagactctgtttcaaaagaaaaaaaaaactga
aaatggtagtataagcatgttttcttaagaaatggagagagaattttgga
agatatgccttttaaaattcagtctggctccctatgaagaggagtagggc
caaggacgatagtttgttgttataagcctcatagaattatttatattcc
aaatacaaacattactttagcaaaaattaaagttaaattttaaaaagagt
ctagtaaaaaaaaactacattatttgagtaccaactgcatacatctttg
acgagtacagccattgcttcagtgtgtggagtttatatgtgcccgtagg
ttgtagtttactaacatcaaattttagttaggtgaattgggaatagtatt

FIG. 2C

```
cgttaaaaaaaaaaaaaagcaagaaaagagaaggaaaagaaggagaaat
ggtgtgagctcattgcatcagattagaggtagagcacagtaattttttaa
agtagtttttttttttttttttttttttttaagaataggcgtatcatgc
tttggagaggctgttgtgcagtggcaccatctcaactcactgcagcccca
aactcctgggttcaggcgattctcccaccttggcctttggtgtggctggg
actacaggtgcatgctgccatgcctggccaattttaaattttttgtaga
gacatgcatggtctcgctgtgttgcccaggctggtctcaaactcctggcc
tcaaggtatctcctctccttggcctcccaaagtgttgggattacaggcct
gagccaccacacctgcctccatctttttgagatggagtcttgctcttgtc
acccatgctggagtgcagtggtaccatctcagctcactgcaacctccgcc
tcccaggttcaagtgattctcctgccttggcctctcgagtagctgggatt
acaggcacctgccactatgtccagctaattttgtatttttagtacagac
gtggttttcaccatgttggccaggctggtctcgaactcctgacctcaaat
gatctgcccaccttgacctcccaaagtgctggctggggtgagccactgtg
cctgggcttatatgtgattaattttctaagagtaaaaattctcatgccca
acaataagtggtgaataatatgattatagtacatccataaaataaaacat
ttagcagtcatataaaatgttacattgtagtaaaacatttgatgacaaaa
taataatatatgttgttaaatttgaacgtcaggaaatagcttgtatgata
aggtatgtatgaaacatactataaactatatgcctagaaaaaagactgga
cacaatcaagggtgattattttctataggtttcccctctcctttgcccc
agtattctacaatgacgtgtataatcactgctaagtatttaataaaaagt
atgttcctaatagtgattctccagcagaactgagttcacgaagatatcat
caccctatgccactttacctcaatgtttcttgacatttacaaatctttct
gggaatgtcacagtcacatcaaaagcagtgcttagggttaagtgtattct
ttgggcactgagggtggggaaaggaagagagaatagtaagtattcatcta
caaatagctgtttcttgtagctagaaaattatcatatagtgagacacaca
ggccaaaataaaagccctgcagacattactgactattgtatatgaagaag
ctgagatatgtgatgtatatgatgtagctgcagacgttactgacgtgtat
atgaagaagctgattctgcagcaggtctgcttttgatcaggcttctaga
ctgtaaatgctttcaaaaatgtacagggaccatcatgttaattcatagca
ttaaacaatgtatggaatgcccactacgttccaggtattatgctgagata
ttgtggtggaaaatgaatatgcccccacccctcatggagcatattgacta
gaagggaagatagatgattaaataaataatgacaaaaaactctagtaaaa
taattgggaaagtacaaaggagacagttctggattggtgaacctctcagg
acaaaatgattaaggttaaaaaacttacctatcatagtaccttgatacc
gaggatgctcgatatgccctttcttaattgataaatagtaaagaccctat
aggtcagctattgggctgacttaggggttcatattcgatcttcagtaaga
gtgcagtacactaagaggttcaaactggattgcatccccagattcacata
tgaacaagtctatatccttgaaaaaccagatcttagggatccaacaggt
tgaaactaacccagggccaagctgaactttcagggcagttctcaaaataa
ctgagctttgtggtcgttcccgcgcacataccccacaattggaatgatac
agagaggatcagcatggccccctgcgcaaggatgacacacaaattcatgaa
gcagtccgtatttaattttaaaaaaaatgagtttcacaggctgagcgtg
tgtggccagagccggactagaaccagatcttctggggcaaagggcgagg
ggaatgaatgacatttatccaacacctagttgttttttccctttagCAGG
AAGTCATTATCAACTTACACATATTCATCAGATTTCCTCTGACTTACCCC
GGACATGTACATGGGAATGATGTGCACTGCCAAGAAATGTGGGATTAGGT
```

FIG. 2C cont.

```
TTCAGCCTCCAGCTATTATCTTAATCTATGAGAGTGAAATCAAGGGGAAA
ATTCGCCAGCGCATTATGCCAGTTCGAAACTTTTCAAAGTTTTCAGgtac
ctcatgtcttatcttgcctcctgtcttaaatattctctaaatacaggttc
acatcatgactctgtcaggGactggatgtgtgacactggatgaattactt
actctcagtgagcttcagtttcctaatctataaaagggaattgtagtgtt
ttttccaatctgataattaataatcctttgggattgctgcctaggtta
aatgatatagcattattcaataatattaattcccttctctcattccaaat
gttttattgtagtcttaatatttattaataccactactgctatcta
aaagctataatatcacttttcttctcagacatattctccagttgaaagtg
tttaatatctctacaaagtgattttaagttaaagaagtcaaaactgtat
ctgtccttctcccaccacactgaaagctcaatataaaggaatggttctac
aaagtaattcattccaatcaagccatttagctacttgactataatggaga
taatatttcagggttcagagttttgttctgttttggctgttgcagtag
tttatggcgtatatgatgtacgtggtacgtatgtggtatatagttttctt
ctctctcccagATTGCACCAGAGCTGCTGAACAATTAAAGAATAATCCGC
GACACAAGAGTTACCTAGAACAAGTATCCCTGAGGCAGCTAGAGAAGCTA
TTCAGTTTTTTACGAGGTTACTTGTCGGGGCAGAGTCTGGCAGAAACAAT
GGAACAAATTCAACGGGAAACAACCATTGATCCTGAGGAAGACCTGAACA
AACTAGATGACAAGGAGCTTGCCAAAAGAAAGAGCATCATGGATGAACTT
TTTGAGAAAATCAGAAGAAGAAGGATGATCCAAATTTTGTTTATGACAT
TGAGGTTGAATTTCCACAGGACGATCAACTGCAGTCCTGTGGCTGGGACA
CAGAGTCAGCTGATGAGTTCTGATACCAAACACTCAAAACATGCATTGGG
CTAGCAGAATATCCATGTTTATTACCAGACTGGTTCTGGAAGAAGCTGTA
AAGAATACTAAATATGTTGGGTTATAGGGATTGACCATGTTACTTTTCA
AAACCAGGACATTTAAAGCATCTACTATGTAGGTGCATGAGGAGTATGGG
AAAAACAGAATAAAGGAATCTGCCTTTAAGGAGCTTACAATCATGCCGGG
TGCGGTGGCTCACGCCTGTAATCCCAGCACTTTGGGAGGCTGAGGCGGGT
GGATCACCTAAGGTCAGGAGTTCGAGACCAGCCTAGCCAACATGGTGAAA
CCTCGCCTCTACTAAAAATACAAAAATTAGCCAGGCGTGGTGGCGGGTGC
CTGTAATCCCGGCTACTCAGGAGGCTGAGGCAGGAGATTCGCTTGAACCT
GGGAGGCTGAGGTTGCAGTGAGCCGAGATCGCGCCATTGTACTCCAGCCT
GGGCGATGAGCAAAACTCCATCTCAAaaaaaaaaaaaaaaaaaagcttac
aatctgactggaagatgtcaaaacctgtgaaaagctaattagcagtatta
agcaacacaaacattagtgccaaatgcatgataaaggctaaagaaggcca
gagcatatattactgtagagtagaatagtaagggaagactttgtcctta
gtaaagagataggaggtggcctggccctgaaatagtagtgtttaggtag
atgcttgtgtaggattcctgataagagcaactgaaagaaggagaggga
agtagtaaagggacaagaaacaattttttttgaggaaccataagcaaa
ttatagtttgacaagacaagattgggggacatatatggttaccagggaat
tacctctatgtgttatatctttatattatttatctctggaaaagagtac
cctgcaaaattccctacagctgcaagcagatgtcacttgatggacagagg
gggaattctgcccctccggtatcgggaaatacatactaaagacattgcga
aacgctgaacctcttcccataaataaaaggtttgtttgtaaaatgggaaa
tccacccataataaatgaacaataggcactgccagtttaggcctgttcat
gaatggatctgcaagacagcatcttcgtttaacaacattatctgtgattt
gatacatttatccttattacaatattgtttagttggtagaaattctatgt
tttctacaaggaaattgatgtttattaaataaaactgaaaataattactc
```

FIG. 2C cont.

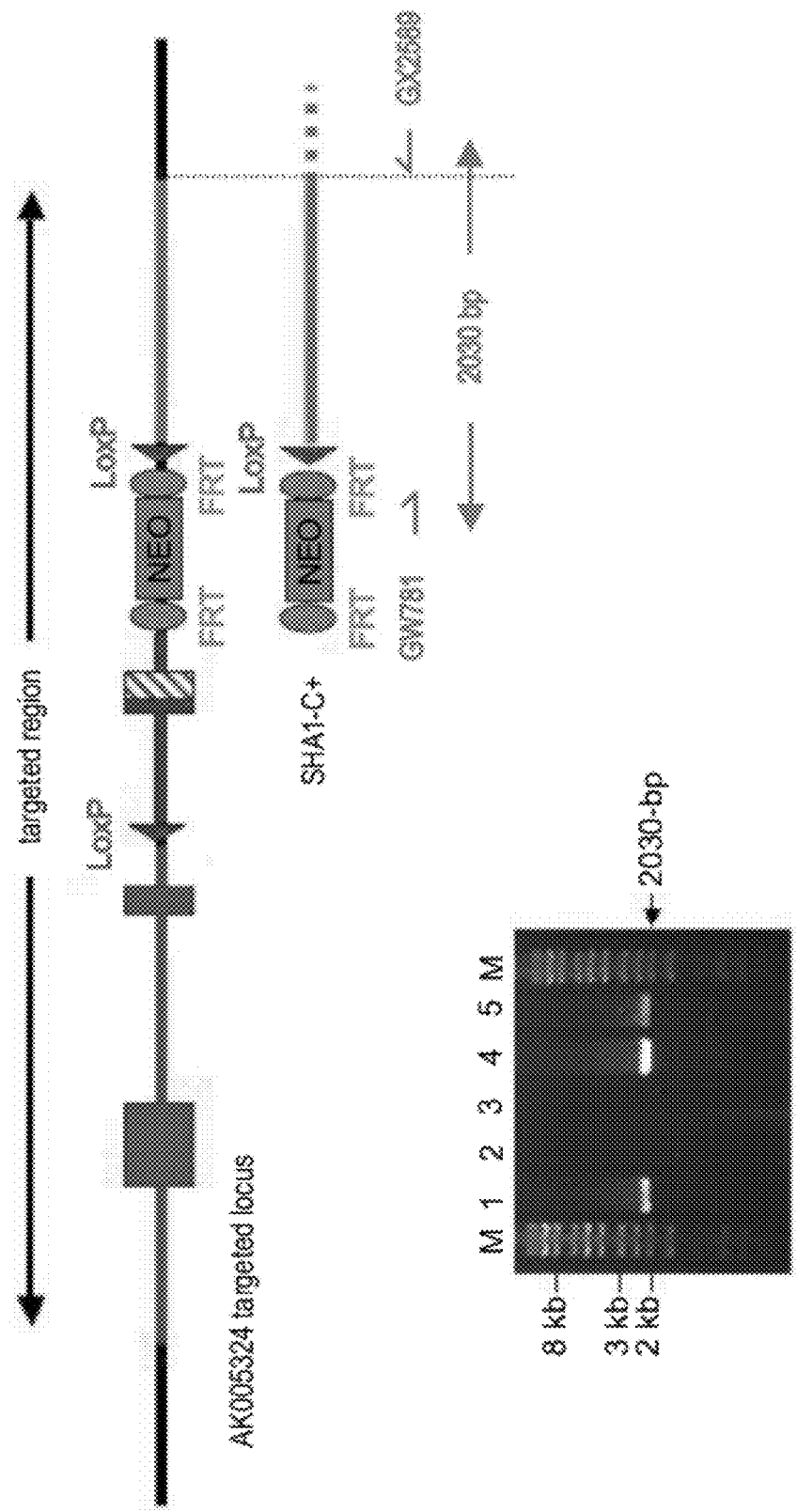

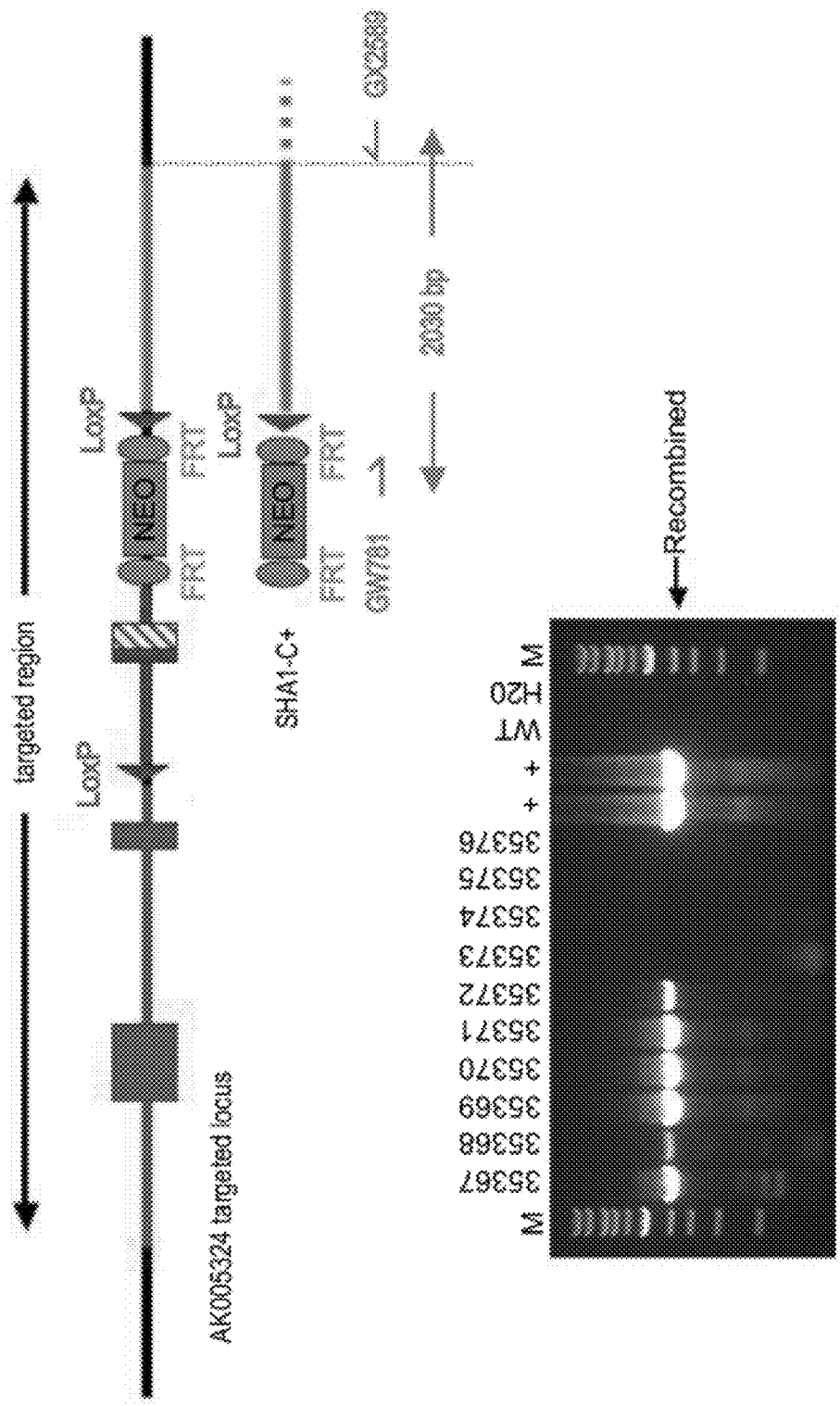

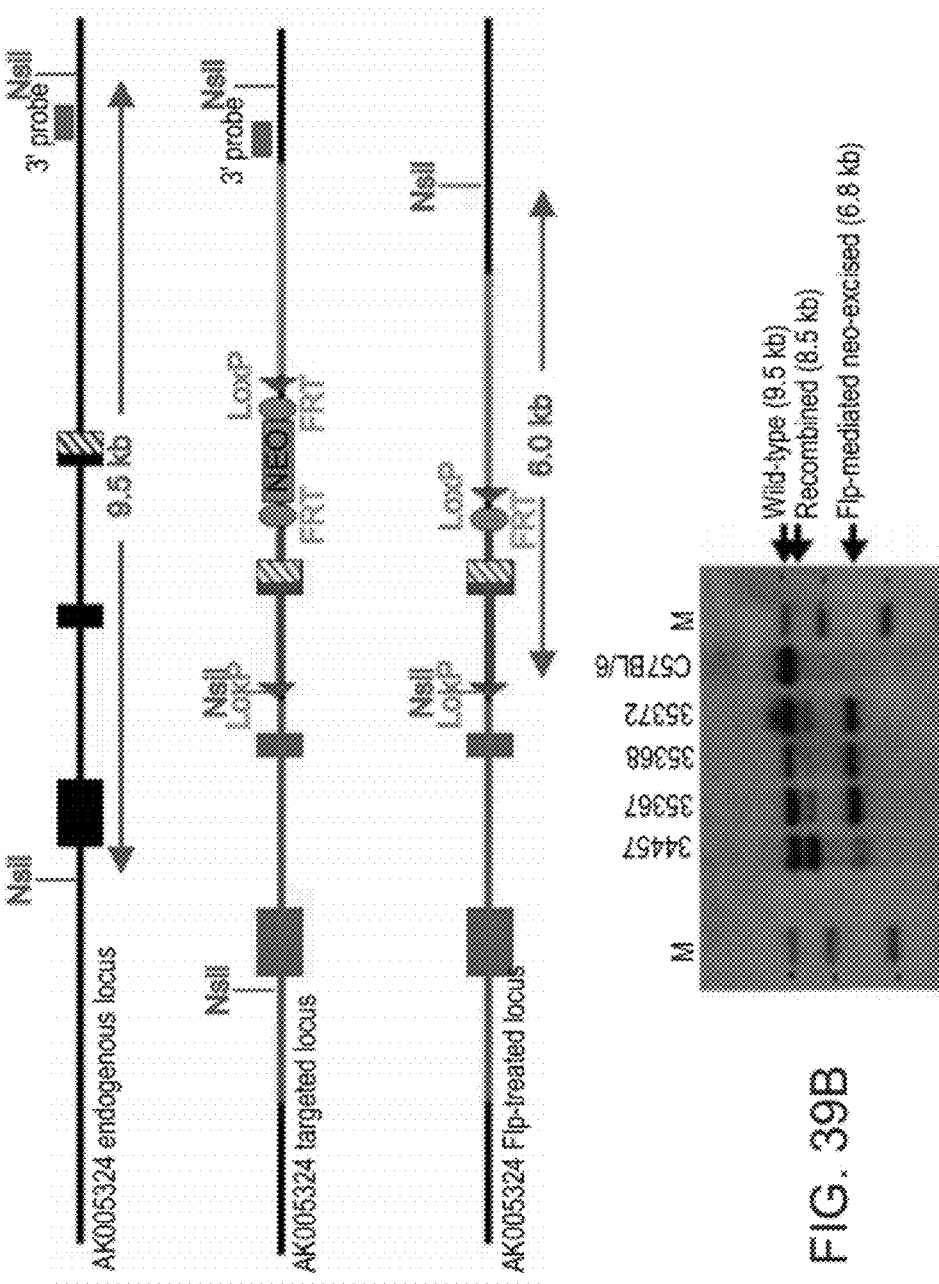

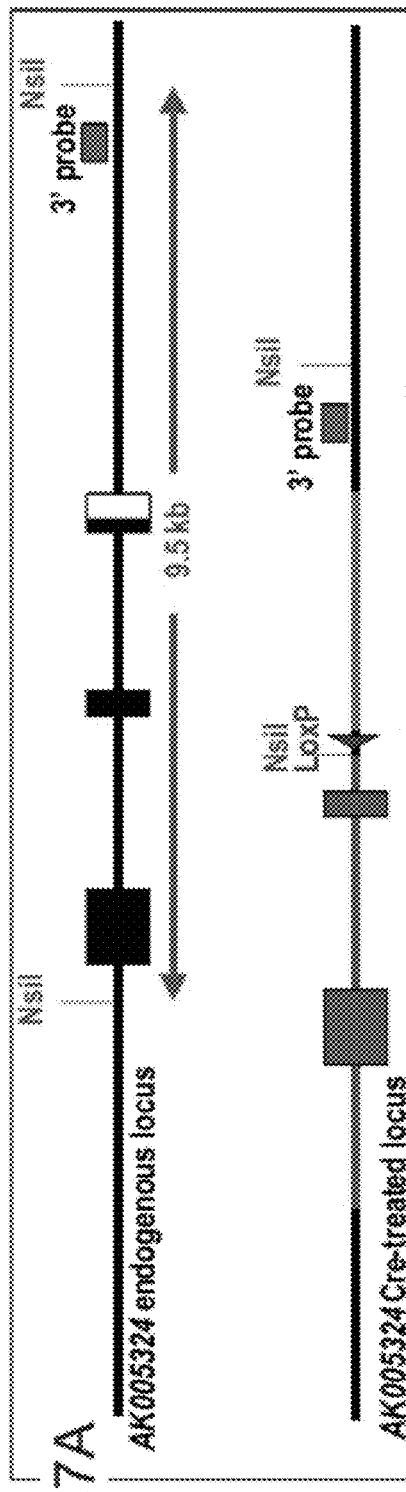
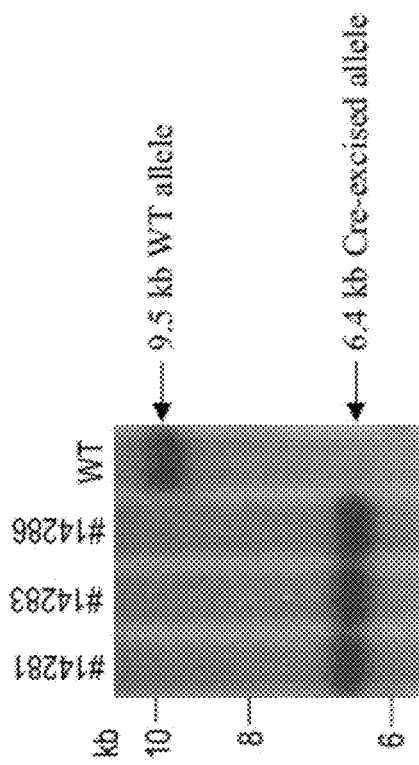
FIG. 47A
FIG. 47B

MRI: abdominal section of body fat content

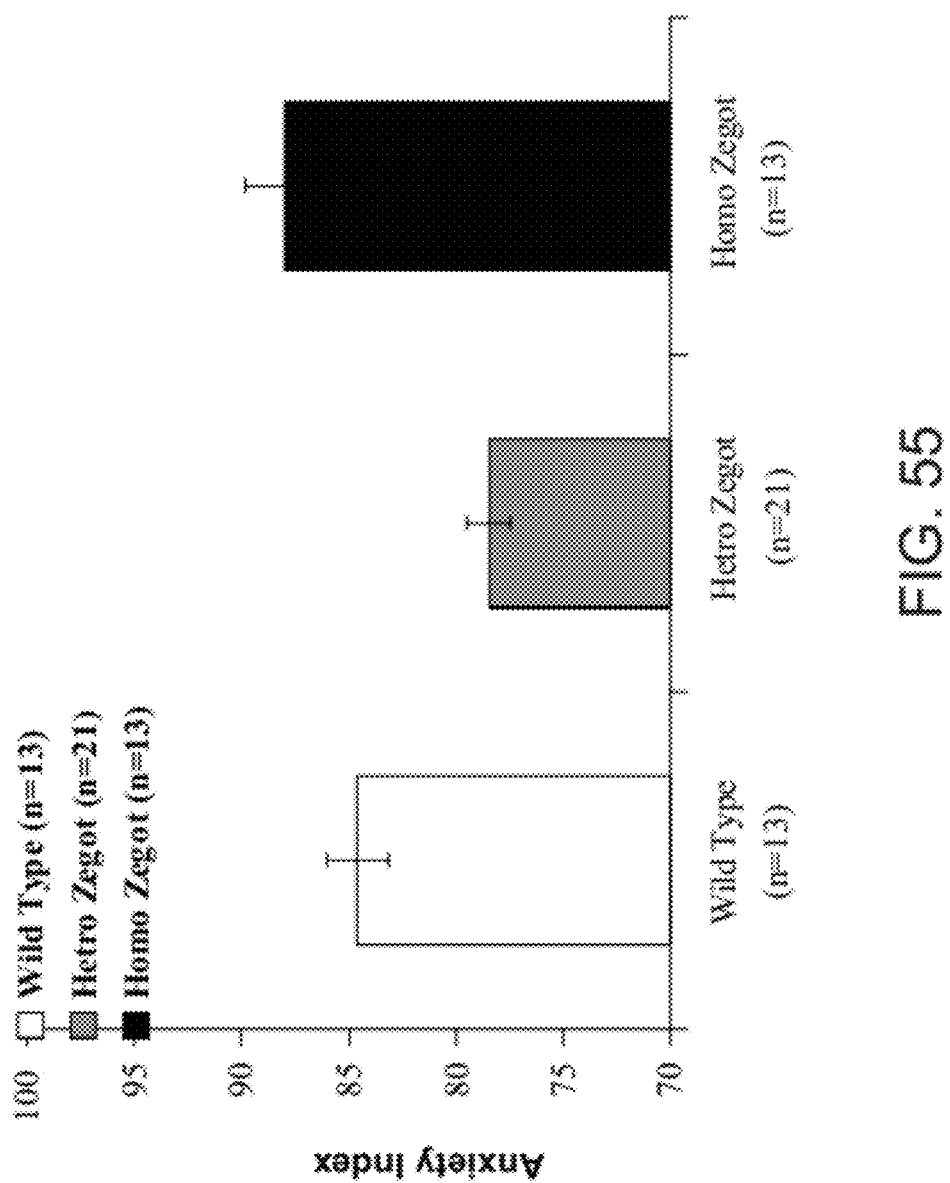

```
SEQUENCE LISTING

<160> NUMBER OF SEQ ID NOS: 45

<210> SEQ ID NO 1
<211> LENGTH: 167
<212> TYPE: PRT
<213> ORGANISM: Homo sapiens

<400> SEQUENCE: 1

Met Tyr Met Gly Met Met Cys Thr Ala Lys Lys Cys Gly Ile Arg Phe
1               5                   10                  15

Gln Pro Pro Ala Ile Ile Leu Ile Tyr Glu Ser Glu Ile Lys Gly Lys
                20                  25                  30

Ile Arg Gln Arg Ile Met Pro Val Arg Asn Phe Ser Lys Phe Ser Asp
            35                  40                  45

Cys Thr Arg Ala Ala Glu Gln Leu Lys Asn Asn Pro Arg His Lys Ser
        50                  55                  60

Tyr Leu Glu Gln Val Ser Leu Arg Gln Leu Glu Lys Leu Phe Ser Phe
65                  70                  75                  80

Leu Arg Gly Tyr Leu Ser Gly Gln Ser Leu Ala Glu Thr Met Glu Gln
                85                  90                  95

Ile Gln Arg Glu Thr Thr Ile Asp Pro Glu Glu Asp Leu Asn Lys Leu
            100                 105                 110

Asp Asp Lys Glu Leu Ala Lys Arg Lys Ser Ile Met Asp Glu Leu Phe
        115                 120                 125

Glu Lys Asn Gln Lys Lys Lys Asp Asp Pro Asn Phe Val Tyr Asp Ile
    130                 135                 140

Glu Val Glu Phe Pro Gln Asp Asp Gln Leu Gln Ser Cys Gly Trp Asp
145                 150                 155                 160

Thr Glu Ser Ala Asp Glu Phe
                165

<210> SEQ ID NO 2
<211> LENGTH: 1400
<212> TYPE: DNA
<213> ORGANISM: Homo sapiens

<400> SEQUENCE: 2
cgctcgccgg gacctggaat ccctgtacgc cgaggtggga gccggtggac cggtccccca        60
gccggccccc acctccgctt cccggtgttt gagggttcgg gcctcccgcc ggggagttca       120
```

```
cccctcgggc tcgtcagtag ggctgtggct gtcgcctctt cctgcagcgc caggctccgc    180
ccggtctcac agtcggctta ggggcttttgc gtgcactgcg gttgggtgga aaaacccact    240
cctggttgtt tagacgttgg cctgcagacg atgtcatttc tgtattcctc taaggcagga    300
agtcattatg caacttacac atattcatca gatttcctct gacttacccg acatgtacg     360 tgggaatgat gtgcactgcc aagaaatgtg ggattaggtt tcagcctcca gctattatct    420
taatctatga gagtgaaatc aaggggaaaa ttcgccagcg cattatgcca gttcgaaact    480
tttcaaagtt ttcagattgc accagagctg ctgaacaatt aaagaataat ccgcgacaca    540
agagttacct agaacaagta tccctgaggc agctagagaa gctattcagt tttttacgag    600
gttacttgtc ggggcagagt ctggcagaaa caatggaaca aattcaacgg gaaacaacca    660
ttgatcctga ggaagacctg aacaaactag atgacaagga gcttgccaaa agaaagagca    720
tcatggatga acttttttgag aaaaatcaga agaagaagga tgatccaaat tttgtttatg    780
acattgaggt tgaatttcca caggacgatc aactgcagtc ctgtggctgg acacagagt     840 cagctgatga gttctgatac caaacactca aaacatgcat tgggctagca gaatatccat    900
gtttattacc agactggttc tggaagaagc tgtaaagaat actaaatatg ttgggttata    960
ggggattgac catgttactt ttcaaaacca ggacatttaa agcatctact atgtaggtgc   1020
atgaggagta tgggaaaaac agaataaagg aatctgcctt taaggagctt acaatcatgc   1080
cgggtgcggt ggctcacgcc tgtaatccca gcactttggg aggctgaggc gggtggatca   1140
cctaaggtca ggagttcgag accagcctag ccaacatggt gaaacctcgc ctctactaaa   1200
aatacaaaaa ttagccaggc gtggtggcgg gtgcctgtaa tcccggctac tcaggaggct   1260
gaggcaggag attcgcttga acctgggagg ctgaagttgc agtgagccga gatcgcgcca   1320
ttgtactcca gcctgggcga tgagcaaaac tccatctcaa aaaaaaaaa aaaaaaaaa    1380 aaaaaaaaa aaaaaaaaa                                                1400
```

<210> SEQ ID NO 3
<211> LENGTH: 6950
<212> TYPE: DNA
<213> ORGANISM: Homo sapiens

<400> SEQUENCE: 3

```
actaaacgga tctaaatgat accaaggatg acagaaacat cctcatttta cagatggaga     60
aacttgtagg gtttgtgctt tcctcccatc aaaccttacc ctttattgta attattcccg    120
cacttgcccg tctcagtagt acaagcagtt tgccaactac tacttgcacg aacaactagc    180
agtttgccac ggagtcctac attcagtttg gggattctca ggcctcacag ggcgctaagg    240
ccttgcctgg ccccttggtg atcagaagct tcgtgcagct caagagcatc caagacgct     300 tgacggctga ctttccttct cagaacttta gtaacagggc ggccagtcca gcctgggaac    360
cgcagggccc gagcccgact ctcccggaga cccgggatcc gccgcagagc aaagcgcacg    420
ggagggaagg agggcacacg gctctagtgt ctgacctcct ccggctcgcc ctactgatct    480
aggtcccgcg ccgggtcccc acatcccgc aacccgccga gaggcccggg agccgggacc     540
gctcccacgc tctggccccc caagcccgc cccccttacc ggcgtcagag cgcgcggcgg    600
tgaaggccgc ggcggggcccg cgcgtgagcc cggtcgccgc cccgaggagc agccaggcgg    660
ccgcccgaac cgccgccacc cgagccgcca ggacgccgga agccgacgc ccgagagggg     720 cgcgcggggc caggtgcgga cgcaggaagg ggcctggccg cccgcagctc ctaccgcgcg    780
```

```
ctgccccaga tttatcggct gggaccgagt gctgggtgcg cgcgcctagc gcccgcggtt    840
cccagctgcc tgcagccccg gcccccaagg gttcccgcgc ggcgtggggc ggtcgtcccc    900
gcccagctgt tccttgctcc gcccacccgg gggcgggcga ggagctgcgc acgcgcgggg    960
acgcgcgccc ggcctgtcgc tgtggaaacc gctaggccag cgctcgccgg gacctggaat   1020
ccctgtacgc cgaggtggga gccggtggac cggtccccca gccggccccc acctccgctt   1080
cccggtgttt gagggttcgg gcctcccgcc ggggagttca cccctcgggc tcgtcagtag   1140
ggctgtggct gtcgcctctt cctgcagcgc caggctccgc ccggtctcac agtcggctta   1200
ggggctttgc gtgcactgcg gttgggtgga aaacccact cctggttgtt tagacgttgg    1260
cctgcagacg atgtcatttc tgtattcctc taagggtaag aaagccagcc ttgcactagt   1320
ggagacgtga gtaggagag aatcgtctac tctttgggga cattcgtacc cttaggtgct    1380
gtggggcttc ctaacaagat tgtgggcagt tactgatctc tggggagagg agtattcgtg   1440
tccaggaaga ataattggat aaacgtgccg tccttcttcc taaacagagt ggaatctgta   1500
agcaggccaa gagagcatcc aggcggcttg gagtggaata gagggctcta gagcgggtgt   1560
ctcaaagagg aaacagagtg tatgtcaaaa catactatcc aaaactgaaa atagccgggc   1620
aggtggctca cgcctatagc cccagcactt gggcgaatc acctgaggtc aggagttcga    1680
gaccagcctg gccaagatgg cgaaaccccg tctctactga aaatacaaag attagctggg   1740
catggtggta ggcacctgta attccagcta ctcggggagc tgaggcacga gaatcgcttg   1800
aacccaggag gcggaggttg cagcgagggg agatcacgcc actgcactgc agcctaggcg   1860
acagagggag actctgtttc aaaagaaaaa aaaaaactga aatggtagt ataagcatgt    1920 ttcttaagaa atggagagag aaattttgga agatatgcct tttaaaattc agtctggctc   1980
cctatgaaga ggagtagggc caaggacgat agtttgttgt tataagcctc atagaattat    2040
tttatattcc aaatacaaac attactttag caaaaattaa agttaaattt taaaaagagt   2100
ctagtaaaaa aaaaactaca ttatttgagt accaactgca tacatctttg acgagtacag   2160
ccattgcttc agtgtgtgga gtttatatgt gccccgtagg ttgtagttta ctaacatcaa   2220 atttagtta ggtgaattgg gaatagtatt cgttaaaaaa aaaaaaaaag caagaaaaga    2280
gaaggaaaag aaggagaaat ggtgtgagct cattgcatca gattagaggt agagcacagt   2340
aattttttaa agtagttttt tttttttttt tttttttttt taagaatagg cgtatcatgc   2400
tttggagagg ctgttgtgca gtggcaccat ctcaactcac tgcagcccca aactcctggg   2460
ttcaggcgat tctcccacct tggccttttgg tgtggctggg actacaggtg catgctgcca   2520
tgcctggcca atttttaaat ttttttgtaga acatgcatg gtctcgctgt gttgcccagg   2580
ctggtctcaa actcctggcc tcaaggtatc tcctctcctt ggcctcccaa agtgttggga   2640
ttacaggcct gagccaccac acctgcctcc atctttttga gatggagtct tgctcttgtc    2700
acccatgctg gagtgcagtg gtaccatctc agctcactgc aacctccgcc tcccaggttc   2760
aagtgattct cctgccttgg cctctcgagt agctgggatt acaggcacct gccactatgt   2820
ccagctaatt tttgtatttt tagtacagac gtggttttca ccatgttggc caggctggtc   2880
tcgaactcct gacctcaaat gatctgccca cccttgacctc ccaaagtgct ggctggggtg   2940
agccactgtg cctgggctta tatgtgatta attttctaag agtaaaaatt ctcatgccca   3000
acaataagtg gtgaataata tgattatagt acatccataa aataaacat ttagcagtca    3060 tataaaatgt tacattgtag taaaacattt gatgacaaaa taataatata tgttgttaaa   3120
tttgaacgtc aggaaatagc ttgtatgata aggtatgtat gaaacatact ataaactata   3180
```

```
tgcctagaaa aaagactgga cacaatcaag ggtgattatt ttctataggt ttcccctctc   3240
ctttgccccc agtattctac aatgacgtgt ataatcactg ctaagtattt aataaaaagt   3300
atgttcctaa tagtgattct ccagcagaac tgagttcacg aagatatcat caccctatgc   3360
cactttacct caatgtttct tgacatttac aaatctttct gggaatgtca cagtcacatc   3420
aaaagcagtg cttagggtta agtgtattct ttgggcactg agggtgggga aaggaagaga   3480
gaatagtaag tattcatcta caaatagctg tttcttgtag ctagaaaatt atcatatagt   3540
gagacacaca ggccaaaata aagccctgc agacattact gactattgta tatgaagaag    3600
ctgagatatg tgatgtatat gatgtagctg cagacgttac tgacgtgtat atgaagaagc   3660
tgattctgca gcaggtctgc tttttgatca ggcttctaga ctgtaaatgc tttcaaaaat   3720
gtacagggac catcatgtta attcatagca ttaaacaatg tatggaatgc ccactacgtt   3780
ccaggtatta tgctgagata ttgtggtgga aaatgaatat gccccccacc ctcatggagc   3840
atattgacta gaagggaaga tagatgatta aataaataat gacaaaaaac tctagtaaaa   3900
taattgggaa agtacaaagg agacagttct ggattggtga acctctcagg acaaaatgat   3960
taaggttaaa aaacttacct tatcatagta ccttgatacc gaggatgctc gatatgccct   4020
ttcttaattg ataaatagta aagaccctat aggtcagcta ttgggctgac ttaggggttc   4080
atattcgatc ttcagtaaga gtgcagtaca ctaagaggtt caaactggat tgcatcccca   4140
gattcacata tgaacaagtc tatatccttg aaaaaccag atcttaggga tccaacaggt    4200
tgaaactaac ccagggccaa gctgaacttt cagggcagtt ctcaaaataa ctgagctttg   4260
tggtcgttcc cgcgcacata ccccacaatt ggaatgatac agagaggatc agcatggccc   4320
ctgcgcaagg atgacacaca aattcatgaa gcagtccgta ttttaatttt aaaaaaatg    4380
agtttcacag gctgagcgtg tgtggccaga gccggactag aaccagatct tctggggcaa   4440
aggggcgagg ggaatgaatg acatttatcc aacacctagt tgtttttcc ctttagcagg    4500
aagtcattat gcaacttaca catattcatc agatttcctc tgacttaccc ggacatgtac   4560
atgggaatga tgtgcactgc caagaaatgt gggattaggt ttcagcctcc agctattatc   4620
ttaatctatg agagtgaaat caaggggaaa attcgccagc gcattatgcc agttcgaaac   4680
ttttcaaagt tttcaggtac ctcatgtctt atcttgcctc ctgtcttaaa tattctctaa   4740
atacaggttc acatcatgac tctgtcaggg actggatgtg tgacactgga tgaattactt   4800
actctcagtg agcttcagtt tcctaatcta taaagggaa ttgtagtgtt ttttccaat    4860
ctgataatta ataatccttt tgggattgct gcctaggtta aatgatatag cattattcaa   4920
taatattaat tcccttctct cattccaaat gttttttatt tgtagtctta atattttatt   4980
aataccacta ctgctatcta aaagctataa tatcactttt cttctcagac atattctcca   5040
gttgaaagtg tttaatatct ctacaaagtg atttttaagt taaagaagtc aaaactgtat   5100
ctgtccttct cccaccacac tgaaagctca atataaagga atggttctac aaagtaattc   5160
attccaatca agccatttag ctacttgact ataatggaga taatattttc agggttcaga   5220
gttttttgttc tgttttggct gttgcagtag tttatggcgt atatgatgta cgtggtacgt   5280
atgtggtata tagttttctt ctctctccca gattgcacca gagctgctga acaattaaag   5340
aataatccgc gacacaagag ttacctagaa caagtatccc tgaggcagct agagaagcta   5400
ttcagttttt tacgaggtta cttgtcgggg cagagtctgg cagaaacaat ggaacaaatt   5460
caacgggaaa caaccattga tcctgaggaa gacctgaaca aactagatga caaggagctt   5520
```

```
gccaaaagaa agagcatcat ggatgaactt tttgagaaaa atcagaagaa gaaggatgat    5580
ccaaattttg tttatgacat tgaggttgaa tttccacagg acgatcaact gcagtcctgt    5640
ggctgggaca cagagtcagc tgatgagttc tgataccaaa cactcaaaac atgcattggg    5700
ctagcagaat atccatgttt attaccagac tggttctgga agaagctgta aagaatacta    5760
aatatgttgg gttataggggg attgaccatg ttacttttca aaaccaggac atttaaagca    5820
tctactatgt aggtgcatga ggagtatggg aaaaacagaa taaggaatc tgcctttaag     5880 gagcttacaa tcatgccggg tgcggtggct cacgcctgta atcccagcac tttgggaggc    5940
tgaggcgggt ggatcaccta aggtcaggag ttcgagacca gcctagccaa catggtgaaa    6000
cctcgcctct actaaaaata caaaaattag ccaggcgtgg tggcgggtgc ctgtaatccc    6060
ggctactcag gaggctgagg caggagattc gcttgaacct gggaggctga ggttgcagtg    6120
agccgagatc gcgccattgt actccagcct gggcgatgag caaaactcca tctcaaaaaa    6180
aaaaaaaaaa aaaagcttac aatctgactg gaagatgtca aaacctgtga aaagctaatt    6240
agcagtatta agcaacacaa acattagtgc caaatgcatg ataaaggcta agaaggcca     6300 gagcatatat tactgtagag tagaatagta agggaagact ttgtccttta gtaaagagat    6360
aggaggtggc ctggcccttg aaatagtagt gtttaggtag atgcttgtgt aggattcctg    6420
ataagagcaa ctgaaaagaa ggagagggga agtagtaaag ggacaagaaa cattttttt    6480 tttgaggaac cataagcaaa ttatagtttg acaagacaag attgggggac atatatggtt    6540
accagggaat tacctcttat gtgttatatc tttatattat ttatctctgg aaaagagtac    6600
cctgcaaaat tccctacagc tgcaagcaga tgtcacttga tggacagagg gggaattctg    6660
cccctccggt atcgggaaat acatactaaa gacattgcga aacgctgaac ctcttcccat    6720
aaataaaagg tttgtttgta aaatgggaaa tccaccccata ataaatgaac aataggcact    6780
gccagtttag gcctgttcat gaatggatct gcaagacagc atcttcgttt aacaacatta    6840
tctgtgattt gatacattta tccttattac aatattgttt agttggtaga aattctatgt    6900
tttctacaag gaaattgatg tttattaaat aaaactgaaa ataattactc                6950

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
cttgttagga agccccacag                                                   20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
cgcaaggatg acacacaaat                                                   20

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide
```

```
<400> SEQUENCE: 6
ggaaactgaa gctcactgag agta                                          24

<210> SEQ ID NO 7
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 7
aatattttca gggttcagag ttttt                                         25

<210> SEQ ID NO 8
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 8
ttgaaaagta acatggtcaa tcc                                           23

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
cgcaaggatg acacacaaat                                               20

<210> SEQ ID NO 10
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 10
ggattgacca tgttactttt caa                                           23

<210> SEQ ID NO 11
<211> LENGTH: 14
<212> TYPE: PRT
<213> ORGANISM: Artificial sequence
<220> FEATURE:
<223> OTHER INFORMATION: Inactive mutant MO-1 polypeptide

<400> SEQUENCE: 11

Cys Thr Arg Ala Ala Glu Gln Leu Lys Asn Asn Pro Arg His
1               5                   10

<210> SEQ ID NO 12
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 12
tctacttctg gcagtacatc agtgaggc                                      28
```

<210> SEQ ID NO 13
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 13
aagtgagagt gggtgggtaa gggagtggg                                  29

<210> SEQ ID NO 14
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 14
tatgcctcag tacaggggaa cgccagtgc                                  29

<210> SEQ ID NO 15
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
ctgccttagc tgtctacatt gcttgg                                     26

<210> SEQ ID NO 16
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 16 cctcccttc cttttccctc tcagtgg                                     27

<210> SEQ ID NO 17
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 17
tggacctttg gaagagcagt cgggtgc                                    27

<210> SEQ ID NO 18
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 18
tgagaatgaa accgaaggaa agagccgc                                   28

<210> SEQ ID NO 19
<211> LENGTH: 26
<212> TYPE: DNA
<213> ORGANISM: Artificial sequence
<220> FEATURE:
<223> OTHER INFORMATION: Single strand DNA oligonucleotide

```
<400> SEQUENCE: 19
ggggaaaagg tttattcagc aggtcc                                        26

<210> SEQ ID NO 20
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 20
agtctctggt acgaatgcag cacactaagg                                    30

<210> SEQ ID NO 21
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 21
tggcagccca ctcacattga aacattcc                                      28

<210> SEQ ID NO 22
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 22
cttggtgatt tctgctcctg tgagtagc                                      28

<210> SEQ ID NO 23
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 23
acaaaaggca ccctctatcc tcttgagc                                      28

<210> SEQ ID NO 24
<211> LENGTH: 86
<212> TYPE: DNA
<213> ORGANISM: Artificial sequence
<220> FEATURE:
<223> OTHER INFORMATION: Sequence of the oligonucleotide used to create
      the SHA1-linker plasmid

<400> SEQUENCE: 24
cggcgcgcca cacgtgatcg cgatgacctg gtcagctagc actgcagaga cgtcaggccg   60
gcctatttaa attgcggccg cgagct                                        86

<210> SEQ ID NO 25
<211> LENGTH: 897
<212> TYPE: DNA
<213> ORGANISM: Artificial sequence
<220> FEATURE:
<223> OTHER INFORMATION: Sequence of the oligonucleotide used to create
      the SHA1-synthetic LA plasmid

<400> SEQUENCE: 25
tggtctagtg gacttctcaa cactaaatgt ttataaaatc aaaagtactg ggggtgtggc   60
```

```
atagccagtg cagtgcttgc ctgttatgct tgaagccctg ggttccatct tgagcaagcc      120
ctaaaccaag gttagtagca catactgtaa ttctaacact ggcaaataga gacaggagga      180
tcagaaatcc agggtcatcc tccactccat aacaaattca aagccaatct ggaccacatg      240
agatactgtc tggaaaaagg aaaaagttta aaggaacaaa gaggctgaat cagagatcct      300
ttagctgaaa catcaaatta ttctgaaggc cagccggtca gttcttgggc tcccaggagg      360
tcagtgtgta gtctctggta cgaatgcagc acactaaggg gtccaggccg aatgtcatta      420
ccgactcaga gatccaacga actgagtcaa acctagacca agactcacac tgtgtaagga      480
tacaatcctg gggctagtcc acagccgacc cacggagga gaaggggaaa aggtttattc       540
agcaggtccc tcgattatgc atgataactt cgtataatgt atgctatacg aagttattgg      600
ttgttcttct tcaggaaatt gttgtacaac tgtcctattt gtatcaggtt tcttccagtt      660
taccctgagt tacacgagaa gatgaaatac attgccaaga aatgtggagt taggttccag      720
cctccagctg tgatcttgat ttatgagaat gaaaccgaag gaaagagccg ccagcgtatc      780
atgcctgtcc gaaactttc aaagttctca ggtaccccctt gttttatctt gcctcctgtc      840
tagttctcta tttatttta tttatgtatg tatgtatgtg tctatgtgcg tgggtgt         897
```

```
<210> SEQ ID NO 26
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 26
ctacttccat ttgtcacgtc ctgcacg                                         27

<210> SEQ ID NO 27
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 27
ctggatttgg aagacggctg tgagc                                           25

<210> SEQ ID NO 28
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 28
ccagtcatag ccgaatagcc tctcc                                           25

<210> SEQ ID NO 29
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 29
agcattagga ggctgaagca ggagg                                           25

<210> SEQ ID NO 30
```

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 30
atgtggaatg tgtgcgaggc cagag                                       25

<210> SEQ ID NO 31
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 31
catatgtgca gtgctggcag agacc                                       25

<210> SEQ ID NO 32
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 32
ctggaccaca tgagatactg tctgg                                       25

<210> SEQ ID NO 33
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 33
ggtctgctac agatcagtct gttgg                                       25

<210> SEQ ID NO 34
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 34
cttggggctt caactgctac tgtcagg                                     27

<210> SEQ ID NO 35
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 35
ctggatttgg aagacggctg tgagc                                       25

<210> SEQ ID NO 36
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 36
```

```
gatttgtaaa ccccgtcagc cagtgg                                          26

<210> SEQ ID NO 37
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 37
tgtcaacgcc ttgaaggcag attcc                                           25

<210> SEQ ID NO 38
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 38
atgtggaatg tgtgcgaggc cagag                                           25

<210> SEQ ID NO 39
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 39
catatgtgca gtgctggcag agacc                                           25

<210> SEQ ID NO 40
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 40
actggagtcg gcttgtcagc tttcc                                           25

<210> SEQ ID NO 41
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 41
aagatcacag ctggaggctg gaaccg                                          26

<210> SEQ ID NO 42
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 42
atgtggaatg tgtgcgaggc cagag                                           25

<210> SEQ ID NO 43
<211> LENGTH: 25
<212> TYPE: DNA
```

<213> ORGANISM: Artificial sequence
<220> FEATURE:
<223> OTHER INFORMATION: Single strand DNA oligonucleotide

<400> SEQUENCE: 43

| catatgtgca gtgctggcag agacc | 25 |

<210> SEQ ID NO 44
<211> LENGTH: 1702
<212> TYPE: DNA
<213> ORGANISM: Mus musculus

<400> SEQUENCE: 44

| gagccttctg ttgccttggg aacgatcctc ggggcgccta ggtgggccct tggaccgggc | 60 |
| gagctgcctt aggaccgcac tccccgcgct cagccccgct tcctgcccac aaccggatgc | 120 |
| gtgcgggctg agcccccctgc ctctgagttc accccatggt tattcctgta ggctatggct | 180 |
| atcgccgttt cctgcagcgt caggctccac ctcgcctcaa agtcgaccta agctcctctg | 240 |
| tgcagtgcag taggatggaa accacccct cactgctgtt cagatgtgca cttcctgtac | 300 |
| ttcttcaagg acttgtactg agagcttaat gaaaatggac acaattcctg ccttcctaga | 360 |
| gcaaacagac taacagggaa gatacctggt ttcttccagt ttaccctgag ttacacgaga | 420 |
| agatgaaata cattgccaag aaatgtggag ttaggttcca gcctccagct gtgatcttga | 480 |
| tttatgagaa tgaaaccgaa ggaaagagcc gccagcgtat catgcctgtc cgaaactttt | 540 |
| caaagttctc agattgcacc agagctgcgg aacagttaaa gaataaccca cggcacaaga | 600 |
| gttacctgga acaggtgccc ctgaagcagc tggagaagct gtttgttttt ttgcgaggtt | 660 |
| ccttgcaggg gcagagcttg gcagaaacaa tggaacagat tcggcgggaa acgaccatcg | 720 |
| atcccgagga agacctgaac aaactggacg acaaggagct cgccaaaagg aagagcatca | 780 |
| tggatgagct tttcgagaaa atcagaagaa gaaggacga ccccacttt gtgtacgacg | 840 |
| tcgaggtgga gttccctcag gatgaacagc tgctgtcctg cagctgggac acagcgtcag | 900 |
| tggatgactt ctgaggaagc gctccacgtt tcctcagaga acaaagatca gttctagaaa | 960 |
| acgctgaaac actagcgatc tataaaacca ggacacttcc atgtgctacg taggcctatg | 1020 |
| agaaacacag aaatacaagg tgggaatctg ccttcaaggc gttgacaggc gacagcaaag | 1080 |
| ggaactcaag gacttgtaaa aagatatttt aataatatta ctcaggaaaa agataagagc | 1140 |
| cagattttga caaggggag gctttccctc agcggaaagg ggcccatgct tggccctgaa | 1200 |
| atgctacaga tgtttttgta gaaatcaaga tgaagcaaag agggaagggt gtggtaaaga | 1260 |
| gacaagaaat gggagaatct gagaaatggt gagtaattat agtttgacaa gattggaatt | 1320 |
| aacctgtgtt cttcaggact ctatgtgcat taactctggg gtagacagga gcacctgtaa | 1380 |
| atgcagaacg tctcacagct acgagtacat gtggcggatg gcaggcagtt ctactccgca | 1440 |
| atcaggaaat atggtctaac gttactctga acccagagc cacttcctgc gaaaggctgg | 1500 |
| tttgtacagt ggcaagtcct cccacaatga gtgataggta ctactgttca gacctgtttg | 1560 |
| tgagtttaga tgtacaaaga tctcggcctc acaaatcctc tgtgtgcaga tgtgtttgtt | 1620 |
| cttactagaa tattatctga ttgatagaaa tcgtatgttt tctacaagga aactattatt | 1680 |
| cattgaataa agctgtgacc gc | 1702 |

<210> SEQ ID NO 45
<211> LENGTH: 163
<212> TYPE: PRT
<213> ORGANISM: Mus musculus

```
<400> SEQUENCE: 45

Met Lys Tyr Ile Ala Lys Lys Cys Gly Val Arg Phe Gln Pro Pro Ala
1               5                   10                  15

Val Ile Leu Ile Tyr Glu Asn Glu Thr Glu Gly Lys Ser Arg Gln Arg
                20                  25                  30

Ile Met Pro Val Arg Asn Phe Ser Lys Phe Ser Asp Cys Thr Arg Ala
            35                  40                  45

Ala Glu Gln Leu Lys Asn Asn Pro Arg His Lys Ser Tyr Leu Glu Gln
        50                  55                  60

Val Pro Leu Lys Gln Leu Glu Lys Leu Phe Val Phe Leu Arg Gly Ser
65                  70                  75                  80

Leu Gln Gly Gln Ser Leu Ala Glu Thr Met Glu Gln Ile Arg Arg Glu
                85                  90                  95

Thr Thr Ile Asp Pro Glu Glu Asp Leu Asn Lys Leu Asp Asp Lys Glu
            100                 105                 110

Leu Ala Lys Arg Lys Ser Ile Met Asp Glu Leu Phe Glu Lys Asn Gln
            115                 120                 125

Lys Arg Lys Asp Asp Pro Thr Phe Val Tyr Asp Val Glu Val Glu Phe
            130                 135                 140

Pro Gln Asp Glu Gln Leu Leu Ser Cys Ser Trp Asp Thr Ala Ser Val
145                 150                 155                 160

Asp Asp Phe
```

MO-1 CONDITIONAL KNOCK-OUT NON-HUMAN ANIMAL AND USES THEREOF

RELATED APPLICATIONS

This application is a National Phase of PCT Patent Application No. PCT/IL2010/000920 having International filing date of Nov. 8, 2010, which claims the benefit of priority of Israel Patent Application No. 201999 filed on Nov. 8, 2009. The contents of the above applications are all incorporated herein by reference.

FIELD AND BACKGROUND OF THE INVENTION

The present invention, in some embodiments thereof, relates to a conditional MO-1 knock-out non-human animal and, more particularly, but not exclusively, to methods of generating and using same.

Obesity stems from a prolonged imbalance between the levels of energy intake and expenditure, with the resultant surplus being stored as body lipids. Our understanding of the regulation of food intake and the physiological basis of differences in energy expenditure is owed, in large part, to studies made in animals. Moreover, animal models have been a cornerstone of studies of environmental effects, such as epigenetics, responses to high-fat and low-calorie diets and the identification and development of pharmaceuticals for obesity treatment Obesity is a major risk factor for type II diabetes mellitus, heart disease, hypertension, metabolic syndrome, and cancer and is increasingly prevalent in Western society and in developing countries. Today, more than 1.1 billion individuals are overweight and more than 300 million are obese. Obesity is assessed by the calculation of the body mass index (BMI) [weight/(height)$^2$ in kg/m$^2$]. Individuals with a BMI higher or equal to 30 kg/m$^2$ are considered obese, whereas those with a BMI higher than 40 are morbidly obese. Despite intense scrutiny of this worldwide public health problem, the molecular and regulatory mechanisms which underlie the differences between lean and obese individuals remain largely unknown. Obtaining a better understanding of how energy balance is controlled should provide the framework for future clinical intervention and rational drug design.

In humans, the importance of genetic factors in obesity has been clearly defined through numerous twin, familial aggregation, and adoption studies. Indeed, through these studies heritability has been estimated as high as 40-90%. In the absence of rational gene candidates, genome-wide genetic association studies have emerged as a potentially powerful tool, and, as may be predicted, numerous genome-wide linkage studies have identified novel candidate gene loci for future studies. Unfortunately, these linkage studies have generally identified broad chromosomal regions containing scores of candidate genes and expressed sequence tags (ESTs). Two major problems now exist. First, the large number of genes within these regions need to be individually characterized and second, biologically plausible gene candidates within these regions are not always intuitively obvious: obesity-related genes may regulate a broad spectrum of physiologic pathways, including those governing satiety, basal metabolic rate, and activity. In addition, novel genes or those unrelated to the present, limited understanding of disease pathophysiology may go undetected.

Most striking with regard to the genetic basis of obesity and providing insights into its molecular basis has been the identification of gene mutations causing a number of Mendelian obesity disorders. These include leptin and leptin receptor deficiencies, melanocortin 4 receptor and POMC deficiencies and the pleiotropic syndromes Prader-Willi and Bardet-Biedl. Unfortunately, while each have provided insight into the molecular basis by which the hypothalamus controls satiety and energy homeostasis, none has provided insight into more common forms of obesity nor has yet provided a useful drug target for obesity and its comorbid features including diabetes.

An enormous number of transgenic models with obese or lean phenotypes have been created since the characterization of the first obesity genes. Of particular interest are mutations discovered in the peptide hormone, leptin, which is a component of a novel signal transduction pathway that regulates body weight [Zhang Y et al., Nature (1994) 372: 425-432; Chen H et al., Cell. (1996) 84(3):491-5]. Leptin was initially discovered by the positional cloning of the obesity gene, ob, in mice. Two different ob alleles have been identified: one mutation causes the premature termination of the leptin peptide resulting in a truncated protein, and the other mutation changes the transcriptional activity of the obesity (ob) gene, resulting in a reduced amount of circulating leptin. The genetically obese ob/ob mouse is a classic case of a spontaneous single-gene loss-of-function mutation that generates massive obesity.

The 2005 update of the human obesity gene map cited 248 genes that, when mutated or expressed as transgenes in mice, result in phenotypes that affect body weight and adiposity [Rankinen T et al., Obesity (2006) 14: 529-644]. Current sophisticated gene-targeting strategies enable investigators to manipulate the genome in ways that allow introduction of virtually any desired change. Furthermore, advanced techniques allow genome alterations that act at specific times only or that are expressed in specific tissues or cell types.

Knock-out mice also play an important role in the prospective identification of putative pharmaceutical targets for drug development. For example, Powell reviewed the phenotypes of 21 different types of knock-out mice where the gene knocked out was a potential therapeutic target for obesity. He found that, where data were available, the knock-out phenotypes mimicked not only the effects of therapeutics in rodents, but also the effects when relevant therapeutics targeting the same genes were delivered to humans. Transgenic mouse technology may therefore be a valuable tool to prospectively identify genes that regulate body fat in vivo, and then to develop anti-obesity therapeutics by targeting the human protein products of these genes or by interfering with levels of fat storage [Powell D R. Obes Rev (2006) 7: 89-108].

The development of the cannabinoid receptor type 1 antagonist rimonabant, is an example of a drug target that was identified in animals, led to the development of a class of potential obesity therapeutics and which ultimately generated a useable drug [Powell, supra; Speakman J et al., Obesity Reviews (2007) 8 (s1): 55-61].

U.S. Patent Application No. 2010/0077496 relates to the isolated MO-1 nucleic acids, MO-1 polypeptides, oligonucleotides that hybridize to MO-1 nucleic adds, vectors, including expression vectors, comprising MO-1 nucleic acids, as well as isolated host cells, antibodies, transgenic non-human animals, compositions, and kits relating to MO-1. Methods of detecting the presence of MO-1 nucleic acid, screening for agents which affect MO-1 activity, and screening for MO-1 variants are also disclosed therein.

Additional background art includes U.S. Pat. No. 7,446, 239, U.S. Patent Application No. 2010/0143934, U.S. Patent Application No. 2005/0158310 and PCT application No. WO 2000/066721.

SUMMARY OF THE INVENTION

According to an aspect of some embodiments of the present invention there is provided a conditional knock-out non-human animal, wherein some cells of the non-human animal but not all the cells comprise a disrupted MO-1 nucleic acid sequence, wherein the disruption results in an inability of the non-human animal to produce detectable levels of the MO-1 protein, as assayed by Southern blot analysis.

According to an aspect of some embodiments of the present invention there is provided an isolated tissue of the conditional knock-out non-human animal of some embodiments of the invention, wherein the tissue comprises the some cells which comprise a disrupted MO-1 nucleic acid sequence which results in an inability of the non-human animal to produce detectable levels of the MO-1 protein, as assayed by Southern blot analysis.

According to an aspect of some embodiments of the present invention there is provided a nucleic acid construct system comprising: (i) a first nucleic acid construct which comprises an MO-1 nucleic acid sequence and a selectable marker both flanked by loxP sites; (ii) a second nucleic acid construct which comprises a Cre recombinase under the control of a tissue specific promoter.

According to an aspect of some embodiments of the present invention there is provided a method of generating a non-human animal with a targeted conditional disruption in an MO-1 gene, the method comprising: (a) transfecting the first nucleic acid construct of some embodiments of the invention into a population of murine embryonic stem (ES) cells; (b) selecting a transfected ES cell which expresses the selectable marker; (c) introducing the transfected ES cell into an embryo of an ancestor of the non-human animal; (d) allowing the embryo to develop to term to produce a chimeric non-human animal with a conditional knock-out construct in its germ line; (c) breeding the chimeric non-human animal with a non-human animal expressing flippase to produce a heterozygous non-human animal which does not contain the selectable marker; and (f) breeding the heterozygous non-human animal with a non-human animal expressing a Cre recombinase under the control of a stage- or tissue-specific promoter to produce the non-human animal with the targeted conditional disruption in the MO-1 gene.

According to an aspect of some embodiments of the present invention there is provided a method of screening for a test agent which modulates metabolic activity, the method comprising: (a) contacting the agent with the non-human animal of some embodiments of the invention or the isolated tissue of some embodiments of the invention; and (b) analyzing a phenotype of the tissue or the non-human animal; (c) comparing the phenotype following the contacting to prior to the contacting, wherein an alteration in the phenotype is indicative of an agent which modulates metabolic activity.

According to some embodiments of the invention, the disrupted MO-1 nucleic acid sequence comprises an endogenous nucleic acid sequence encoding MO-1.

According to some embodiments of the invention, the disrupted MO-1 nucleic acid sequence has been introduced into the non-human animal by homologous recombination in an embryonic stem cell of the non-human animal.

According to some embodiments of the invention, the disrupted MO-1 nucleic acid sequence has been introduced into the non-human animal by a knock-out nucleic acid construct.

According to some embodiments of the invention, the knock-out nucleic acid construct comprises at least a portion of an MO-1 gene, wherein exon 3 of the MO-1 gene is flanked by a 5' loxP site and a 3' selectable marker cassette, wherein the selectable marker cassette is flanked by frt sites 3' and a 5' to the frt, and further wherein a loxP site is positioned 3' to the 3' frt site.

According to some embodiments of the invention, the conditional knock-out non-human animal comprises a recombinant MO-1 allele containing a neomycin gene and loxP sites flanking at least a portion of a MO-1 gene.

According to some embodiments of the invention, the at least a portion of the MO-1 gene comprises Exon 3 of the MO-1 gene.

According to some embodiments of the invention, the conditional disruption is induced by breeding the non-human animal with a non-human animal expressing a Cre recombinase under the control of a stage- or tissue-specific promoter.

According to some embodiments of the invention, the conditional disruption is induced by expressing in the non-human animal a transgene encoding a Cre recombinase under the control of a stage- or tissue-specific promoter.

According to some embodiments of the invention, the conditional disruption occurs in exon 3 of a MO-1 gene.

According to some embodiments of the invention, the some cells of the non-human animal comprise liver cells.

According to some embodiments of the invention, the some cells of the non-human animal comprise pancreatic cells.

According to some embodiments of the invention, the some cells of the non-human animal comprise muscle cells.

According to some embodiments of the invention, the some cells of the non-human animal comprise kidney cells.

According to some embodiments of the invention, the some cells of the non-human animal are comprised in two or more tissues.

According to some embodiments of the invention, the non-human animal exhibits at least one phenotype selected from the group consisting of obesity, diabetes, cardiac disease, hypertension, and fatty liver.

According to some embodiments of the invention, the first nucleic acid construct comprises a portion of an MO-1 gene, wherein exon 3 of the MO-1 gene is flanked by a 5' loxP site and a 3' selectable marker cassette, wherein the selectable marker cassette is flanked by frt sites 3' and a 5' to the frt, and further wherein a loxP site is positioned 3' to the 3' frt site.

According to some embodiments of the invention, the non-human animal is a mammal.

According to some embodiments of the invention, the mammal is a mouse.

According to some embodiments of the invention, the mouse comprises a C57BL/6J mouse.

According to some embodiments of the invention, the mammal is a rat.

According to some embodiments of the invention, the mammal is a rabbit.

According to some embodiments of the invention, the mammal is a hamster.

According to some embodiments of the invention, the mammal is a sheep.

According to some embodiments of the invention, the selectable marker comprises neomycin.

According to some embodiments of the invention, the phenotype comprises MO-1 expression or activity.

According to some embodiments of the invention, the metabolic activity in the non-human animal is selected from the group consisting of food consumption, body weight, oxygen consumption, locomotor activity, heat production, rate of energy expenditure and body fat oxidation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
Figure 1B:
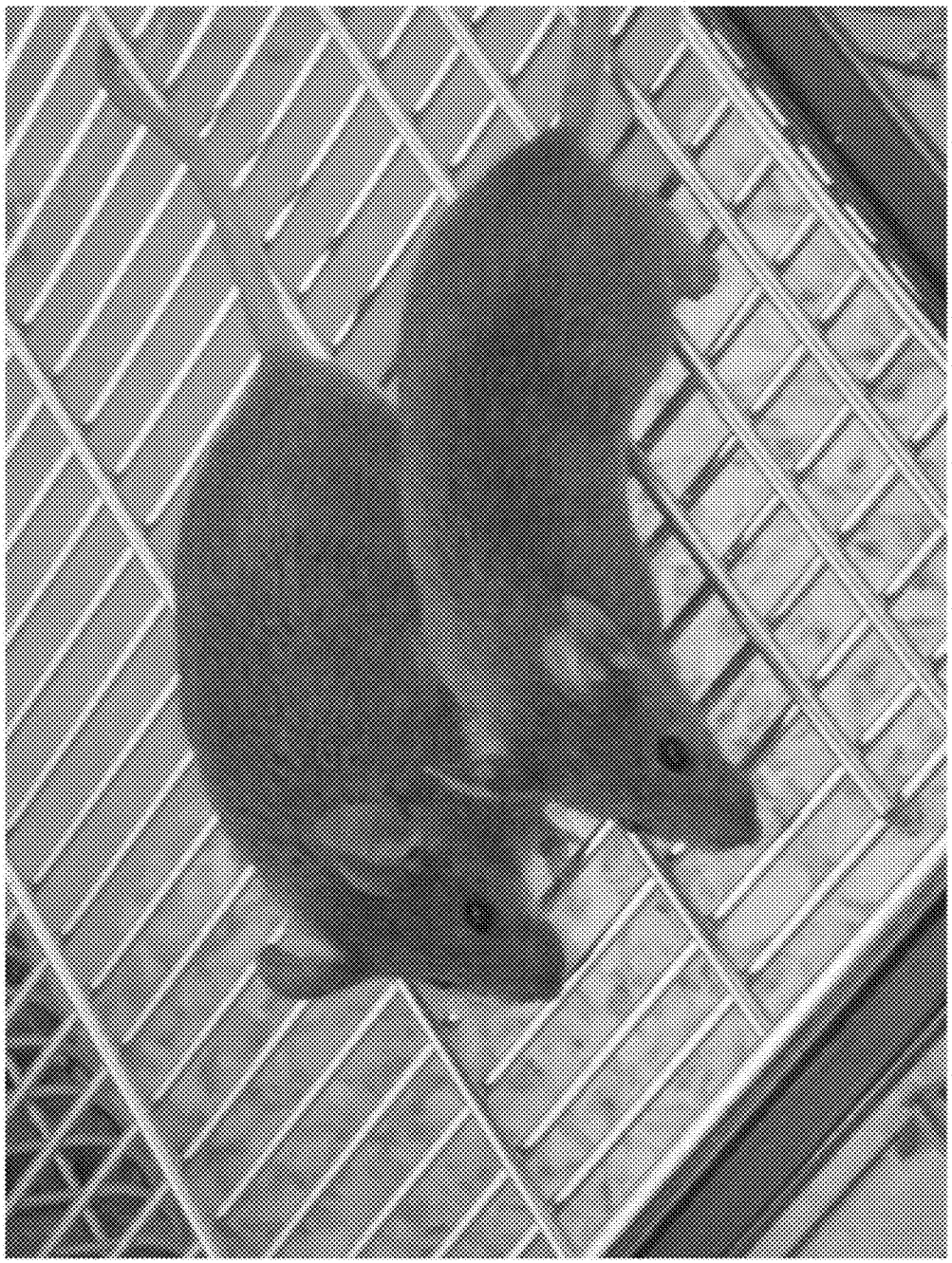

FIGS. 1A-B are pictures of MO-1 knock-out (MO-1 KO) mice. FIG. 1A illustrates a HMZ male KO mouse on the right, and Wild type on the left; FIG. 1B illustrates a HMZ male KO mouse on the top and a wild type mouse on the bottom.

FIGS. 2A-C are illustrations of the human MO-1 polypeptide and cDNA sequences. FIG. 2A illustrates the MO-1 polypeptide sequence, presumed initial methionine is shown in parenthesis; FIG. 2B illustrates the MO-1 cDNA sequence, presumed start and stop codons are shown in bold underlined text; and FIG. 2C illustrates the MO-1 genomic DNA sequence, introns and flanking sequences are illustrated in lower case while exons are illustrated in upper case.

Figure 3:
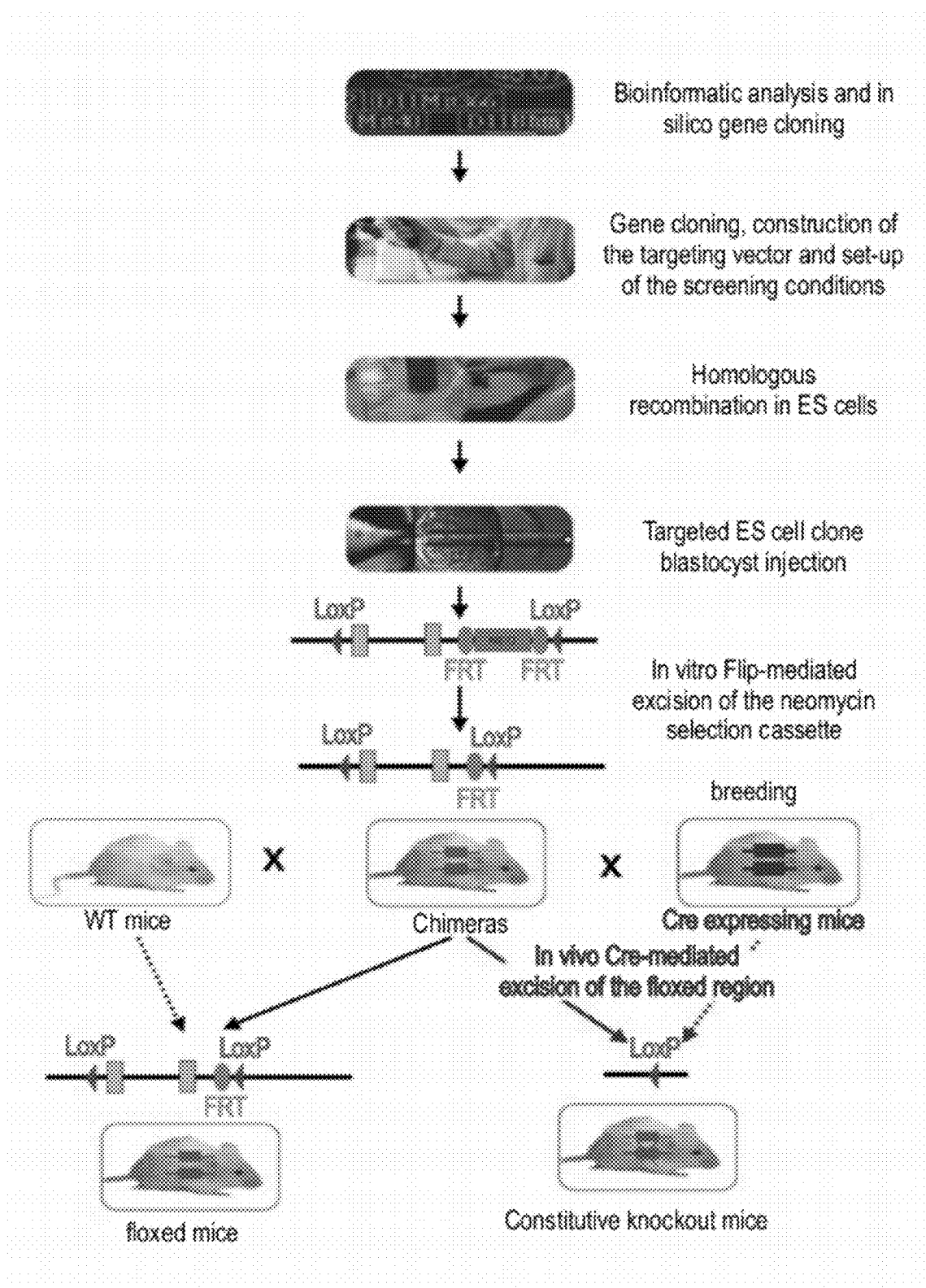

FIG. 3 is a flow chart illustrating the principle of the double constitutive and conditional knock-out approach. Grew boxes represent exons. Solid lines represent intronic sequences. LoxP and FRT elements are shown as blue triangles and orange circles, respectively. Neo represent the neomycin positive selection cassette.

Figure 4:
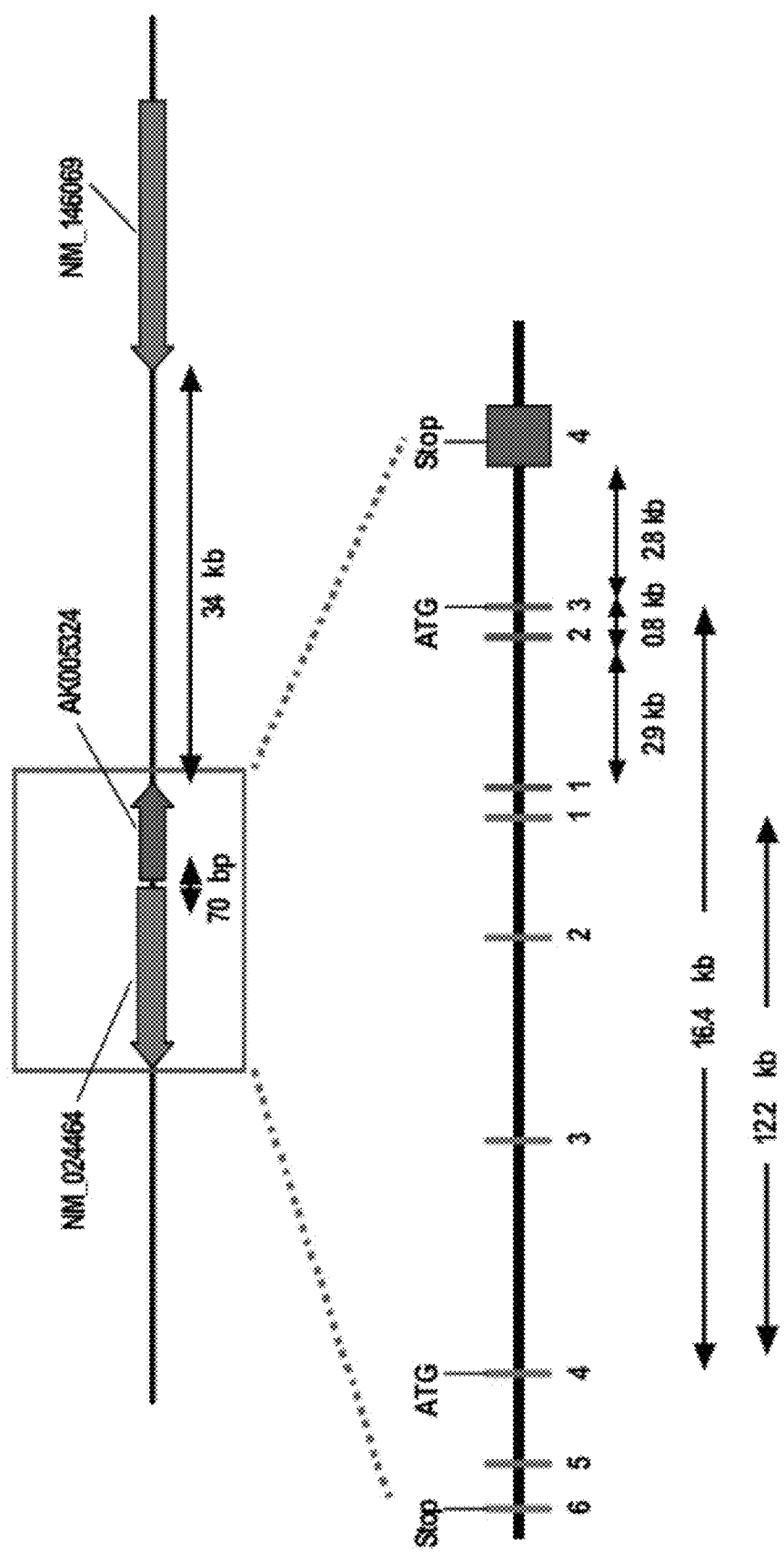

FIG. 4 is a schematic representation of the AK005324 locus region. Exons are represented by Hatched boxes. Solid line represents intronic sequences. The AK005324 locus is depicted in red, the neighboring genes are depicted in green.

Figure 5:
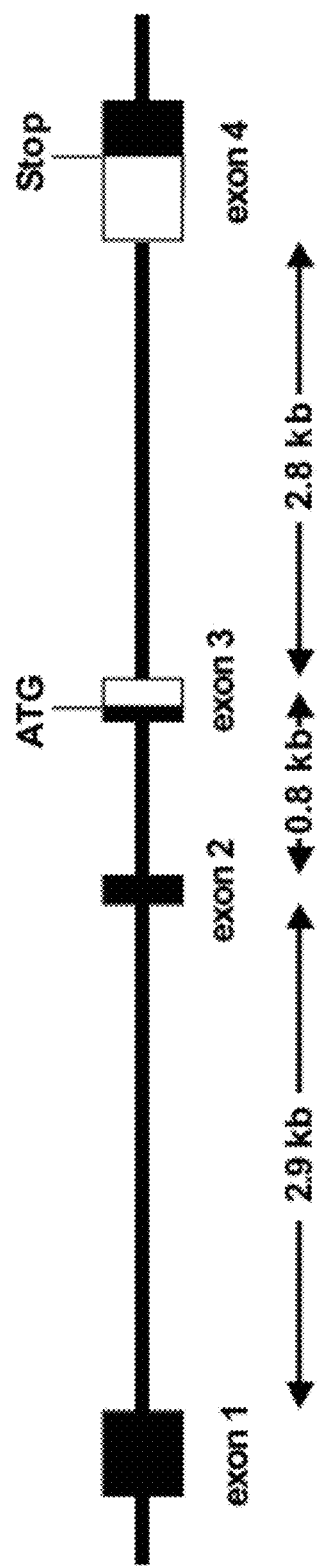

FIG. 5 is a schematic representation of the AK005324 locus organization. Hatched and black boxes represent coding exons and UTR, respectively. Solid line represents intronic sequences. The sizes of the three introns are also depicted.

Figure 6:
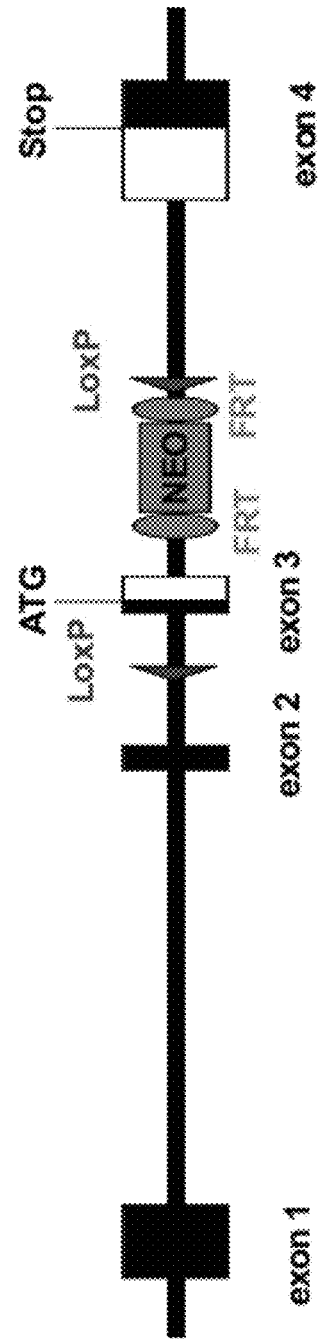

FIG. 6 is a schematic representation of the targeted AK005324 locus. Black and grey-hatched rectangles represent non-coding and coding exons, respectively. Solid line represents chromosome sequence. The initiation codon (ATG) and stop codon (Stop) are indicated. Blue triangles and orange circles represent LoxP and FRT sites, respectively. Green box represents the neomycin positive selection cassette. Of note, the scheme is not depicted to scale.

Figure 7:
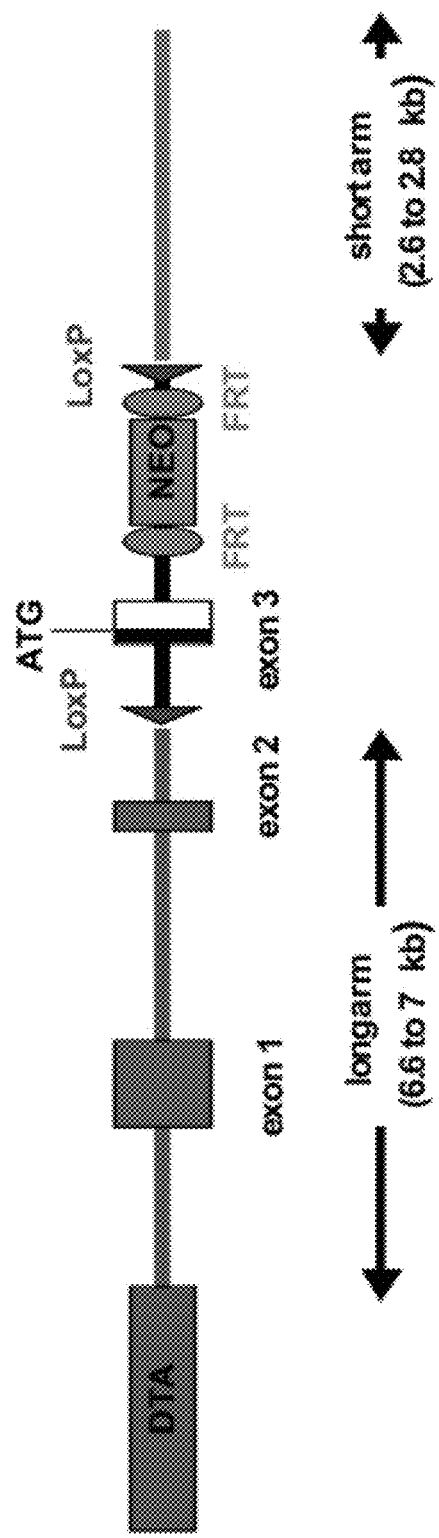

FIG. 7 is a schematic representation of the targeting vector. Boxes represent AK005324 exons. Solid line represents AK005324 intronic sequences. For clarity purpose, the phosphatidylinositol glycan, class X exon1 is not represented. LoxP and FRT elements are shown as blue triangles and orange circles, respectively. Neo and DTA boxes represent the neomycin positive selection cassette and the DTA negative selection cassette, respectively. Of note, the scheme is not depicted to scale.

Figure 8:
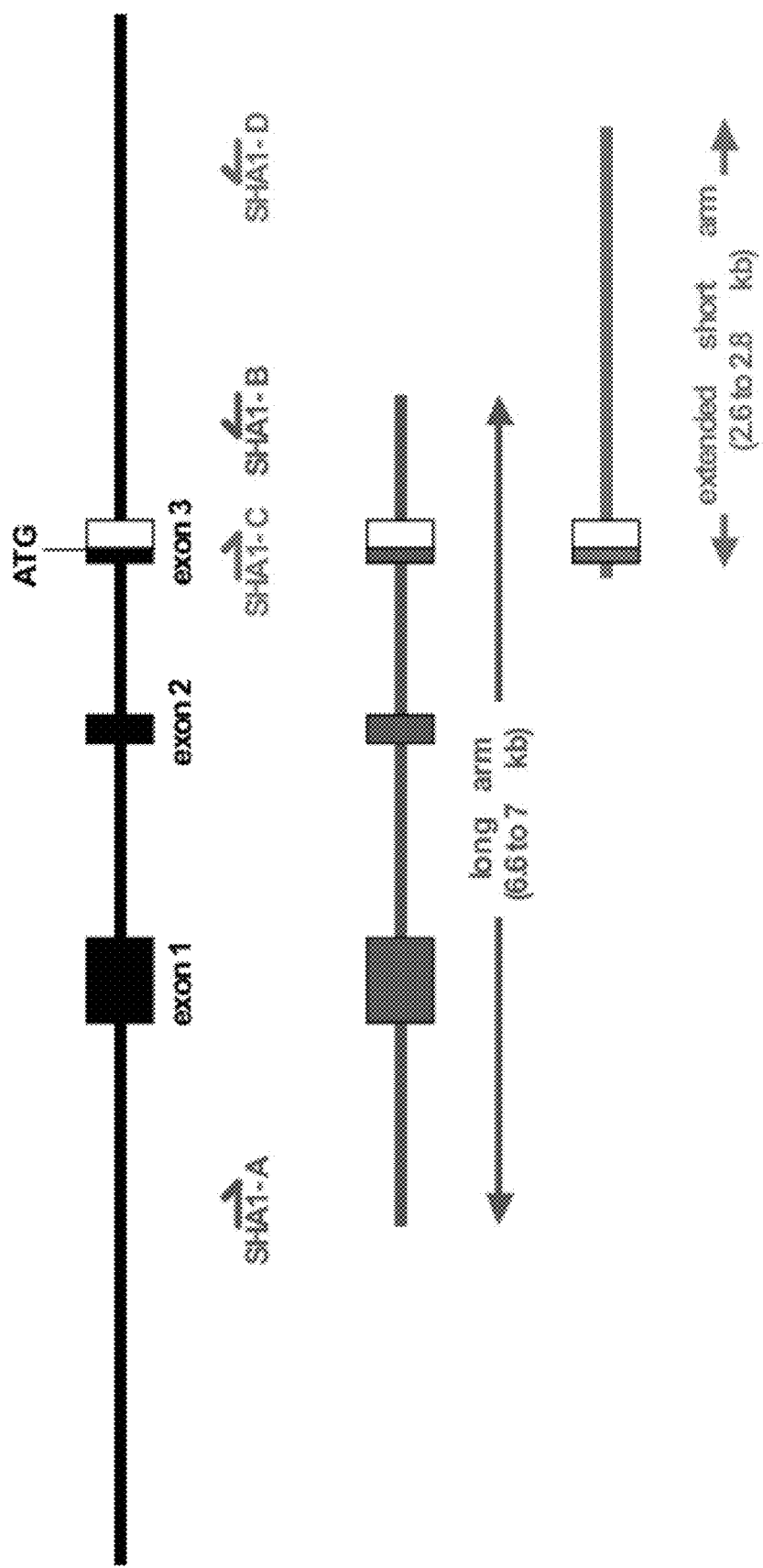

FIG. 8 is a schematic illustration of the position of the PCR primers used for the amplification of the long and extended short homology arms. For clarity purpose, the phosphatidylinositol glycan, class X exon1 is not represented. Half arrows represent the position of the different primers. The sizes of the amplicons are indicated. Of note, the scheme is not depicted to scale.

Figure 9:
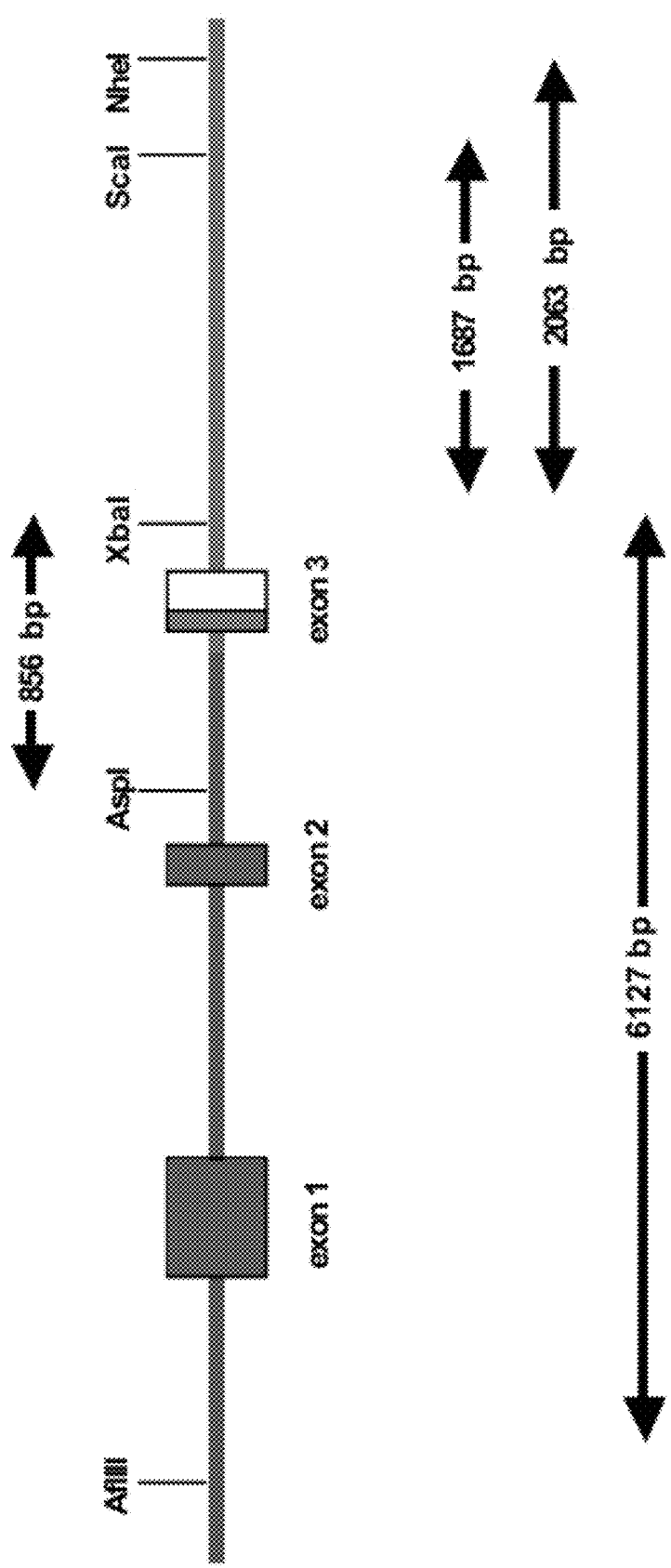

FIG. 9 is a schematic illustration of the position of the restriction used for the isolation of the different homology arms. The scheme is not depicted to scale. For clarity purpose, the phosphatidylinositol glycan, class X exon1 is not represented. The distances between restriction sites are indicated.

Figure 10:
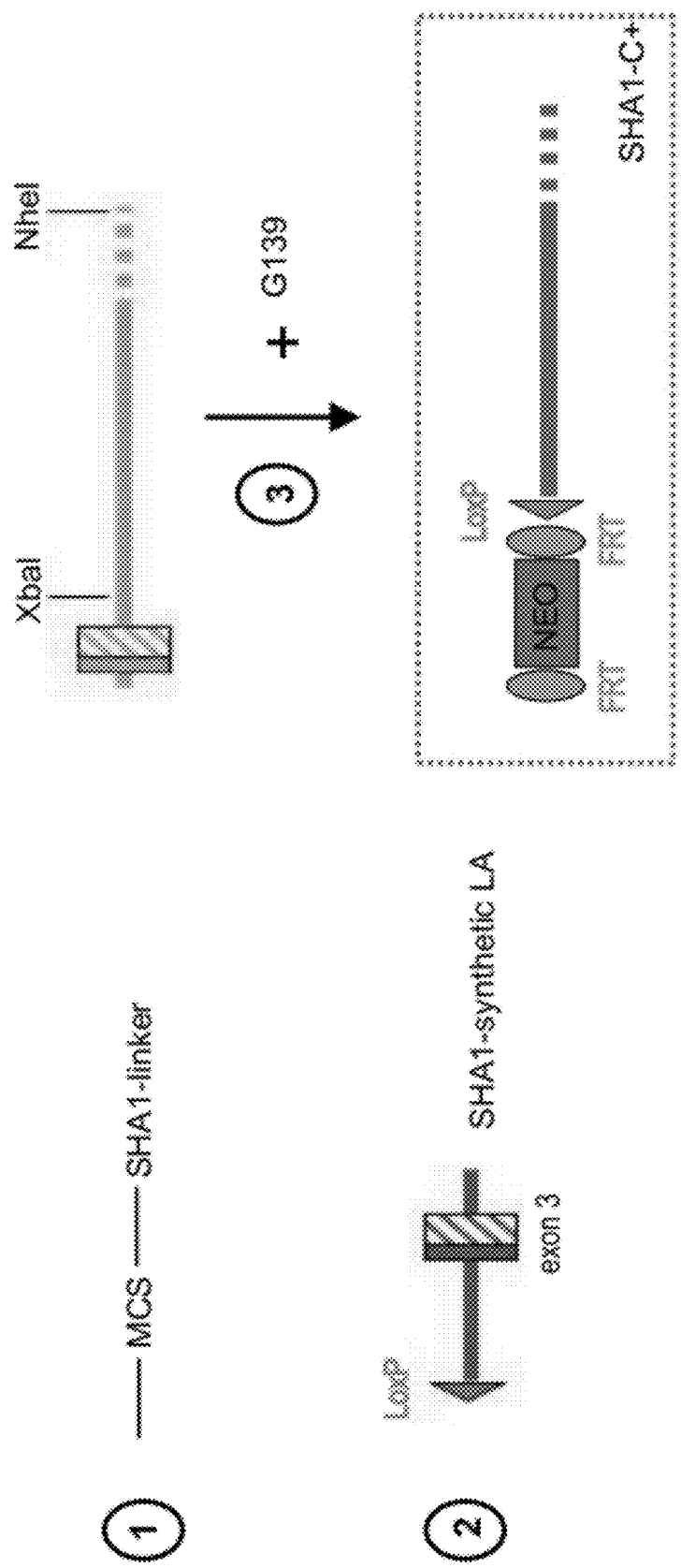

FIG. 10 is a schematic representation of the linkers and positive control vector constructions. Cloning steps are represented by circled numbers and are described in the text. MCS stands for multiple cloning sites. Of note, the scheme is not to scale.

Figure 11:
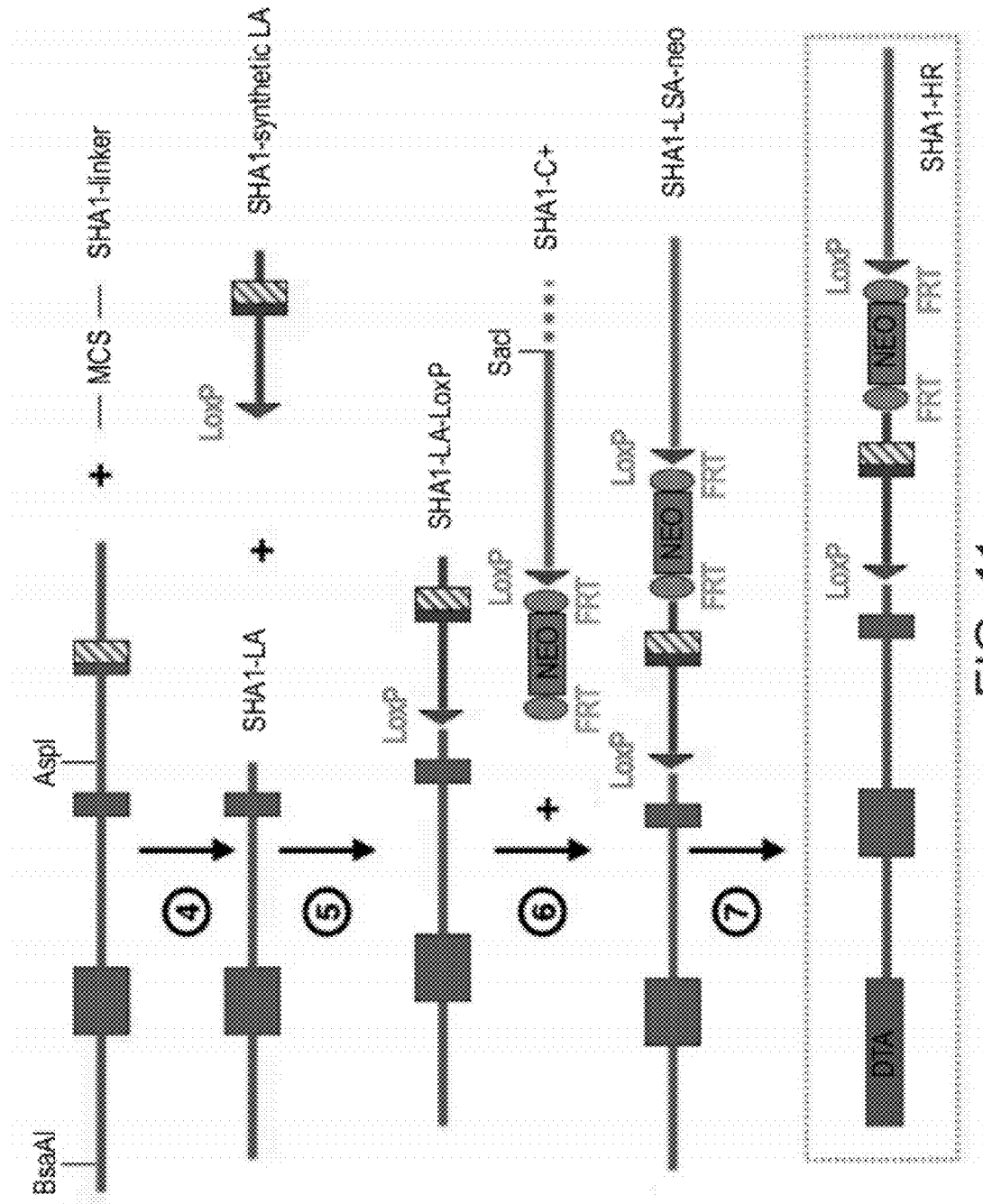

FIG. 11 is a schematic representation of the targeting vector construction strategy. Cloning steps are represented by circled numbers and are described in the text. Of note, the scheme is not to scale.

Figure 12:
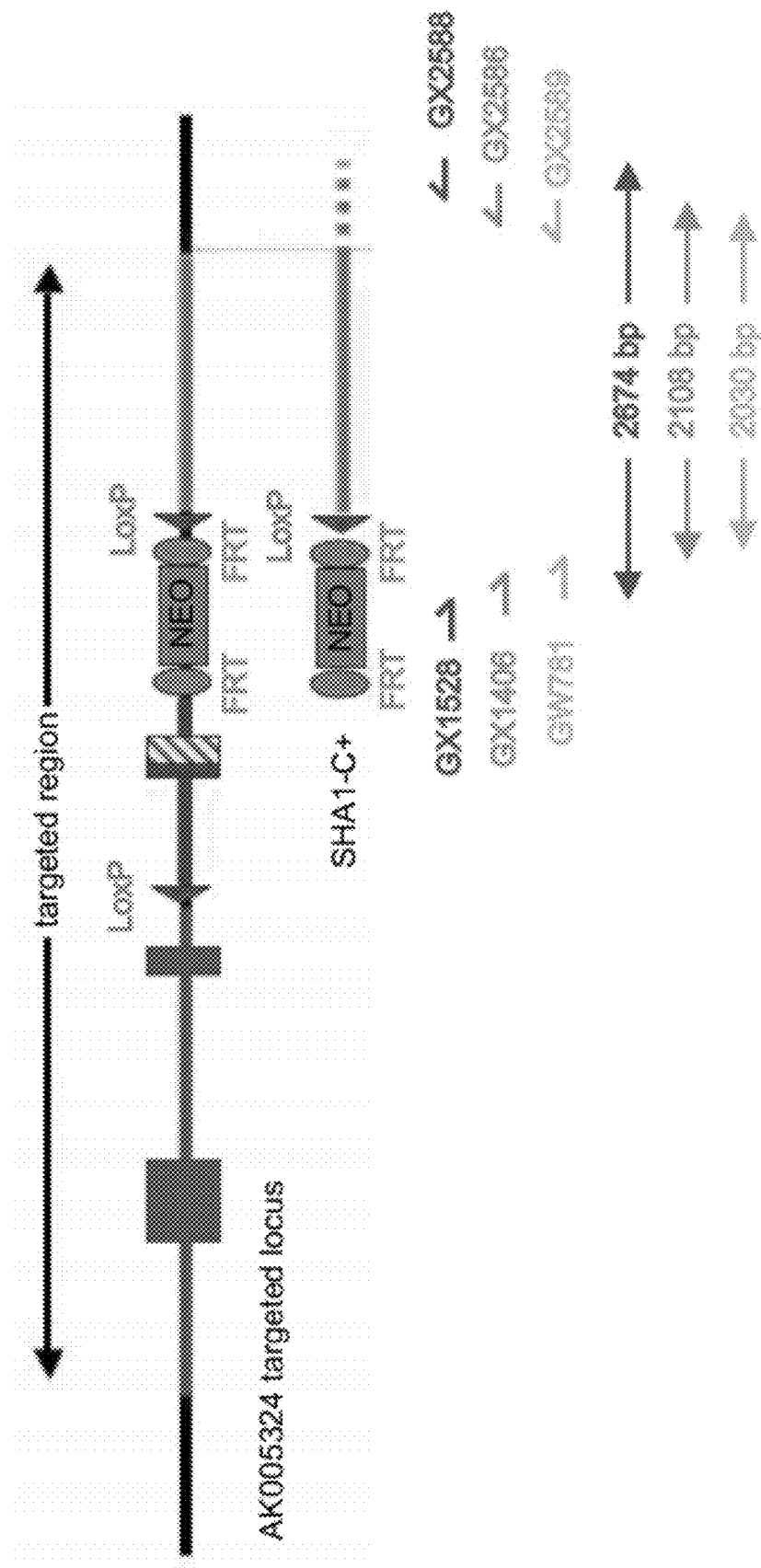

FIG. 12 is a schematic illustration of PCR screening for identification of the 3' end homologous recombination event. Half arrows illustrate the primers localization.

Figure 13:
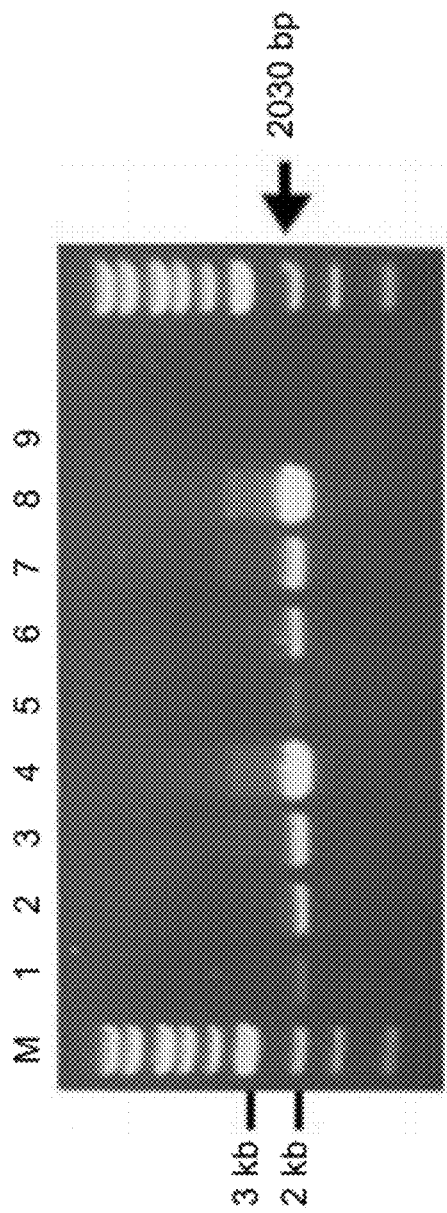

FIG. 13 is a photograph representing an example of the 3' PCR screenings for the identification of the homologous recombination event. GX781/GX2589 primer set, amplicon size 2030 bp, half of the PCR reaction is loaded on the gel. Lanes M: 1 kb DNA Ladder (NEBiolabs); Lanes 1 to 4: 0.1, 0.5, 1 and 10 genomic equivalent copies of SHA1-C+ vector; Lanes 5 to 8: 0.1, 0.5, 1 and 10 genomic equivalent copies of SHA1-C+ vector spiked in 10 ng of C57Bl/6 genomic DNA; and Lane 9: PCR control, 150 ng of ES cell genomic DNA.

Figure 14:
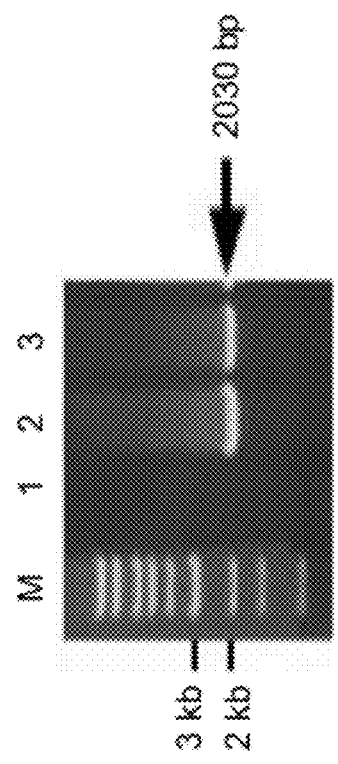

FIG. 14 is a photograph representing an example of the 3' PCR screenings for the identification of the homologous recombination event. GX781/GX2589 primer set, amplicon size 2030 bp, half of the PCR reaction is loaded on the gel. Lanes M: 1 kb DNA Ladder (NEBiolabs); Lane 1: PCR control, 150 ng of ES cell genomic DNA; Lane 2: 400 ng of genomic DNA extracted from ES cell clone #1B3 stable transfectant of the SHA1-C+ vector; and Lane 3: positive control, 1 genomic equivalent copies of SHA1-C+ vector spiked in 10 ng of C57Bl/6 genomic DNA.

Figure 15:
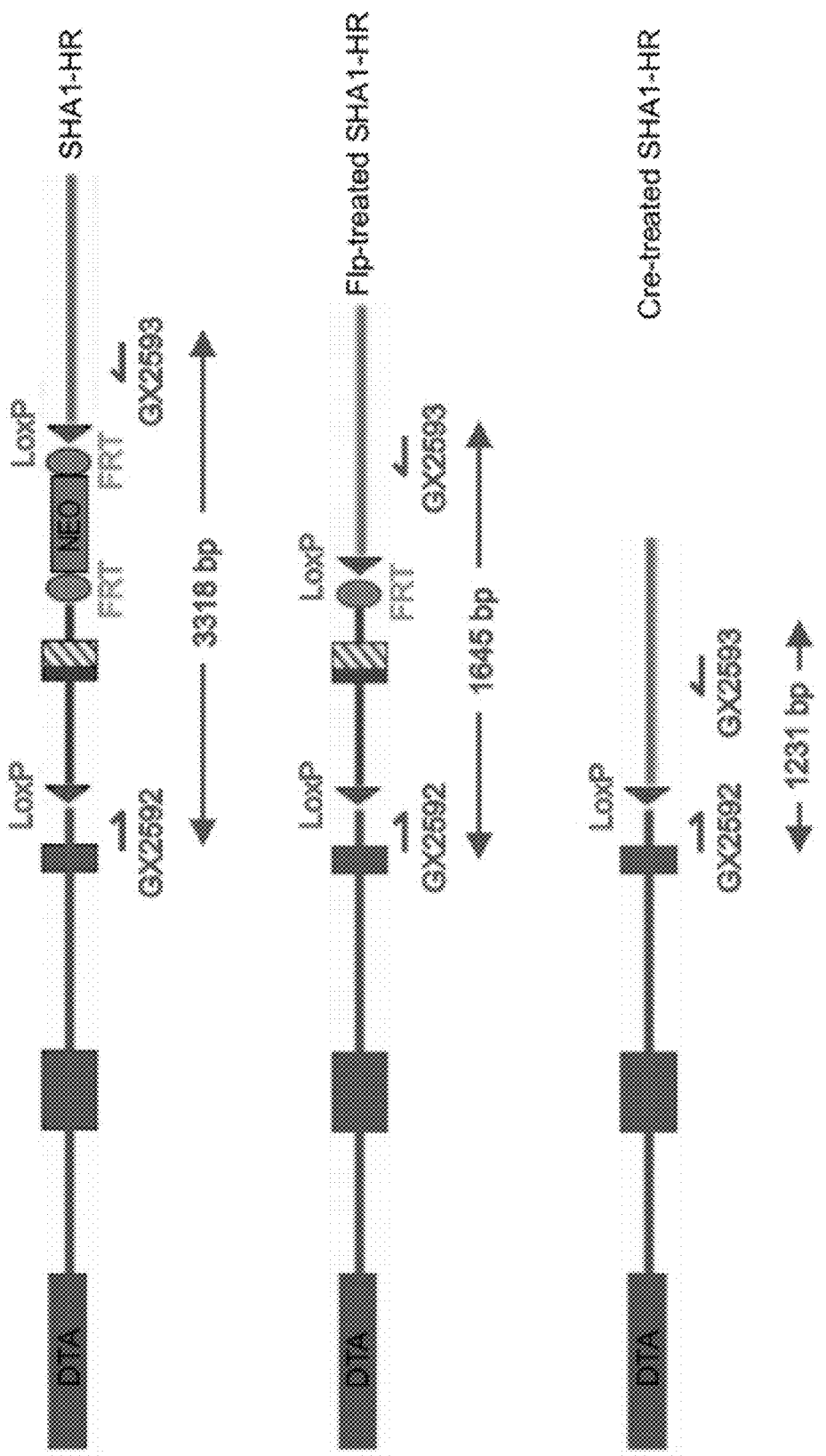

FIG. 15 is a schematic illustration of PCR screening for the in vitro validation of FRT and LoxP sites functionality. Half arrows illustrate the primers localization.

Figure 16:
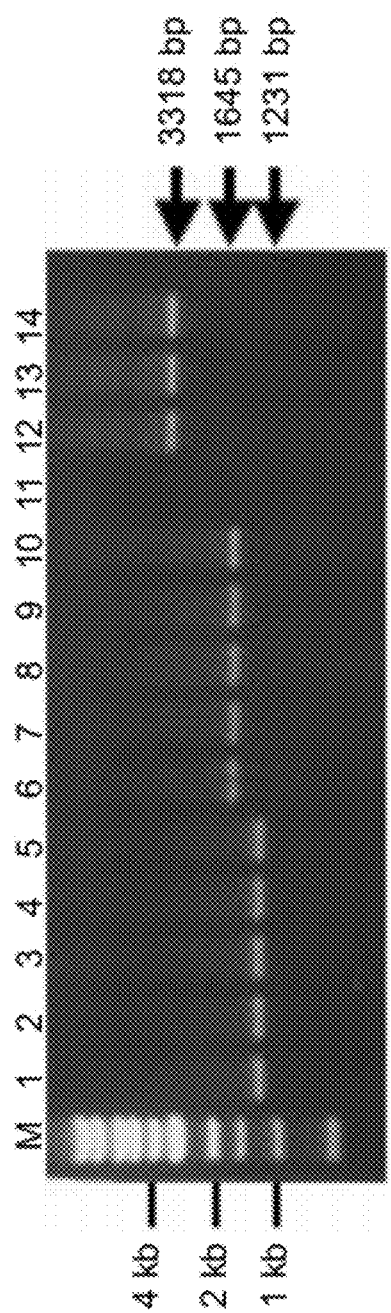

FIG. 16 is a photograph representing an example of the PCR used for the in vitro validation of FRT and LoxP sites functionality. GX2592/GX2593 primer set, amplicon sizes: 3318-bp on SHA1-HR vector, 1645-bp on Flip-treated SHA1-HR vector and 1231-bp on Cre-treated SHA1-HR vector. Half of the PCR reaction is loaded on the gel. Lane M: 1 kb DNA Ladder (NEBiolabs); Lanes 1 to 5: Cre-treated SHA1-HR vector, 5 colonies; Lanes 6 to 10: Flip-treated SHA1-HR vector, 5 colonies; Lane 11: PCR control, mock transfected bacterial strain; and Lanes 12 to 14: SHA1-HR vector, 3 colonies.

Figure 17:
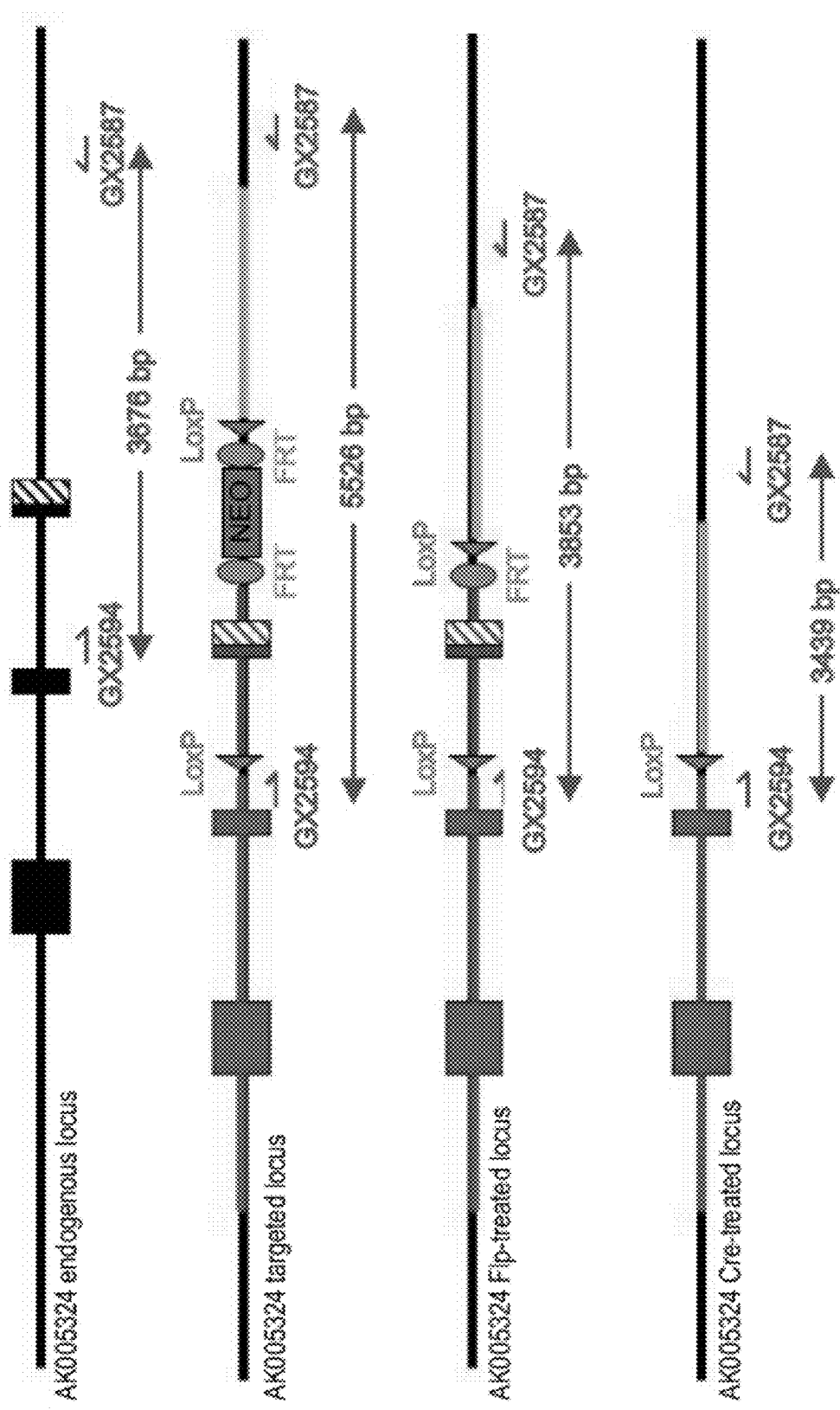

FIG. 17 is a schematic illustration of a PCR screening for identification of Flp-mediated excision of the neomycin selection cassette and Cre-mediated excision of the floxed region. Half arrows illustrate the primers localization.

Figure 18:
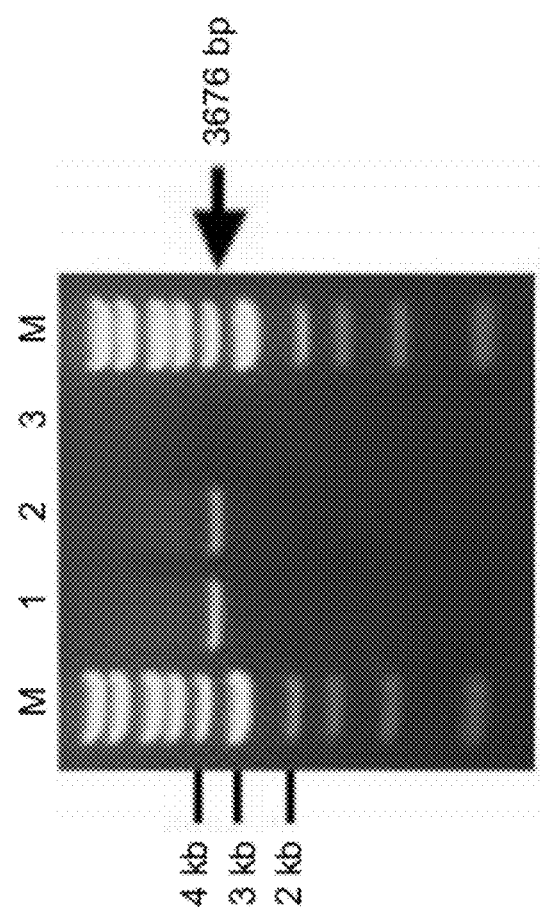

FIG. 18 is a photograph representing an example of the PCR used for the detection of the Flip-mediated excision of the neomycin positive selection cassette and Cre-mediated excision of the floxed region. GX2587/GX2594 primer set, amplicon size 3676-bp, half of the PCR reaction is loaded on the gel; Lanes M: 1 kb DNA Ladder (NEBiolabs); Lane 1: 150 ng of genomic DNA extracted from WT ES cells; Lane 2: 10 ng of genomic DNA extracted from C56Bl/6 mouse tail biopsy; and Lane 3: PCR control, H$_2$0.

Figure 19:
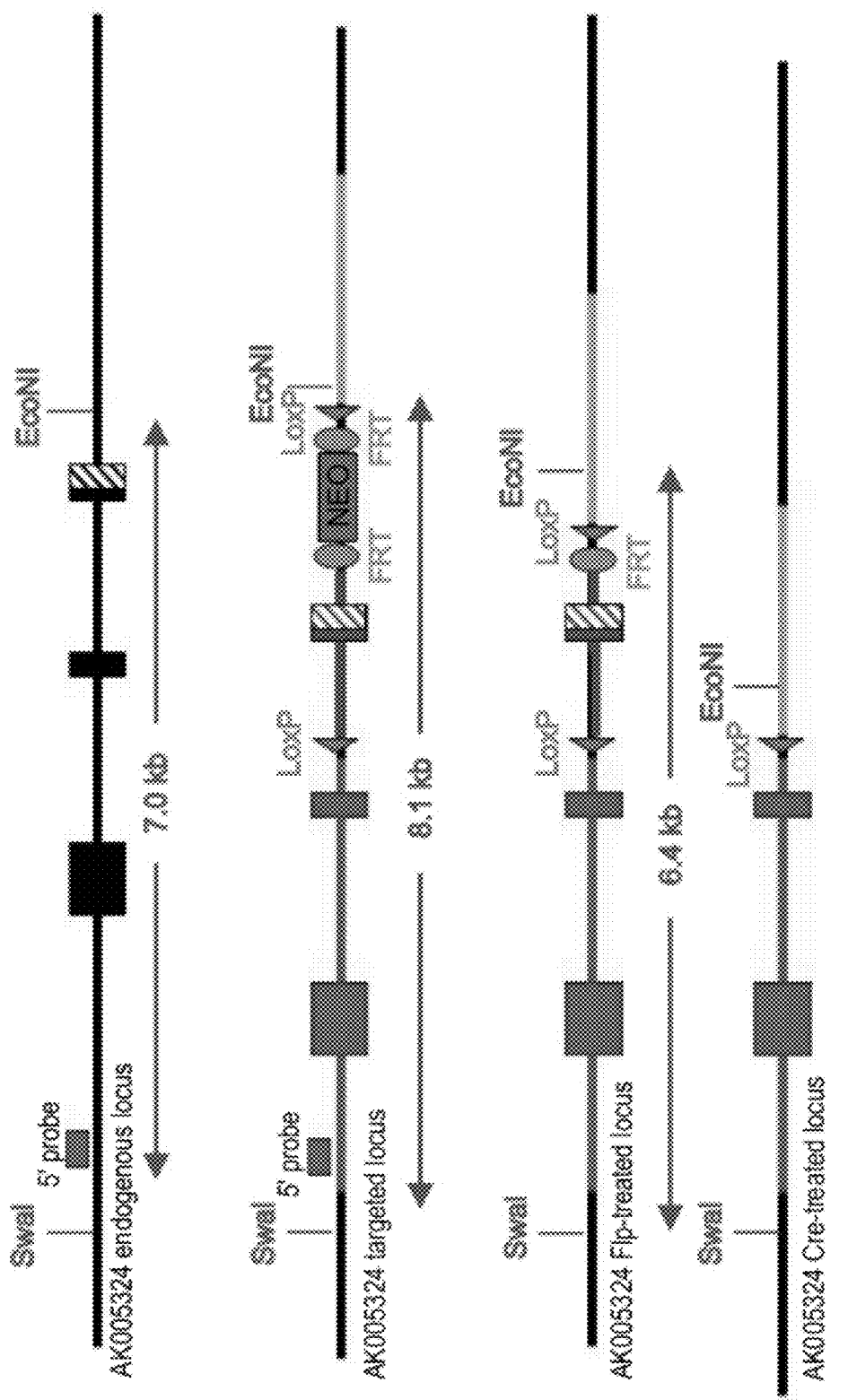

FIG. 19 is a schematic representation of the 5' southern blot screening strategy.

Figure 20:
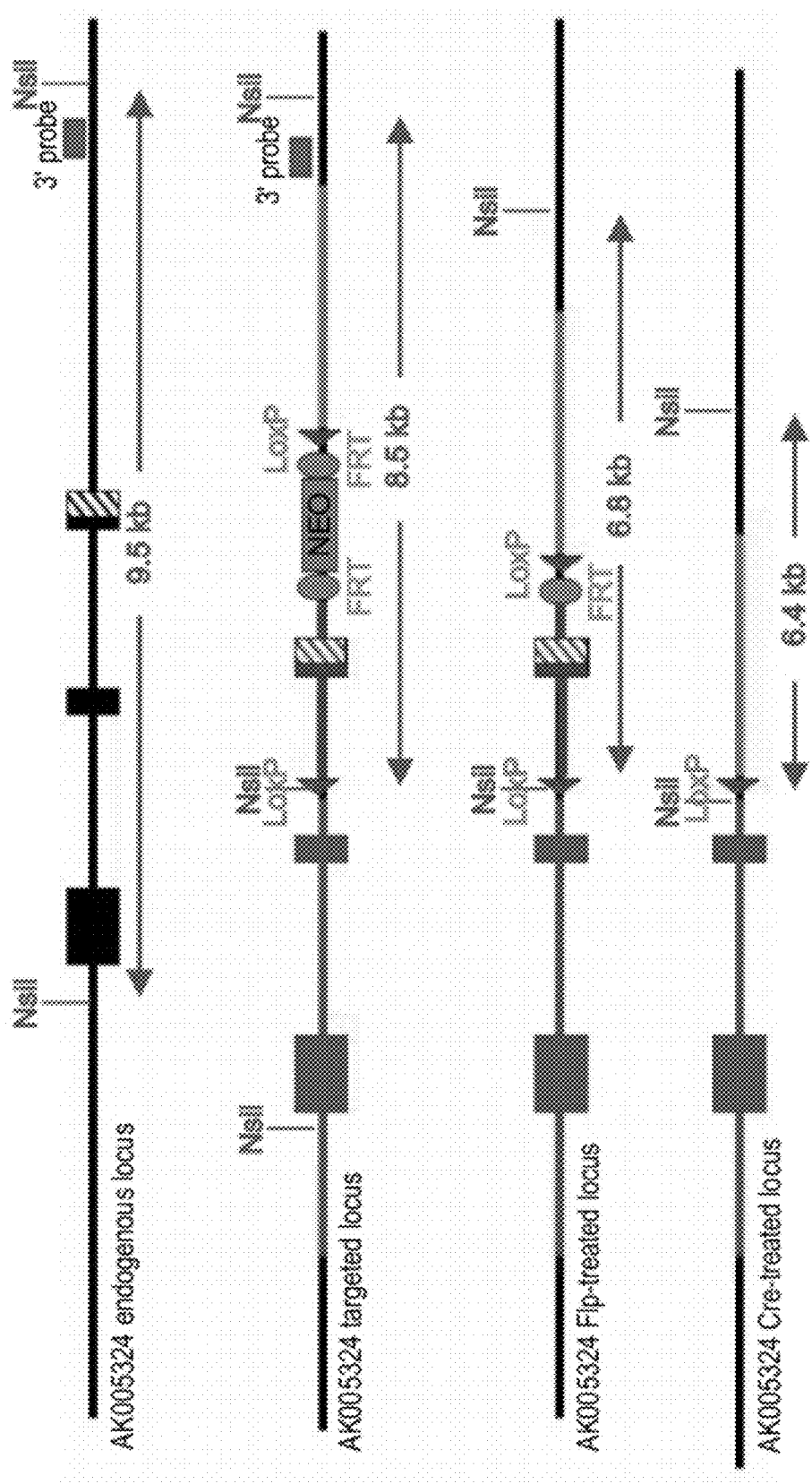

FIG. 20 is a schematic representation of the 3' southern blot screening strategy.

Figure 21:
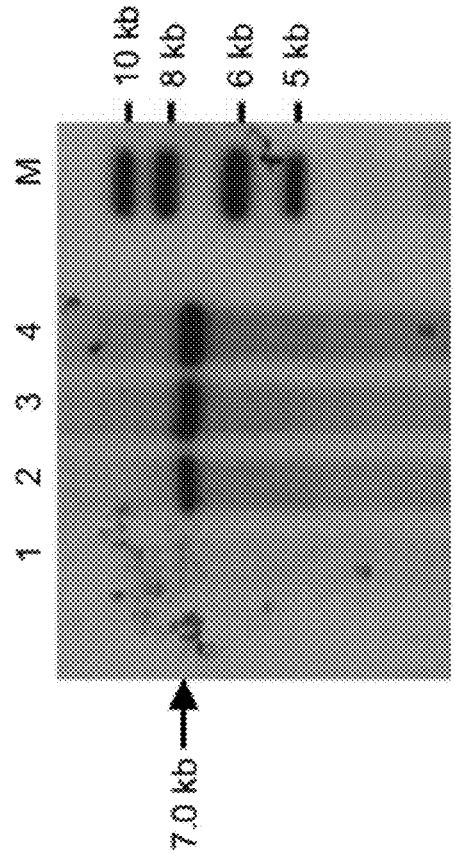

FIG. 21 is a photograph depicting a 5' Southern blot screening strategy on wild type genomic DNA. Lane M: 1 kb DNA ladder (BioLabs), Lane 1: 4 μg of genomic DNA extracted from WT ES cells (129/SvPas), Lane 2: 15 μg of genomic DNA extracted from WT ES cells (129/SvPas), Lane 3: 15 μg of genomic DNA extracted from C57Bl/6J mouse tail biopsies and Lane 4: 15 μg of genomic DNA extracted from WT ES cells (129/Ola).

Figure 22:
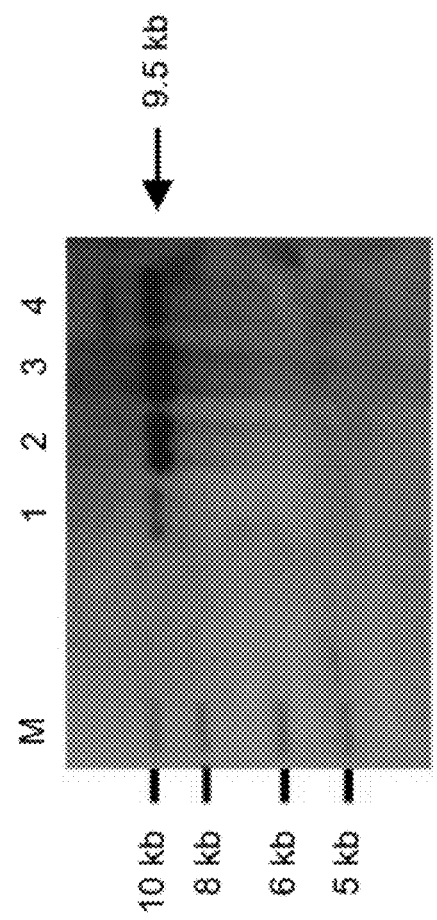

FIG. 22 is a photograph depicting a 3' southern blot screening strategy on wild type genomic DNA. Lane 1: 4 μg of genomic DNA extracted from WT ES cells (129/SvPas), Lane 2: 15 μg of genomic DNA extracted from WT ES cells (129/SvPas), Lane 3: 15 μg of genomic DNA extracted from C57Bl/6J mouse tail biopsies and Lane 4: 15 μg of genomic DNA extracted from WT ES cells (129/Ola).

Figure 23:
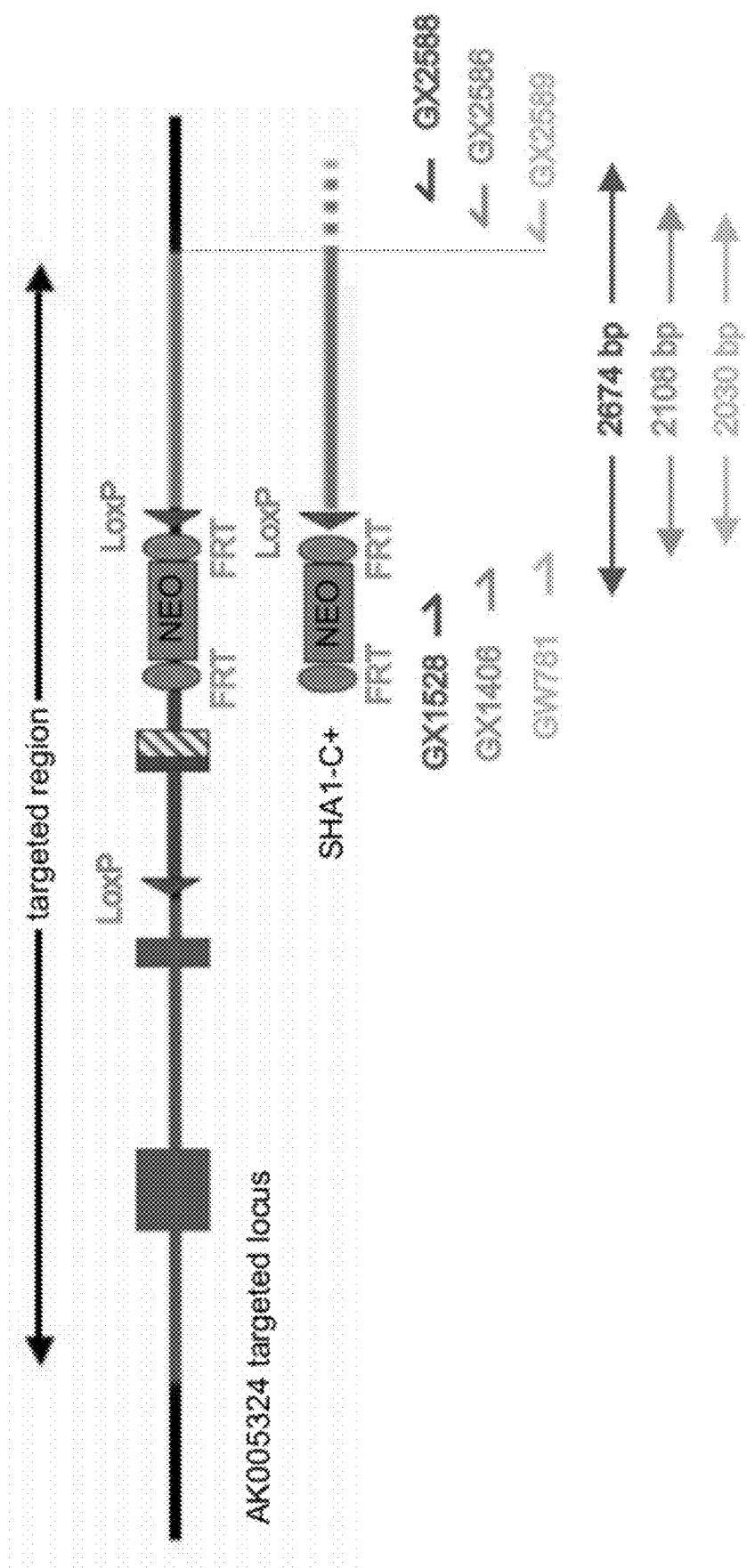

FIG. 23 is a schematic representation of a PCR screening for identification of the 3' end homologous recombination event. Half arrows illustrate the primers localization.

Figure 24:
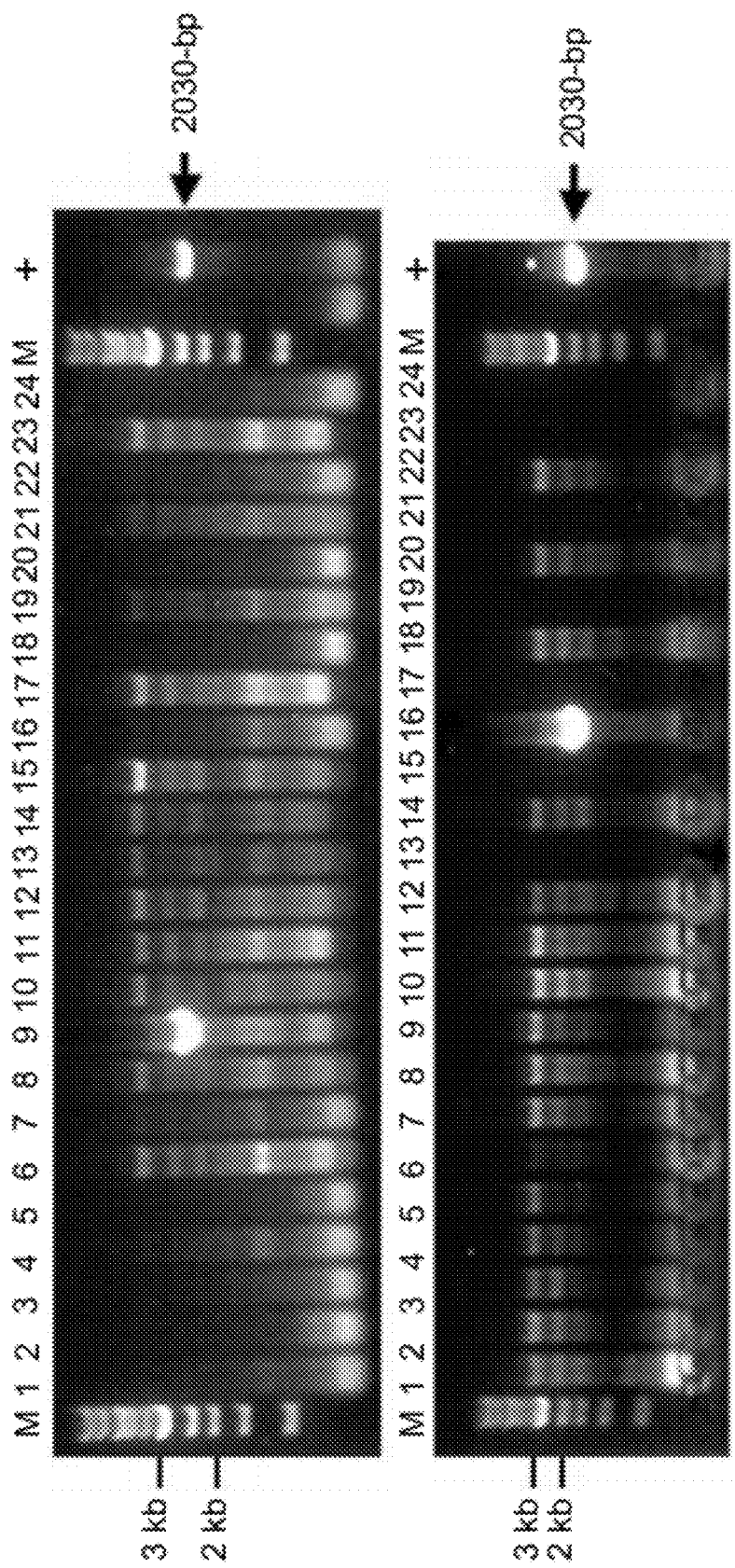

FIGS. 24A-B are photographs of representative examples of 3' PCR screening for detection of homologous recombination event. GX2589/GW781 primer set, amplicon size 2030-bp, half of the PCR reaction was loaded on the gel. Lanes M: 1 kb DNA Ladder (NEBiolabs). Lanes 1 to 24: ES cell clones. FIG. 24A: lane 9 ES clone #2A8. FIG. 24B: lane 16 ES cell clone #5A5. Lane +: positive control, ES cell clone #1B9 transfected with the SHA1-C+ positive control vector.

Figure 25:
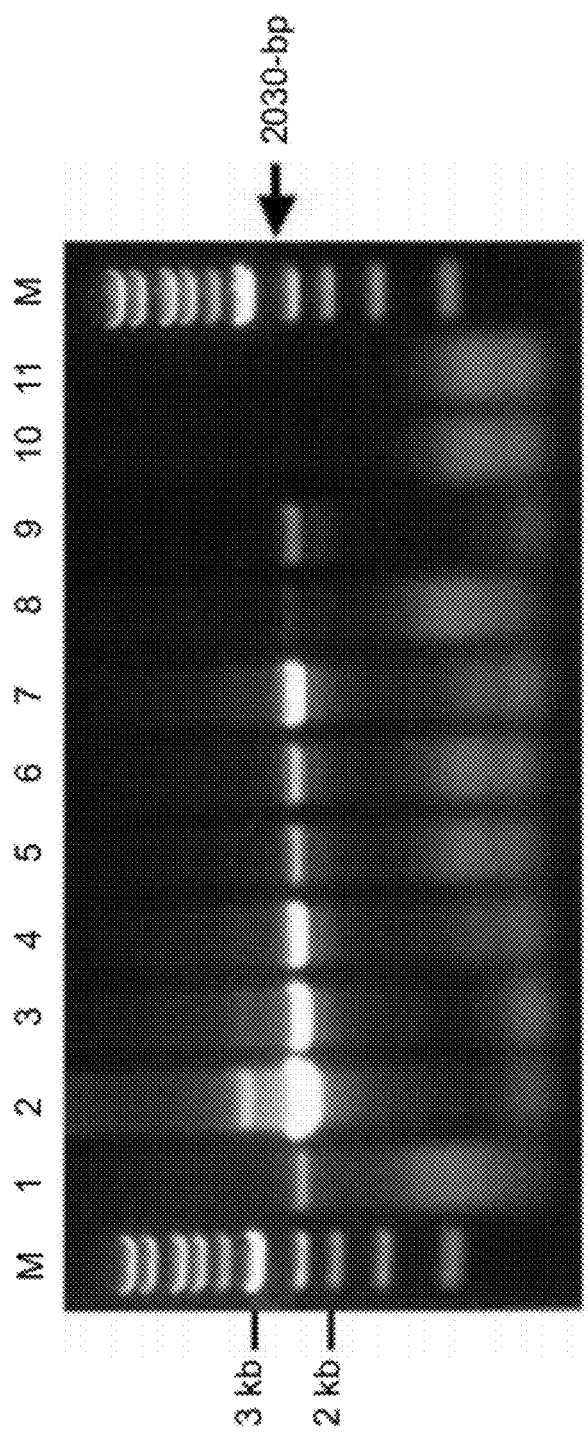

FIG. 25 is a photograph of a representative example of 3' PCR screening for detection of homologous recombination event. GX2589/GW781 primer set, amplicon size 2030-bp, half of the PCR reaction was loaded on the gel. Lanes M: 1 kb DNA Ladder (NEBiolabs). Lanes 1 to 8: ES cell clones #4A3, #5A5, #3B7, #1A11, #4A2, #1B9, #2A8, and #3B4, respectively. Lane 9: positive control, ES cell clone #1B9 transfected with the SHA1-C+ positive control vector. Lanes 10 and 11: negative control, H$_2$O.

Figure 26:
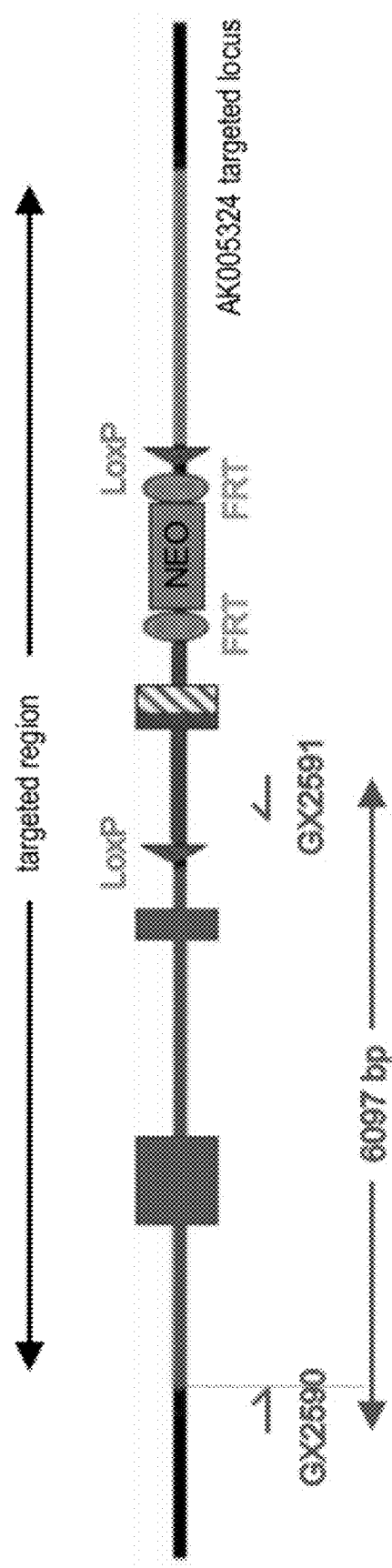

FIG. 26 is a schematic representation of a PCR screening strategy used for the detection of the distal LoxP site.

Figure 27:
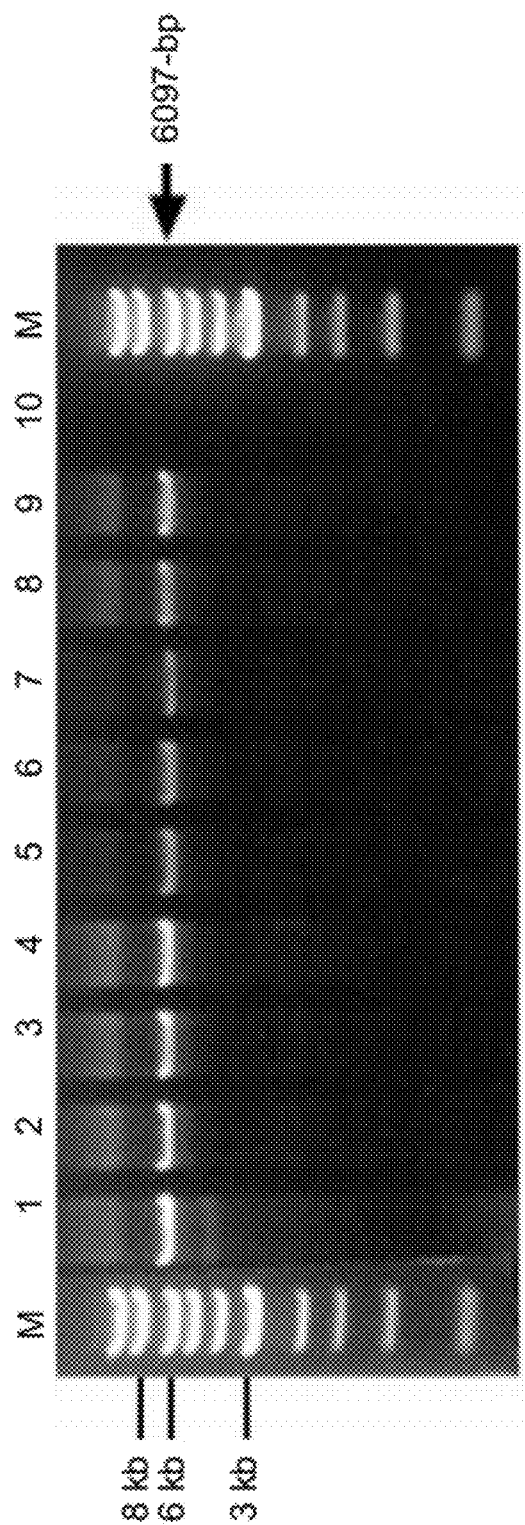

FIG. 27 is a photograph of a representative example of 5' PCR screening for detection of the distal LoxP site. GX2590/GX2591 primer set, amplicon size 6097-bp, half of the PCR reaction was loaded on the gel. Lanes M: 1 kb DNA Ladder (NEBiolabs); Lanes 1 to 8: ES cell clones #4A3, #5A5, #3B7, #1A11, #4A2, #1B9, #2A8, and #3B4, respectively; Lane 9: positive control, ES cell clone #1B9 transfected with the SHA1-C+ positive control vector and Lane 10: negative control, H$_2$O.

Figure 28A:
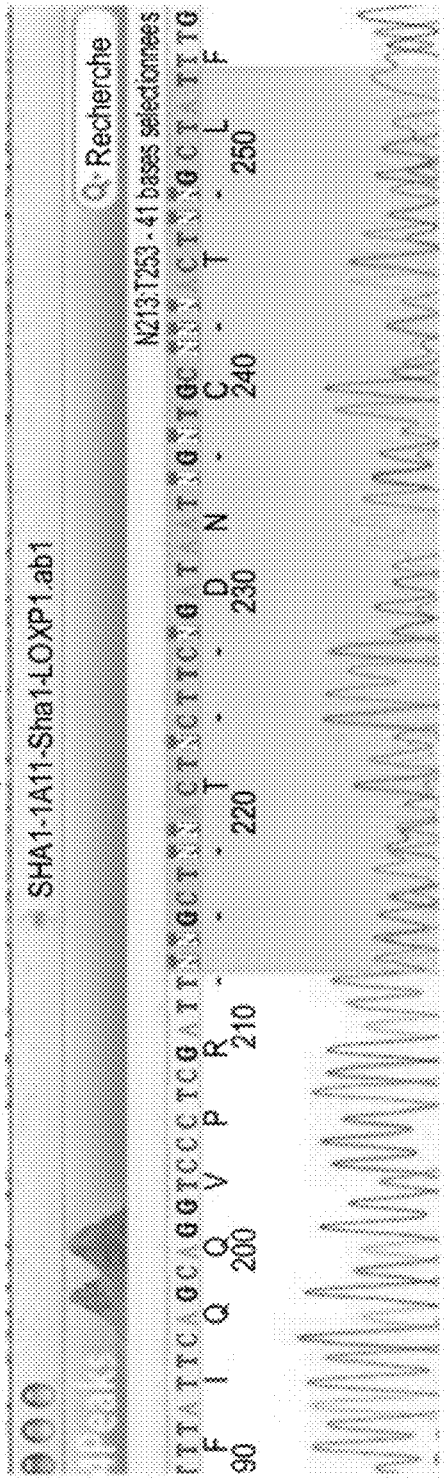
Figure 28B:
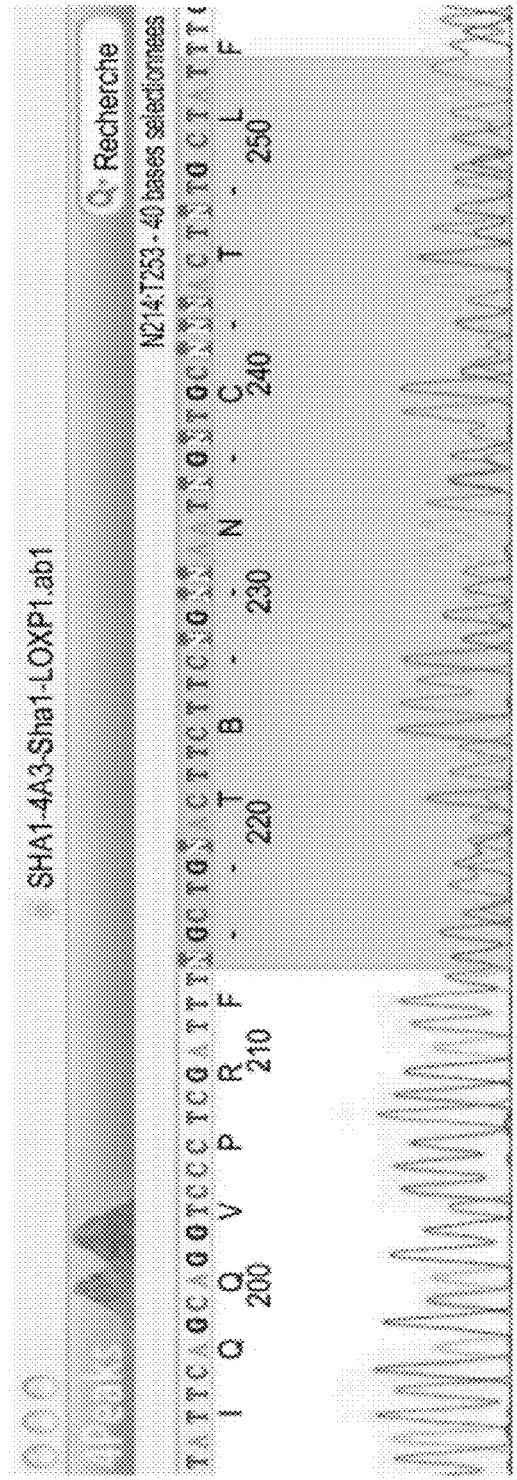

FIGS. 28A-B are electrophoregrams of a representative example obtained after sequencing of the 5' PCR product for detection of distal loxP site. FIG. 28A shows results of ES cell clone #1A11 and FIG. 28B shows results of ES cell clone #4A3.

Figure 29:
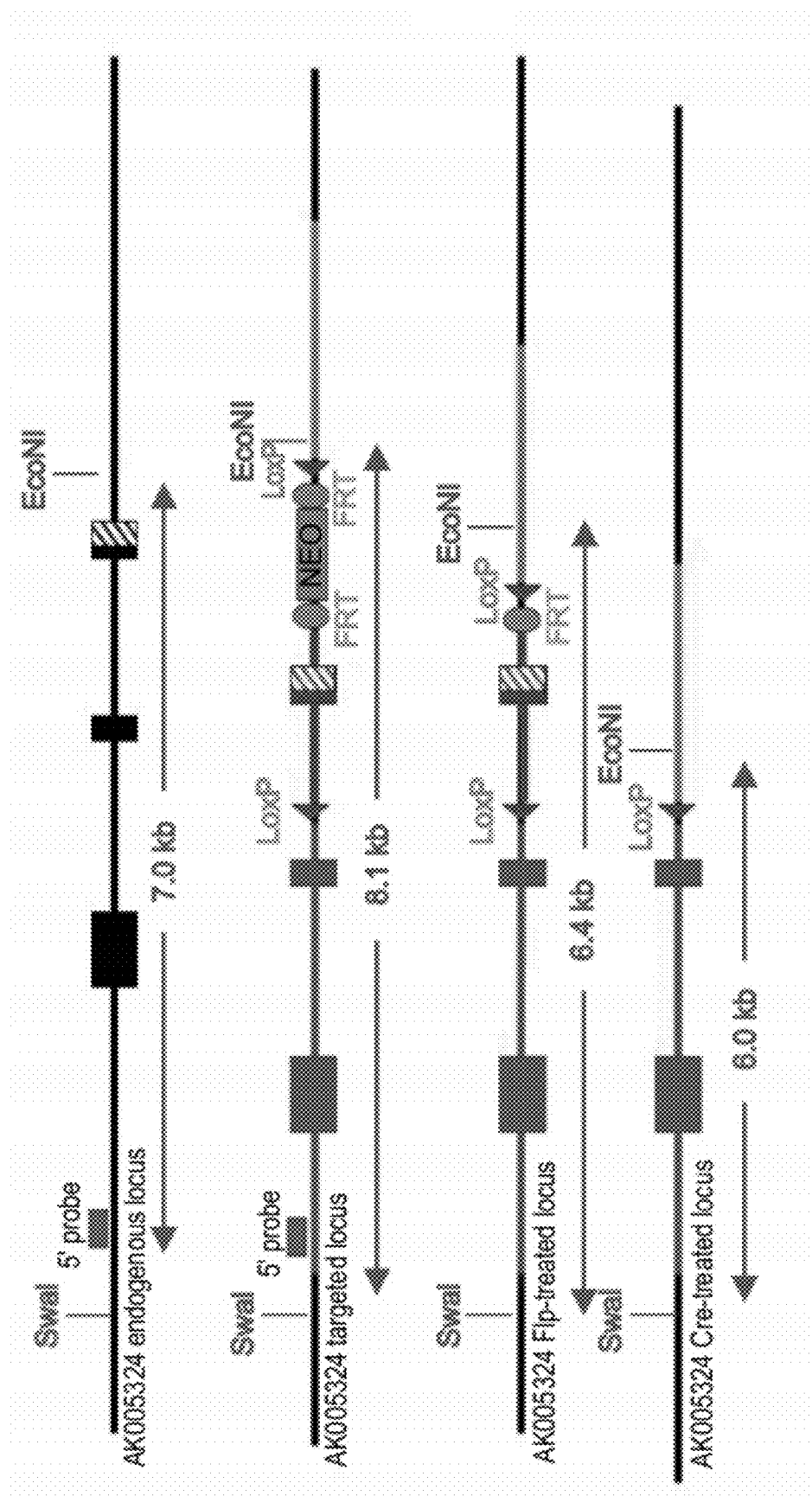

FIG. 29 is a schematic representation of the 5' Southern blot screening strategy.

Figure 30:
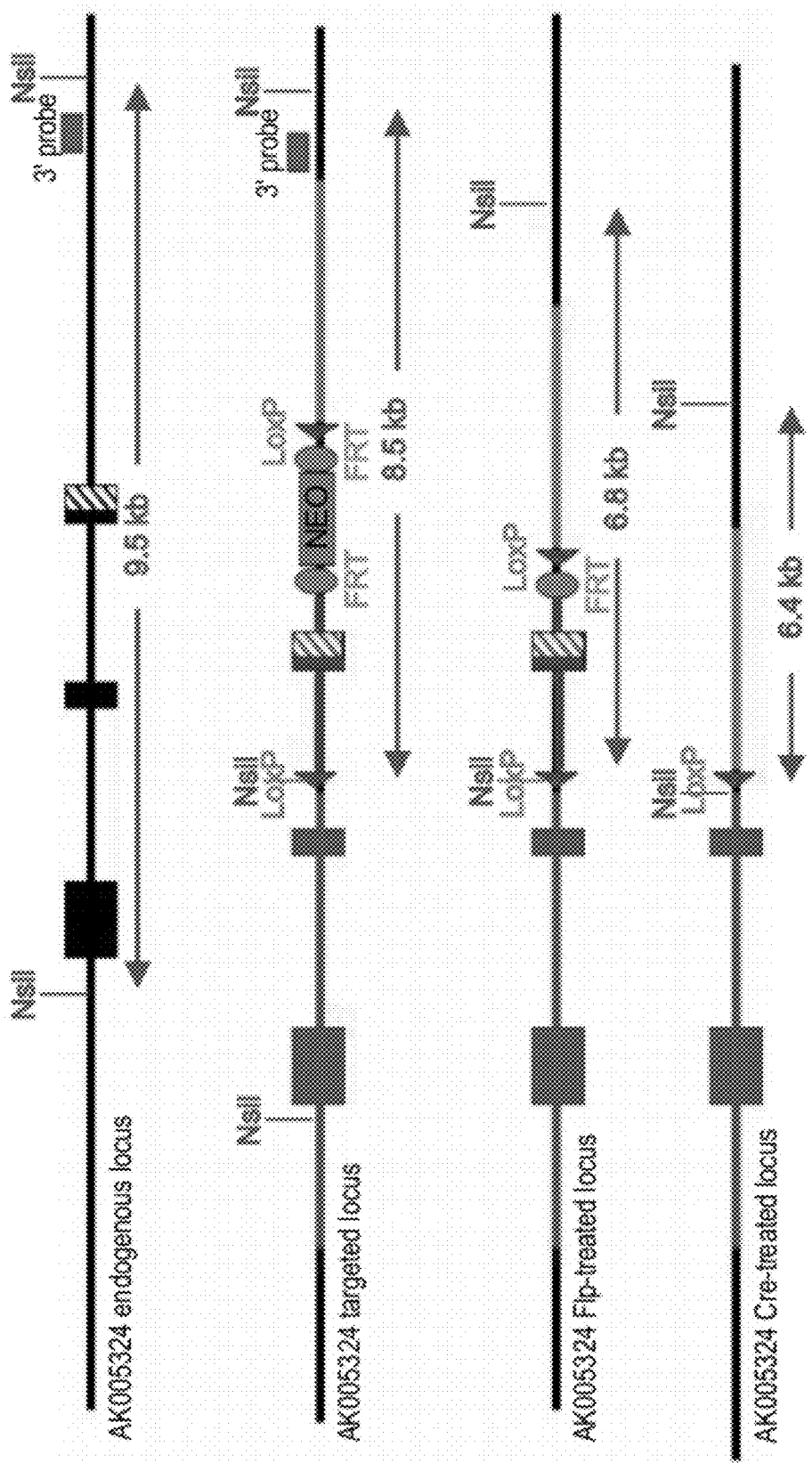

FIG. 30 is a schematic representation of the 3' Southern blot screening strategy.

Figure 31:
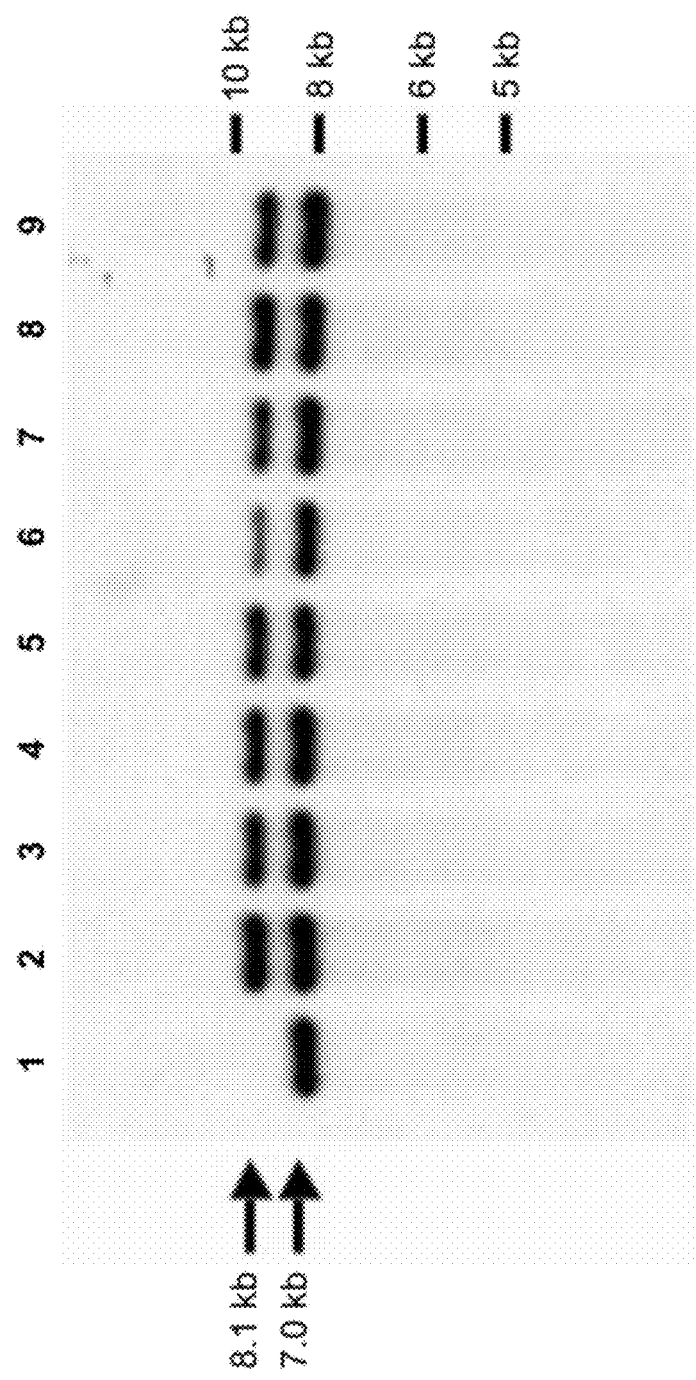

FIG. 31 is a photograph of a 5' Southern blot for the detection of homologous recombination event. Lane 1: WT ES cells. Lanes 2 to 9: ES cell clone #4A3, #5A5, #3B7, #1A11, #4A2, #1B9, #2A8, and #3B4, respectively.

Figure 32:
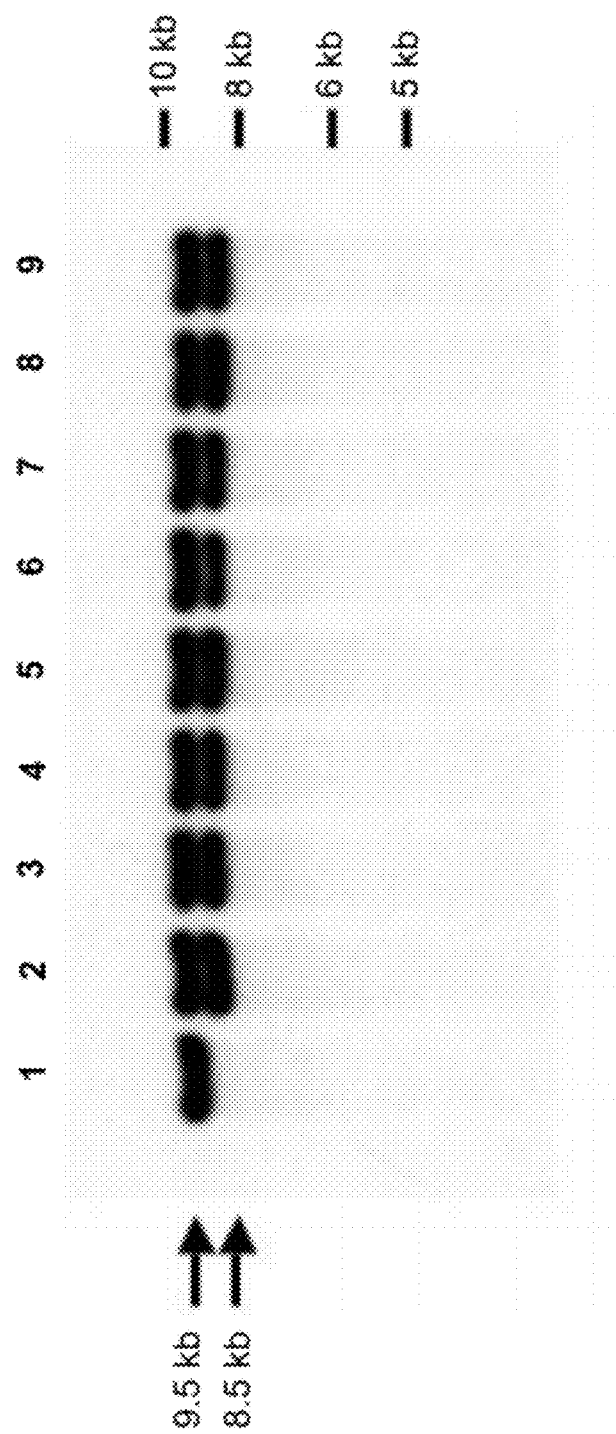

FIG. 32 is a photograph of a 3' Southern blot for the detection of homologous recombination event. Lane 1: WT ES cells. Lanes 2 to 9: ES cell clones #4A3, #5A5, #3B7, #1A11, #4A2, #1B9, #2A8, and #3B4, respectively.

Figure 33:
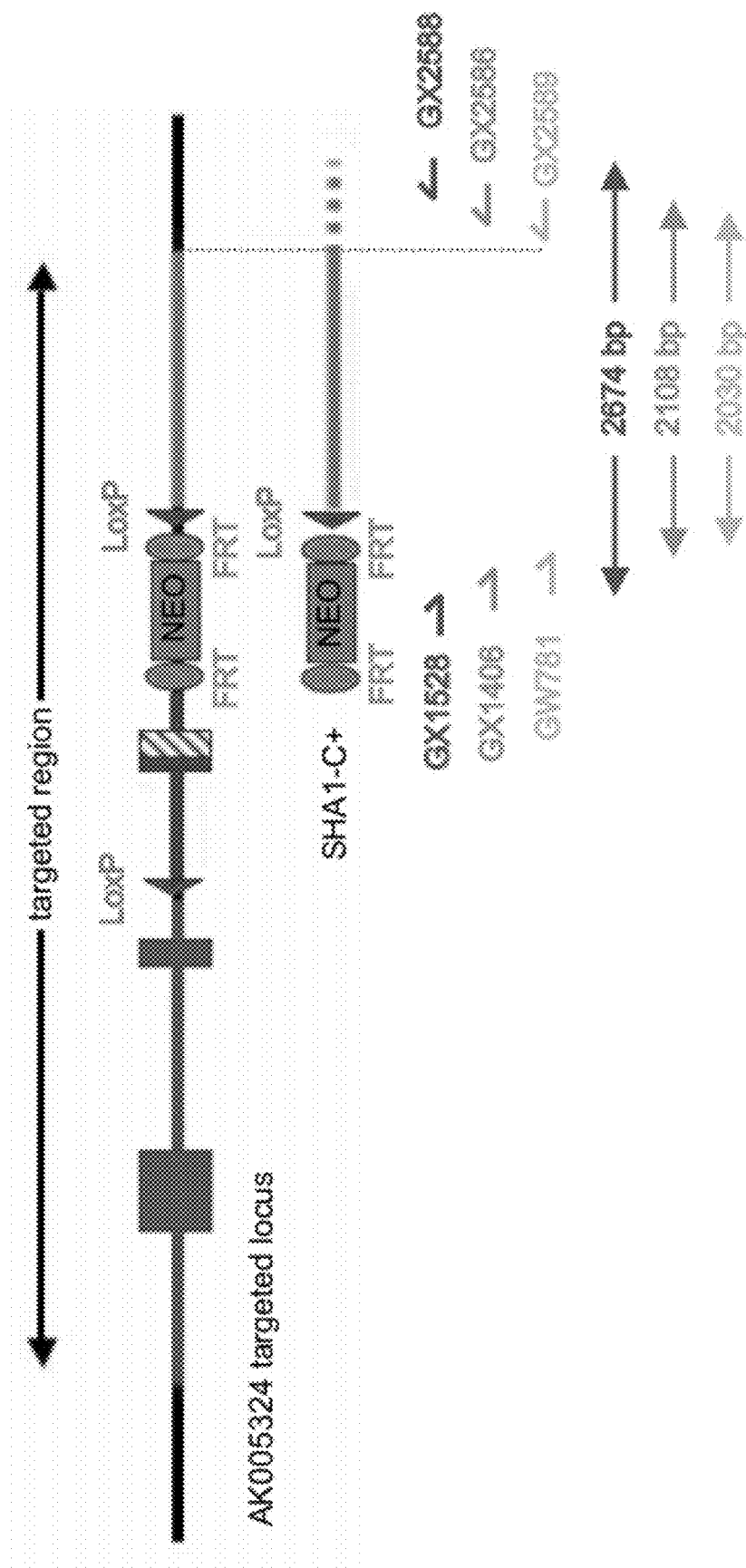

FIG. 33 is a schematic representation of a PCR screening for identification of the 3' end homologous recombination event. Half arrows illustrate the primers localization.

Figure 34:
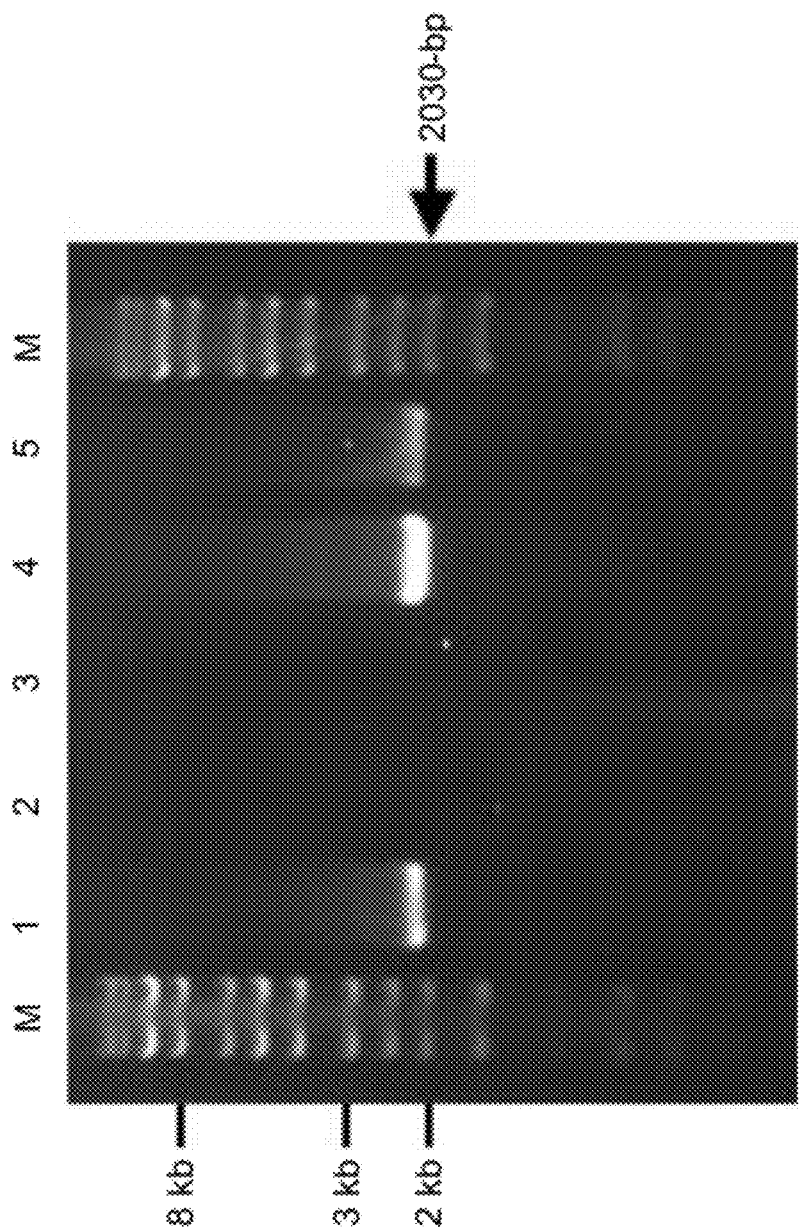

FIG. 34 is a photograph of a 3' PCR screening for the identification of F1 heterozygous animals. Lane M: UltraRanger 1-Kb DNA ladder (NorGen), Lane 1: F1 agouti mice, #34457, Lanes 2 and 3: negative control, H20 and WT tail biopsy, Lanes 4 and 5: positive control ES cell clone #3B7.

FIGS. 35A-B depict genotyping PCR of the F1 generation. FIG. 35B illustrates the genotypes of the 5 agouti pups derived from the F1 breeding were tested by PCR using the primer combination GW781/GX2589 (as illustrated in FIG. 35A) detecting the targeted AK005324 allele. One of the 5 tested animals was identified as being heterozygous for the AK005324 deletion. PCR using DNA from the targeted ES clone #3B7 was used as positive control. PCR without template served as a negative control. M: 1 kb DNA-Ladder (NEB)

Figures 36A, 36B:
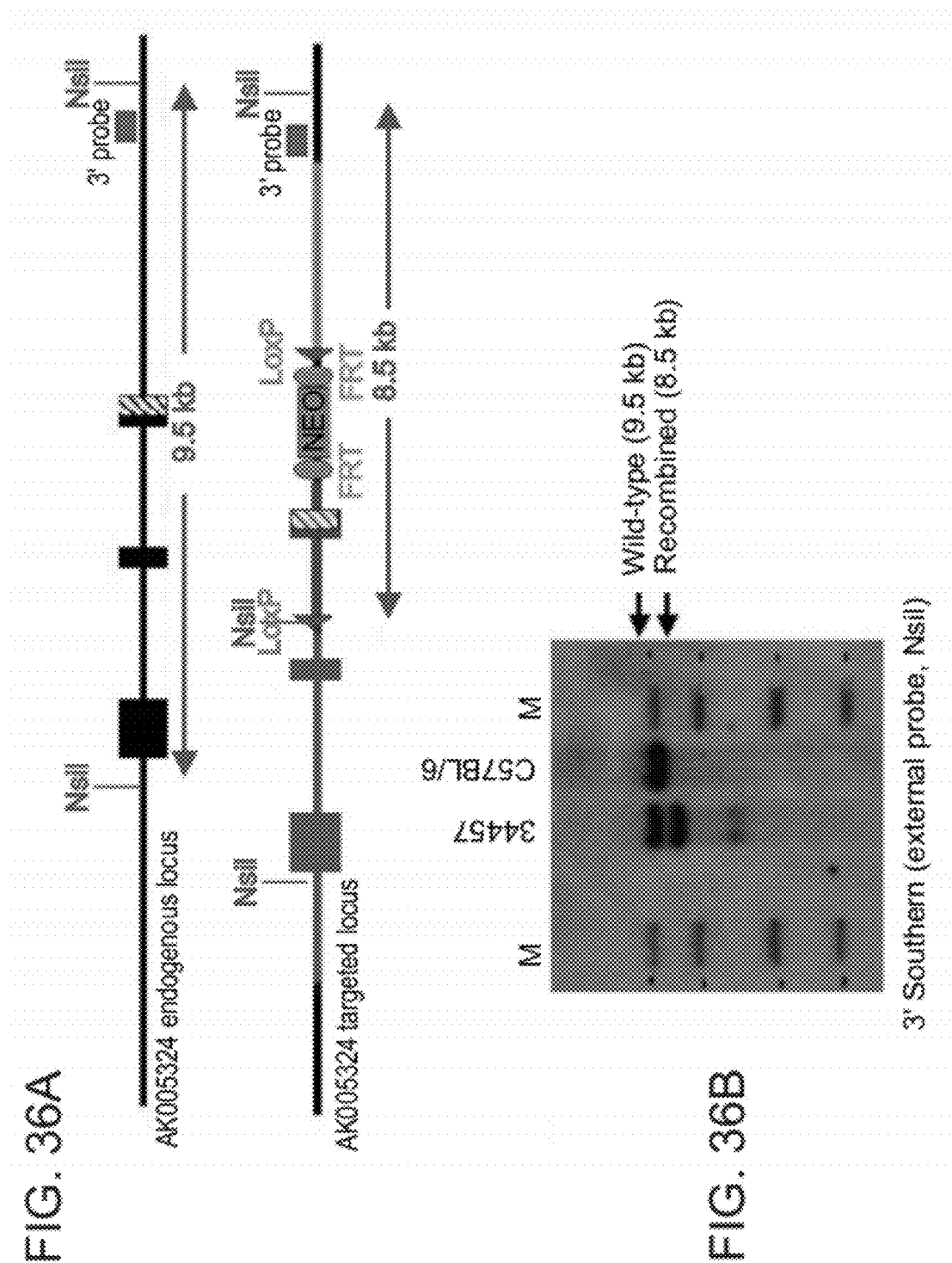

FIGS. 36A-B depict southern blot analysis of the F1 generation. FIG. 36A is a schematic illustration. FIG. 36B shows the genomic DNA of the tested F1 mouse (#34457) as compared with wild-type DNA (C57BL/6). The NsiI digested DNAs were blotted on nylon membrane and hybridized with the 3' probe to validate the genotype of the Ak005324 locus in these animals.

Figure 37A:
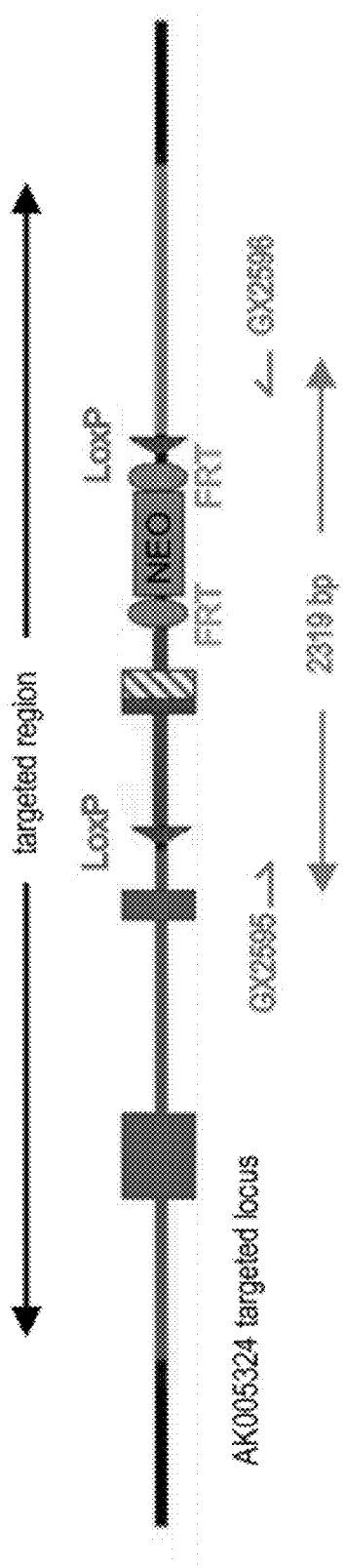
Figure 37B:
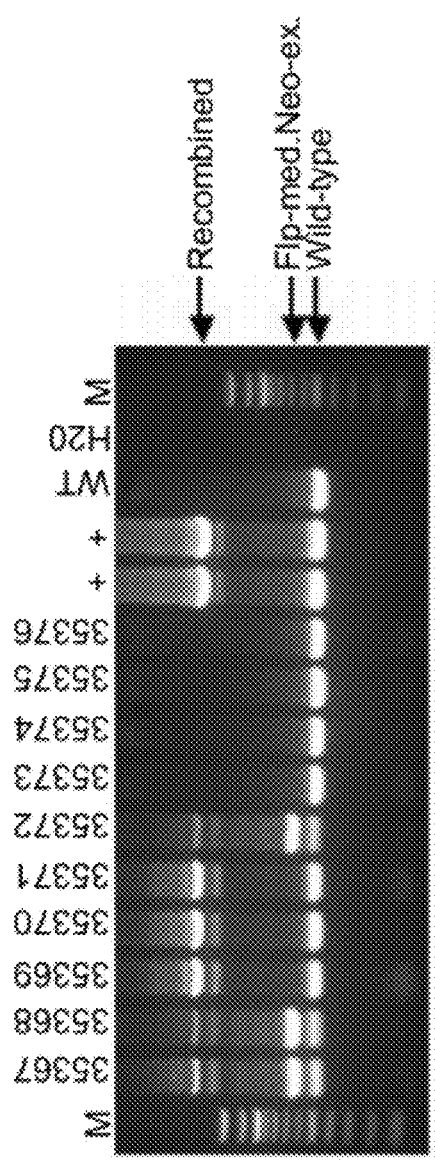

FIGS. 37A-B depict detection of the Flp-mediated excision event by PCR. T FIG. 37A is a schematic illustration. FIG. 37B shows the genotypes of the 10 agouti pups derived from the F1 breeding with Flp deleter mice were tested by PCR using the primer combination GX2595/GX2596 to analyze the excision status of the AK005324 allele. PCR using DNA from the targeted ES clone #3B7 and wild-type ES cells was used as positive control. PCR without template served as a negative control. M: 1 kb DNA-Ladder (NEB).

FIGS. 38A-B depict detection of the non-excised targeted allele by PCR. FIG. 38A is a schematic illustration. FIG. 38B shows the genotypes of the 10 agouti pups derived from the F1 breeding with Flp deleter mice were tested by PCR using the primer combination GW781/GX2589 to analyze the presence of the neomycin cassette. PCR using DNA from the targeted ES clone #3B7 and wild-type ES cells was used as positive and negative controls, respectively. PCR without template served as a negative control. M: 1 kb DNA-Ladder (NEB).

FIGS. 39A-B is a southern blot analysis of the F1 generation bred with Flp deleter mice. FIG. 39A is a schematic illustration. FIG. 39B shows the genomic DNA of the tested F1 mouse (#34457, #35367, #35368 and #35372) was compared with wild-type DNA (C57BL/6). The NsiI digested DNAs were blotted on nylon membrane and hybridized with the 3' probe to validate the deletion status of the Ak005324 targeted allele.

Figure 40A:
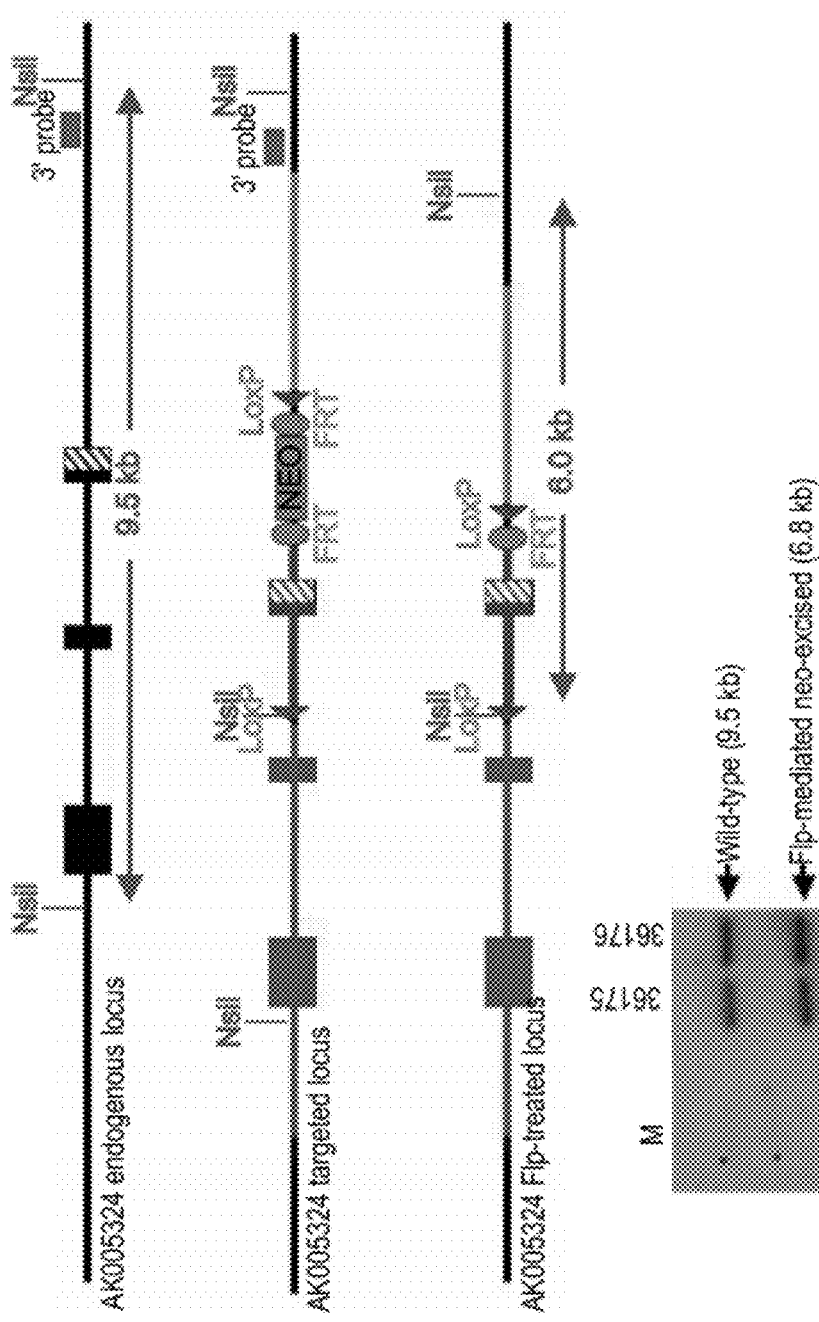
Figure 40B:
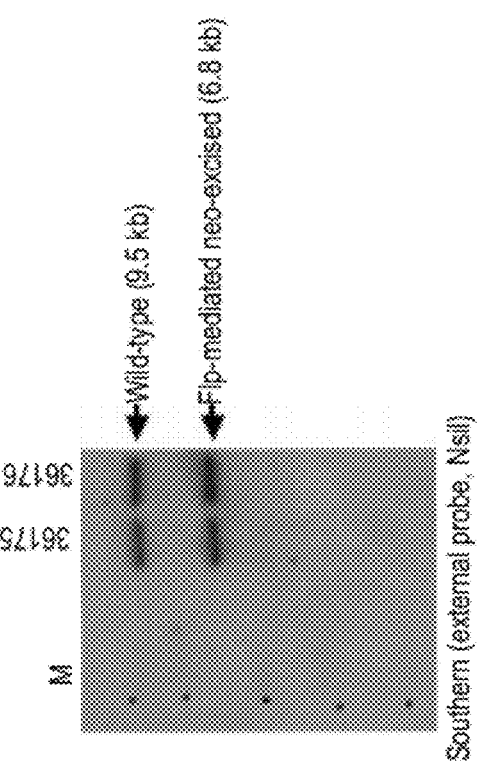

FIGS. 40A-B are southern blot analysis of the F1 generation. FIG. 40A is a schematic illustration. FIG. 40B shows the genomic DNA of the 2 tested F1 mice (#36175 and #36176) were compared with wild-type DNA (129ES, BL6). The NsiI digested DNAs were blotted on nylon membrane and hybridized with the 3' probe to validate the zygocity of the AK005324 gene mutation in these animals.

Figure 41A:
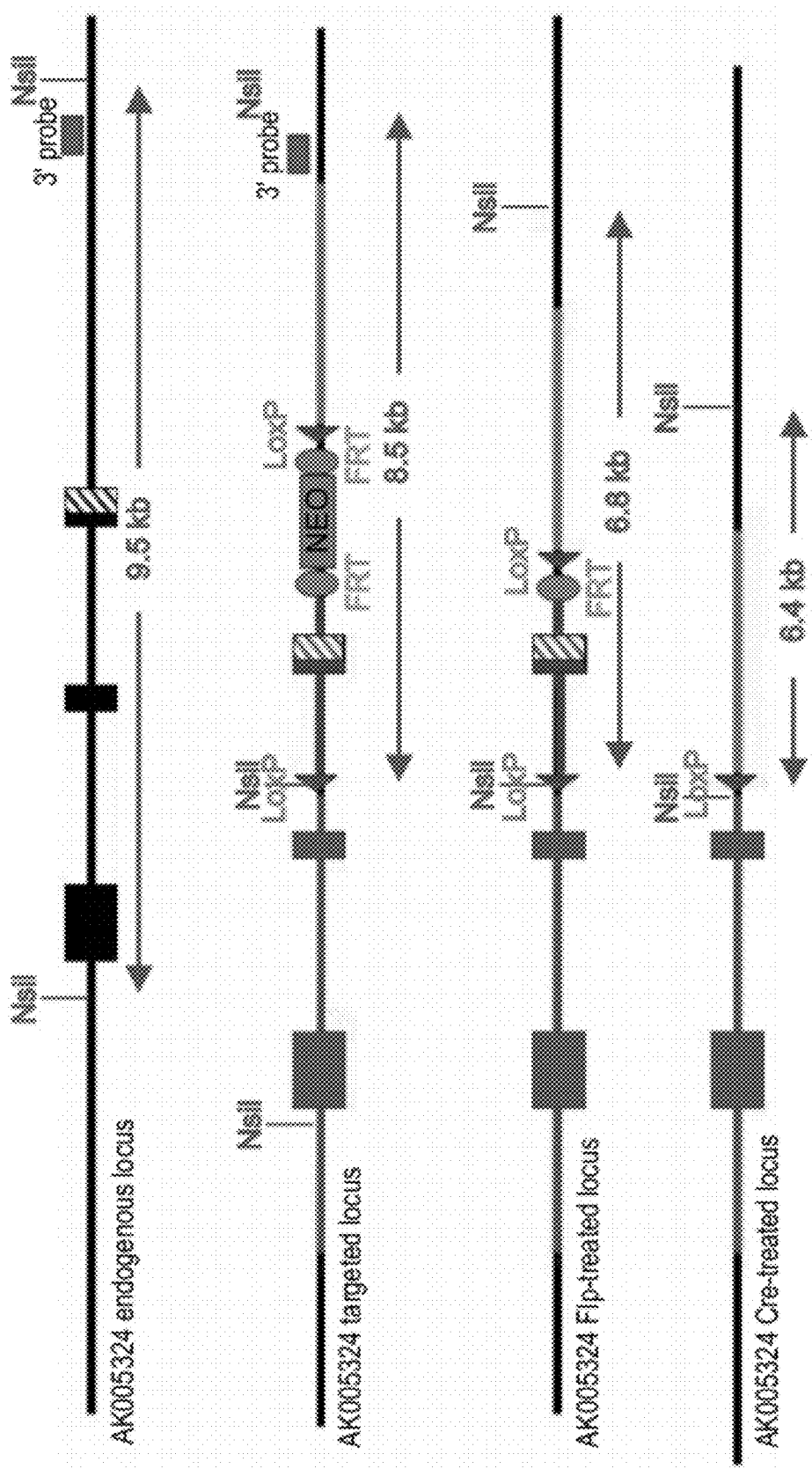
Figure 41B:
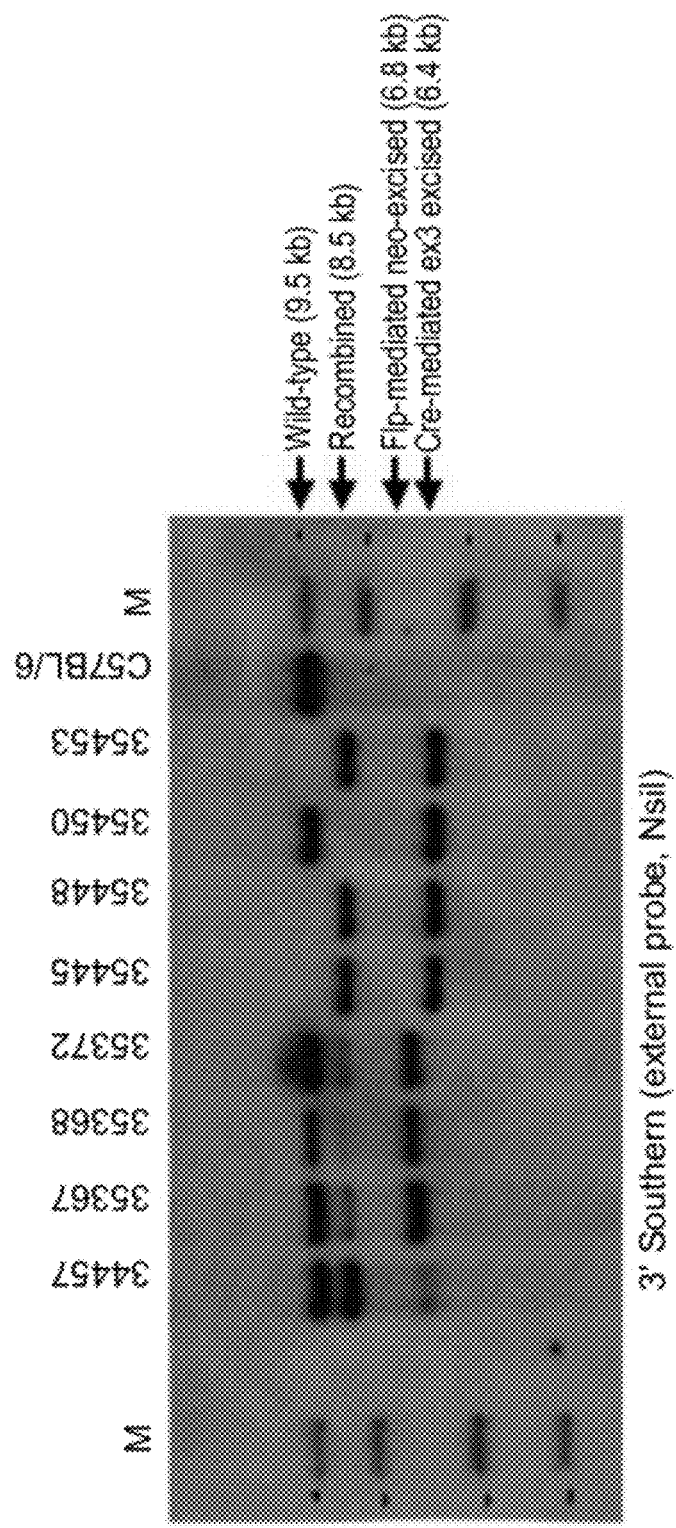

FIGS. 41A-B are southern blot analysis of the F1 generation. FIG. 41A is a schematic illustration. FIG. 41B shows the genomic DNA of the 8 tested F1 mice (#34457, #35367, #35368, #35372, #35445, #35448, #35450 and #35453) were compared with wild-type DNA (129ES, BL6). The NsiI digested DNAs were blotted on nylon membrane and hybridized with the 3' probe) to validate the deletion status of the AK005324 allele.

Figure 42A:
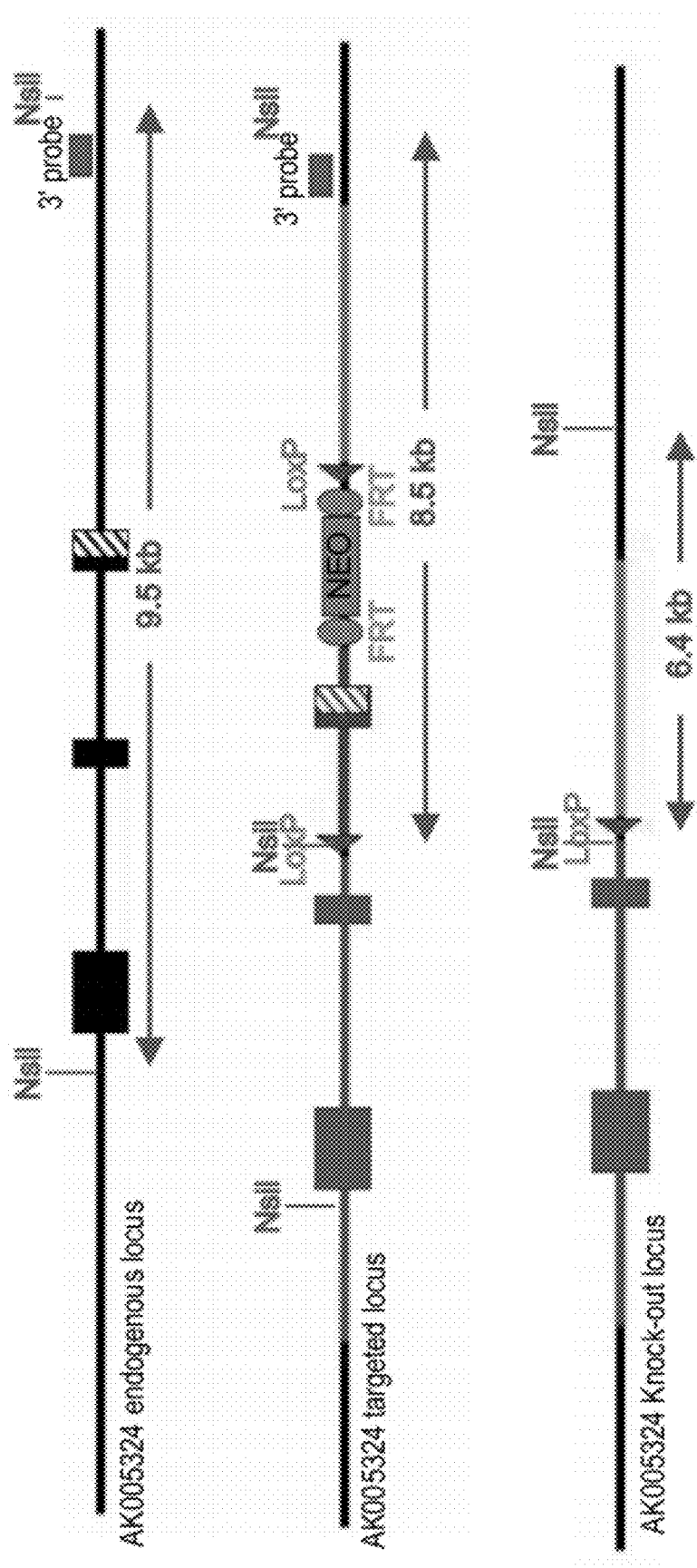
Figure 42B:
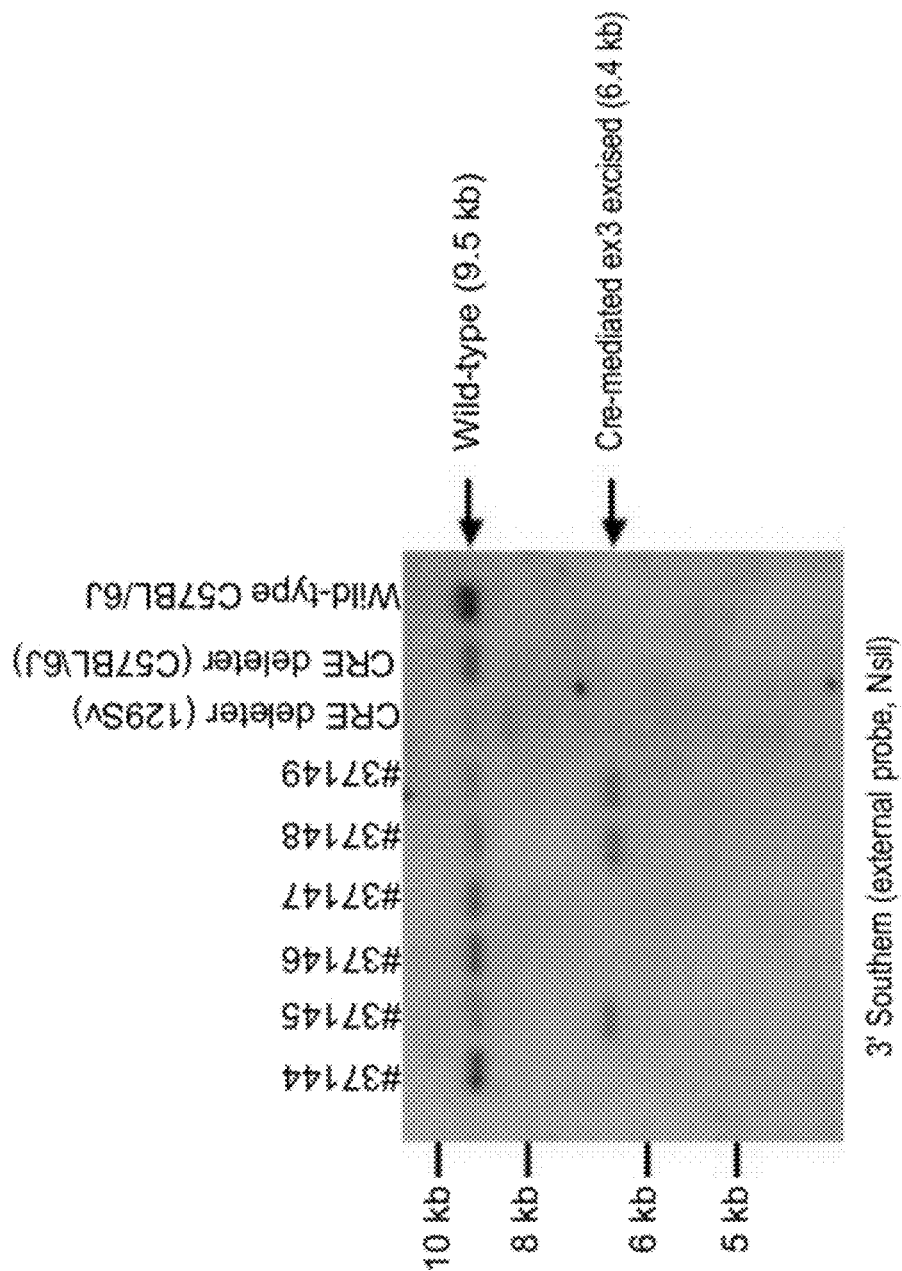

FIGS. 42A-B are Southern blot analysis of the AK005324 Knock-out mice.

FIG. 42A is a schematic illustration. FIG. 42B shows the genomic DNA of the 6 tested F1 mice (#37144, #37145, #37146, #37147, #37148 and #37149) were compared with wild-type (C57BL/6) and Cre deleter (C57BL/6 and 129Sv) DNA. The NsiI digested DNAs were blotted on nylon membrane and hybridized with the 3' probe to validate the excision status of the AK005324 allele.

Figure 43A:
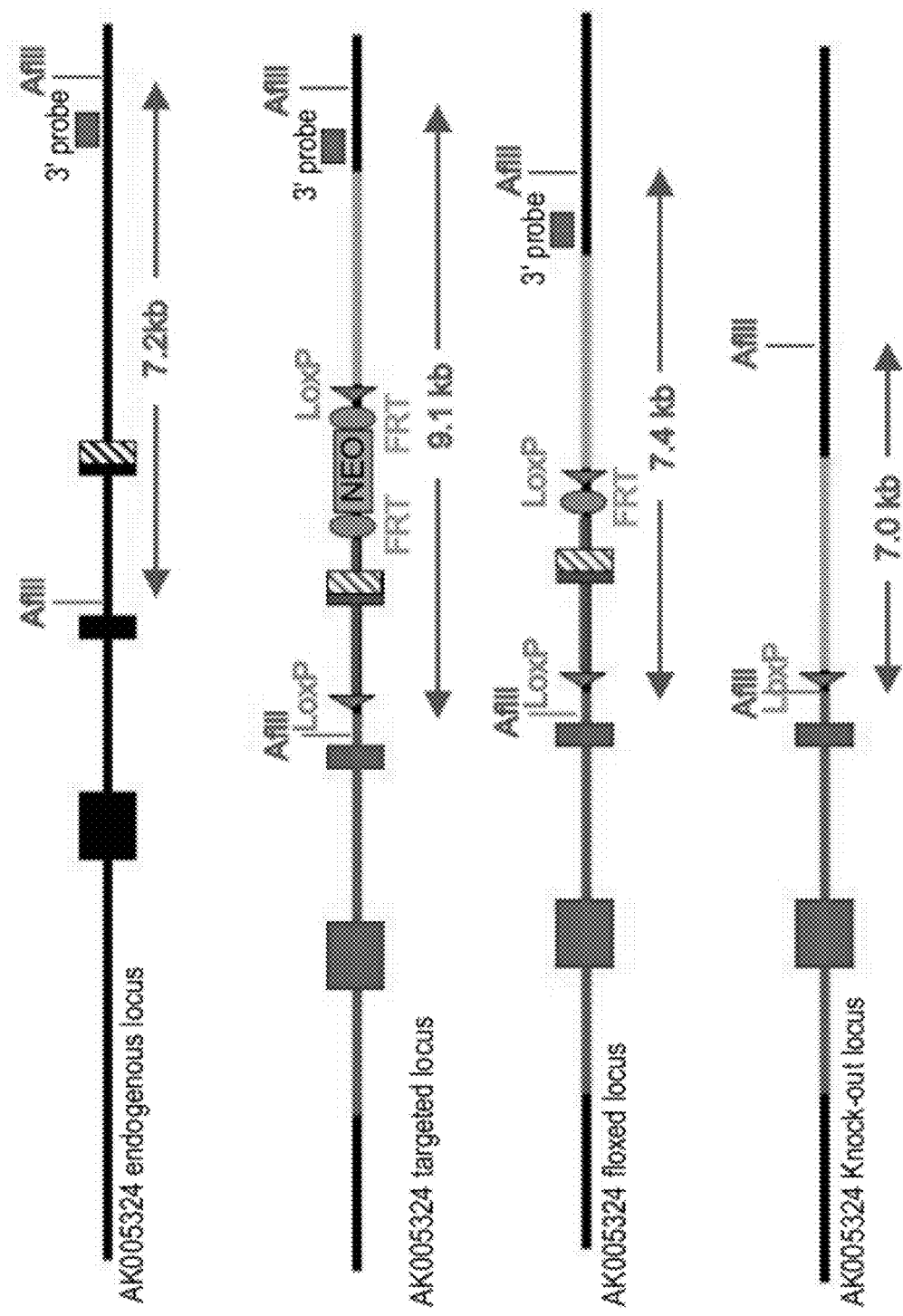
Figure 43B:
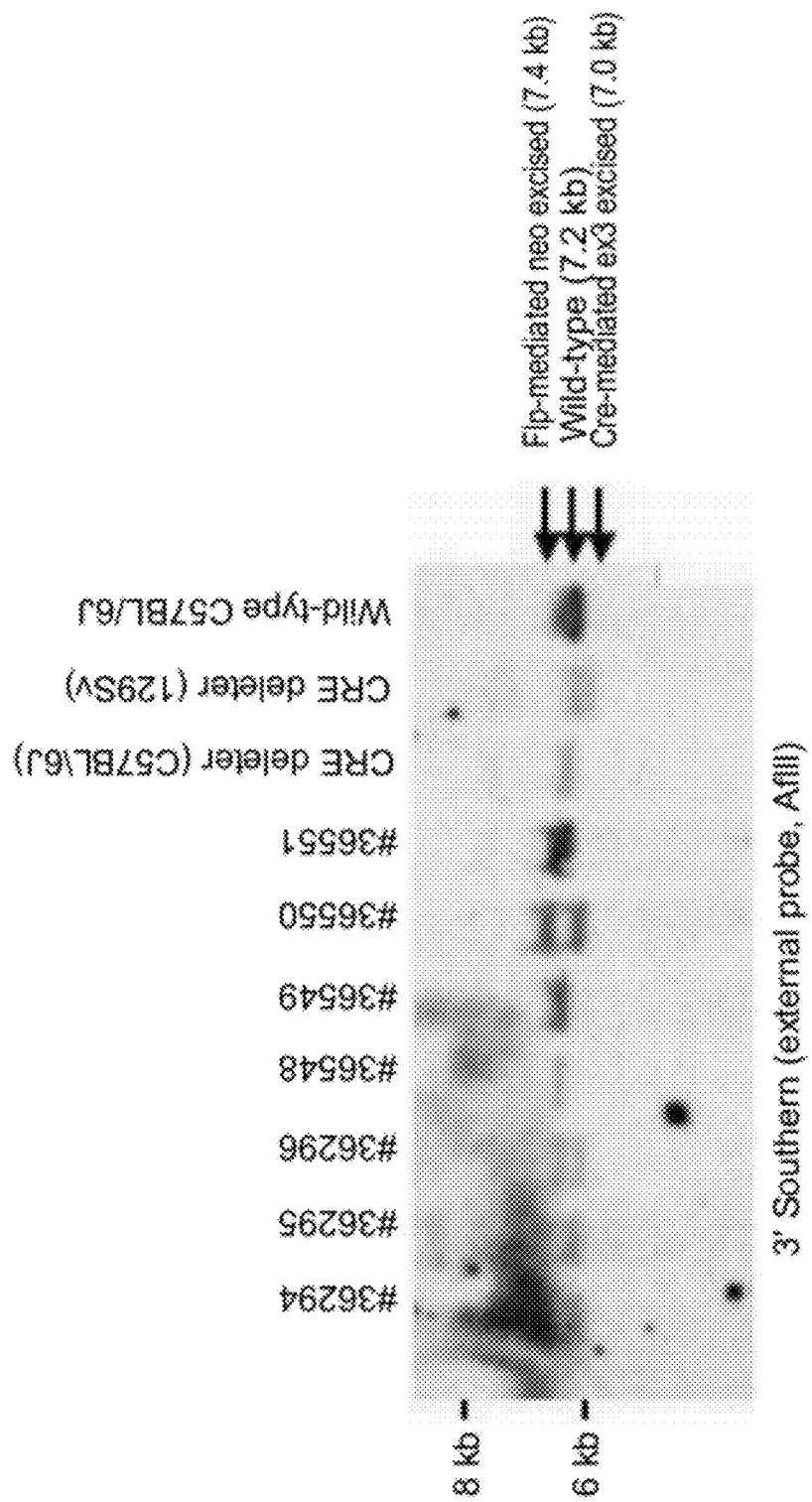

FIGS. 43A-B are Southern blot analysis of the AK005324 Knock-out mice. FIG. 43A is a schematic illustration. FIG. 43B shows the genomic DNA of the 7 tested F1 mice (#36294, #36295, #36296, #36548, #36549, #36550 and #35551) were compared with wild-type (C57BL/6) and Cre deleter (C57BL/6 and 129Sv) DNA. The AflII digested DNAs were blotted on nylon membrane and hybridized with the 3' probe to validate the zygocity of the AK005324 gene mutation in these animals.

Figure 44:
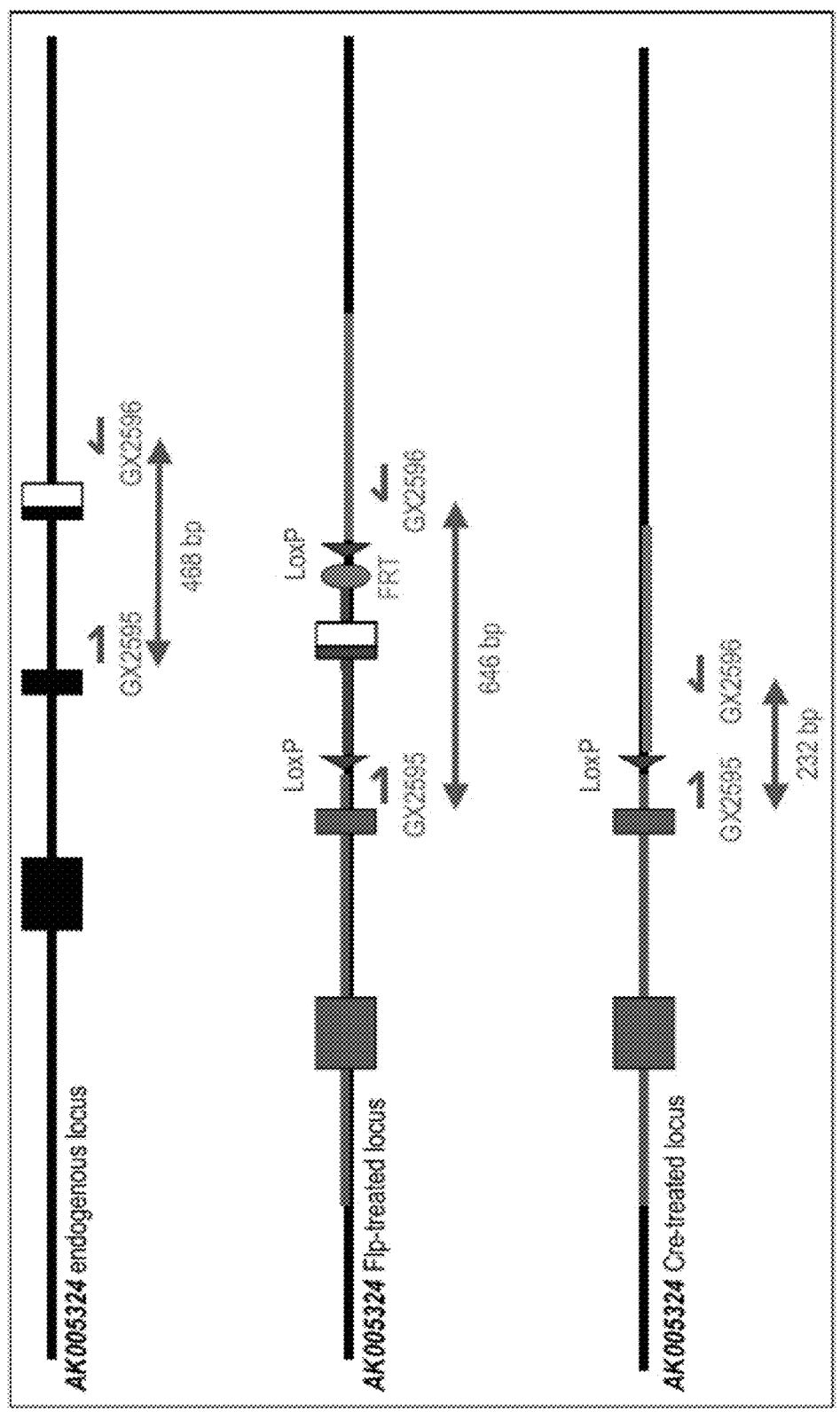

FIG. 44 is schematic representation of the AK005324 alleles with the binding sites of the screening primers is shown. PCR genotyping of the AK005324 conditional and knock-out mouse line.

Figures 45A, 45B:
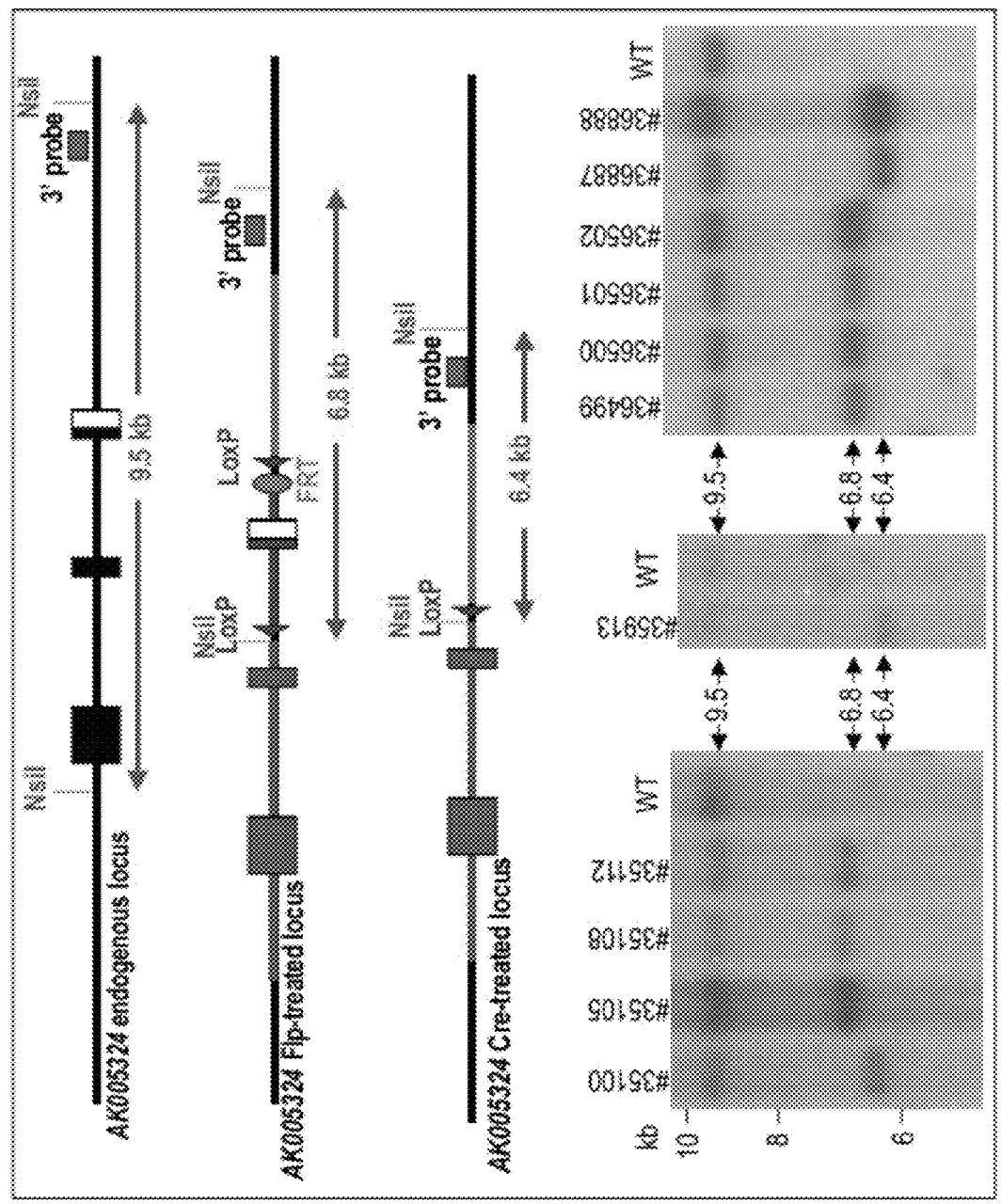

FIGS. 45A-B are southern blot analysis of the N2 generation. FIG. 45A shows schematic representation of the southern blot strategy used to confirm the genotype of F2 animals; and FIG. 45B shows results of the Southern Blot analysis of tested F2 animals. The genomic DNA of the tested mice was compared with C57BL/6 wild-type DNA (WT). The NsiI digested DNA was blotted on nylon membrane and hybridised with the external 3' probe.

Figures 46A, 46B:
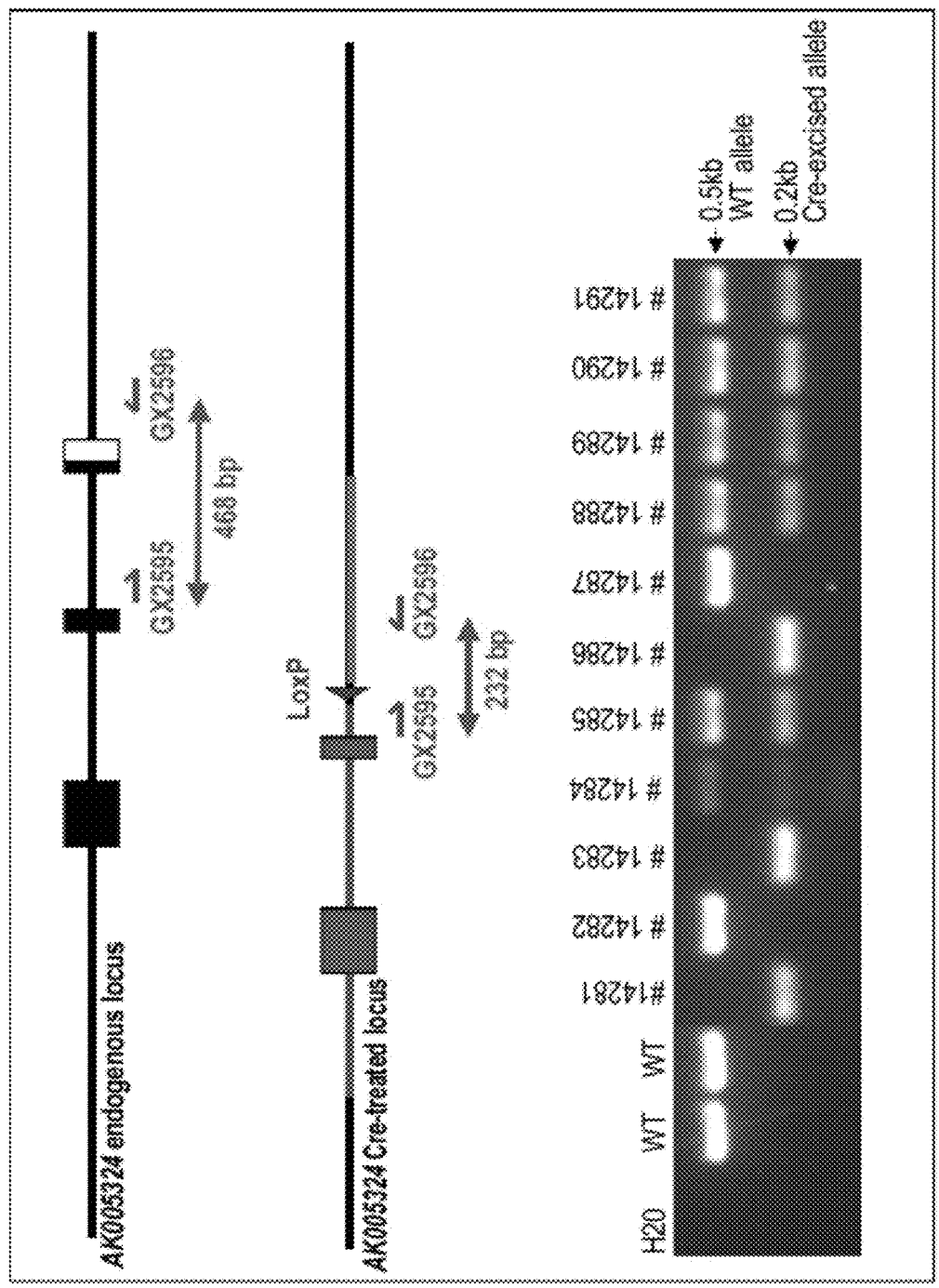

FIGS. 46A-B are PCR genotyping of the F2 generation. An example of the genotyping of the pups derived from the F2 breeding tested by PCR using the primer combination GX2595/GX2596 detecting the Knock-out AK005324 allele. 3 of the 11 tested animals were identified as being homozygous for the Knock-out AK005324 allele. PCR using wild-type DNA was used as positive control. M: 1 kb DNA-Ladder (NEB).

FIGS. 47A-B are southern blot analysis of the F2 generation. FIG. 47A is a schematic illustration. FIG. 47B shows southern blot analysis of the F2 generation. An example of the genomic DNA of the tested F2 mice was compared with wild-type DNA. The NsiI digested DNAs were blotted on nylon membrane and hybridised with the 3' probe to validate the zygocity of the Knock-out AK005324 allele in these animals.

Figures 48A, 48B:
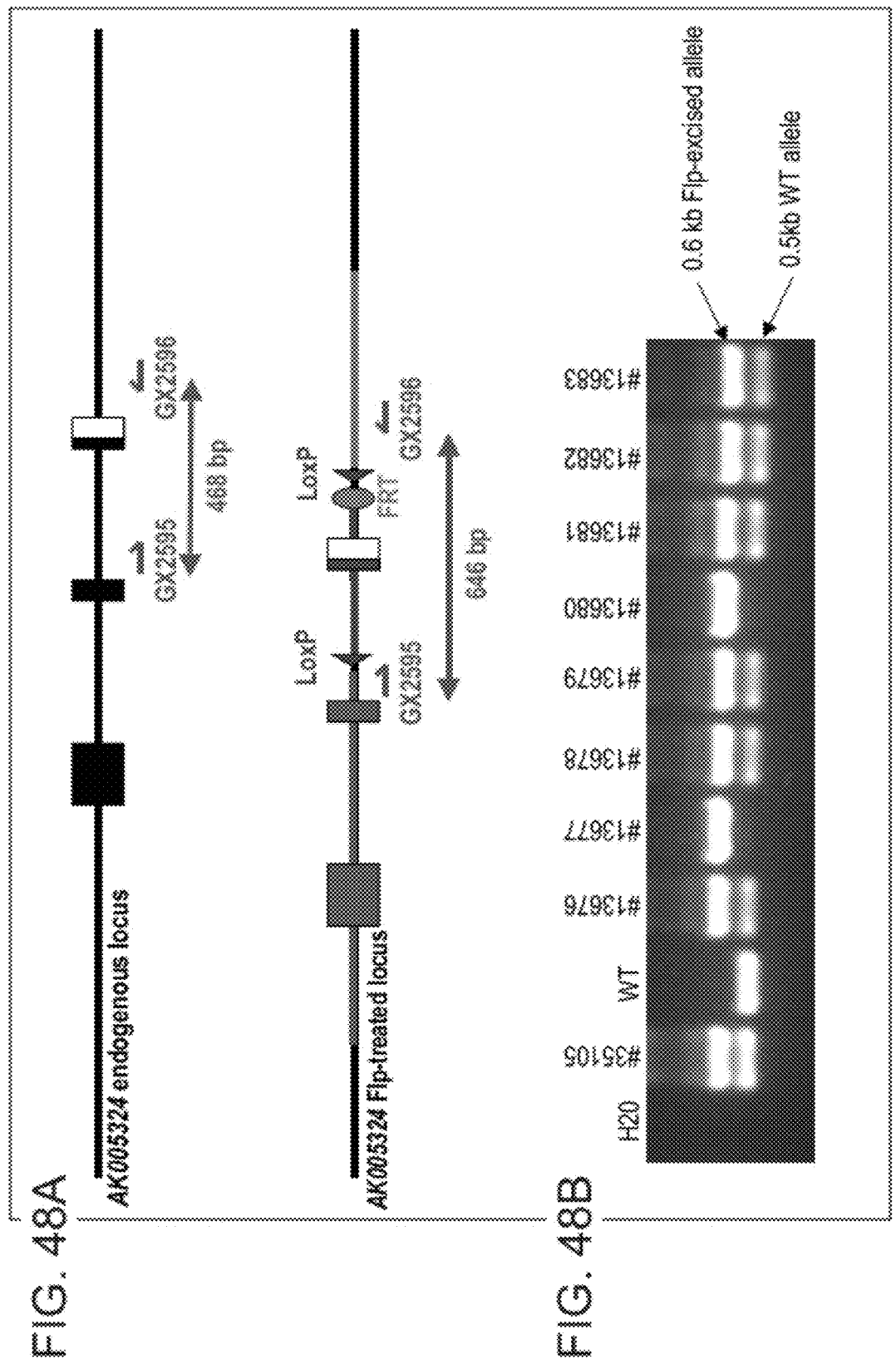

FIGS. 48A-B are PCR genotyping of the F2 generation. PCR genotyping of the F2 generation. FIG. 48A is a schematic illustration. FIG. 48B shows an example of the genotyping of the pups derived from the F2 breeding tested by PCR using the primer combination GX2595/GX2596 detecting the Knock-out AK005324 allele. 4 of the 11 tested animals were identified as being homozygous for the Knock-out AK005324 allele. PCR using wild-type DNA (C57) was used as positive control. M: 1 kb DNA-Ladder (NEB).

Figures 49A, 49B:
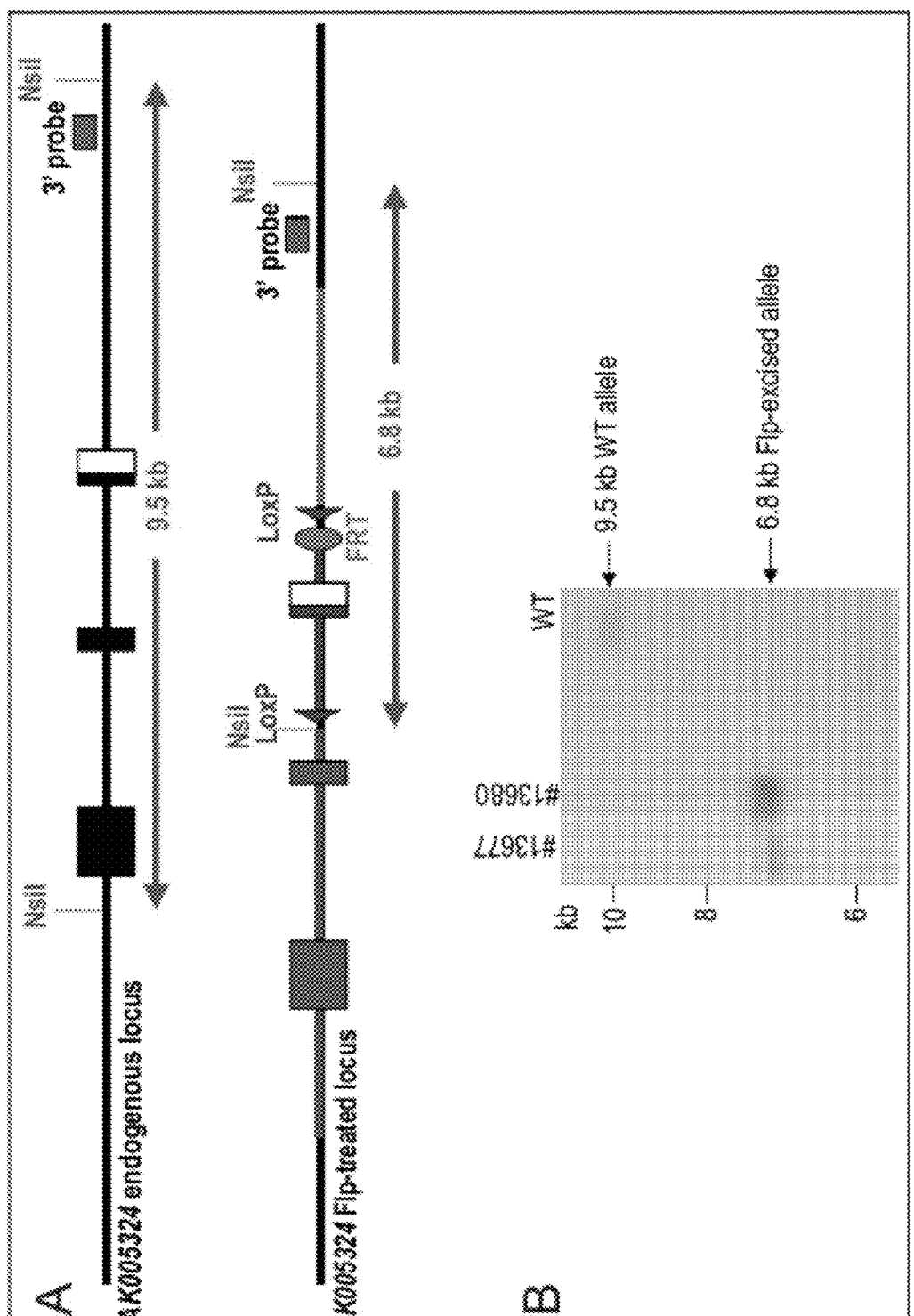

FIGS. 49A-B are Southern blot analysis of the F2 generation. FIG. 49A is a schematic illustration. FIG. 49B shows an example of the genomic DNA of the tested F2 mice was compared with wild-type DNA. The NsiI digested DNAs were blotted on nylon membrane and hybridized with the 3' probe to validate the zygocity of the floxed Knock-out AK005324 allele in these animals.

Figure 50A:
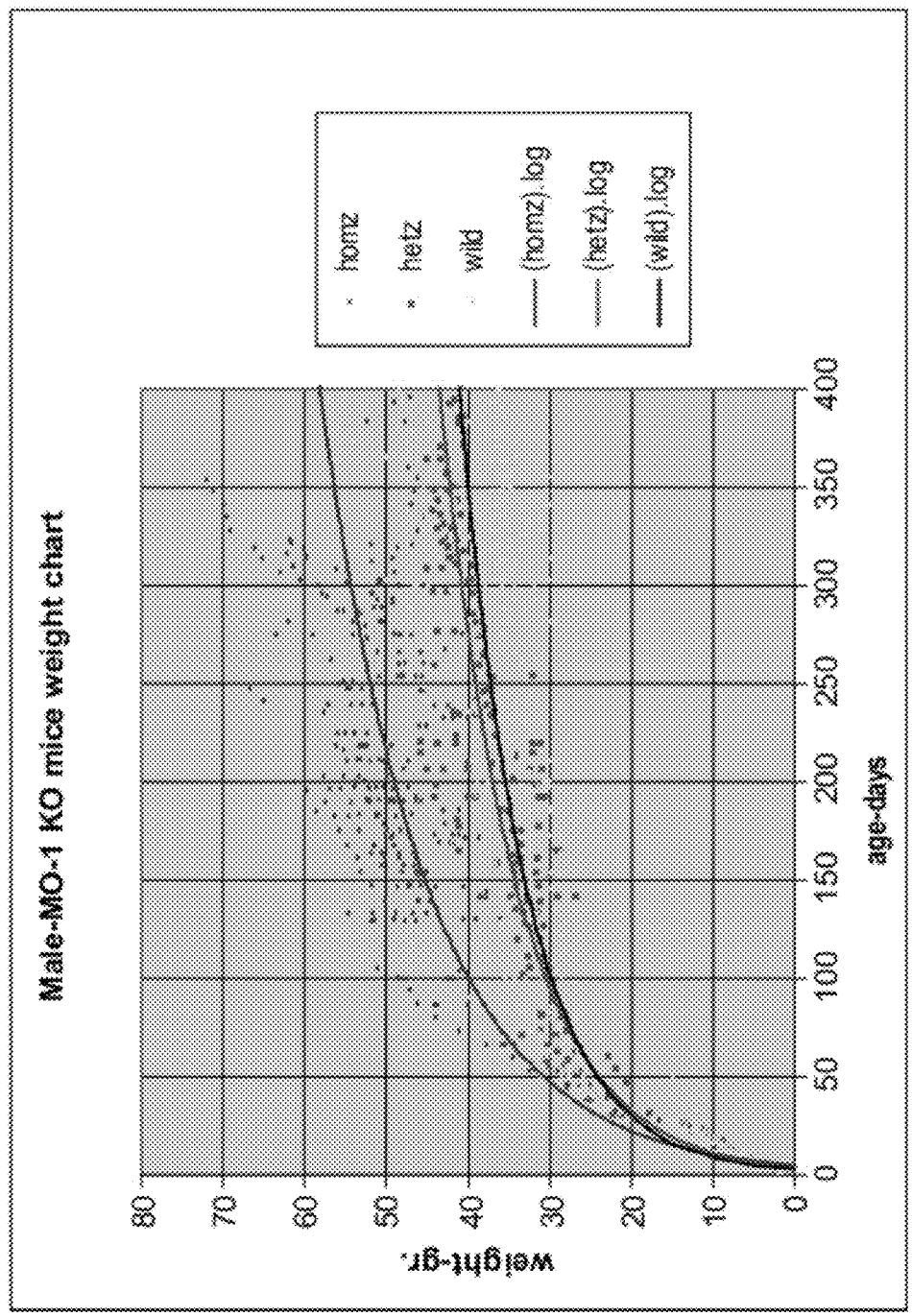

FIG. 50A is a graph depicting male MO-1-KO mice weight chart from birth to 400 days. Male MO-1-KO mice weight chart from birth to 400 days.

Figure 50B:
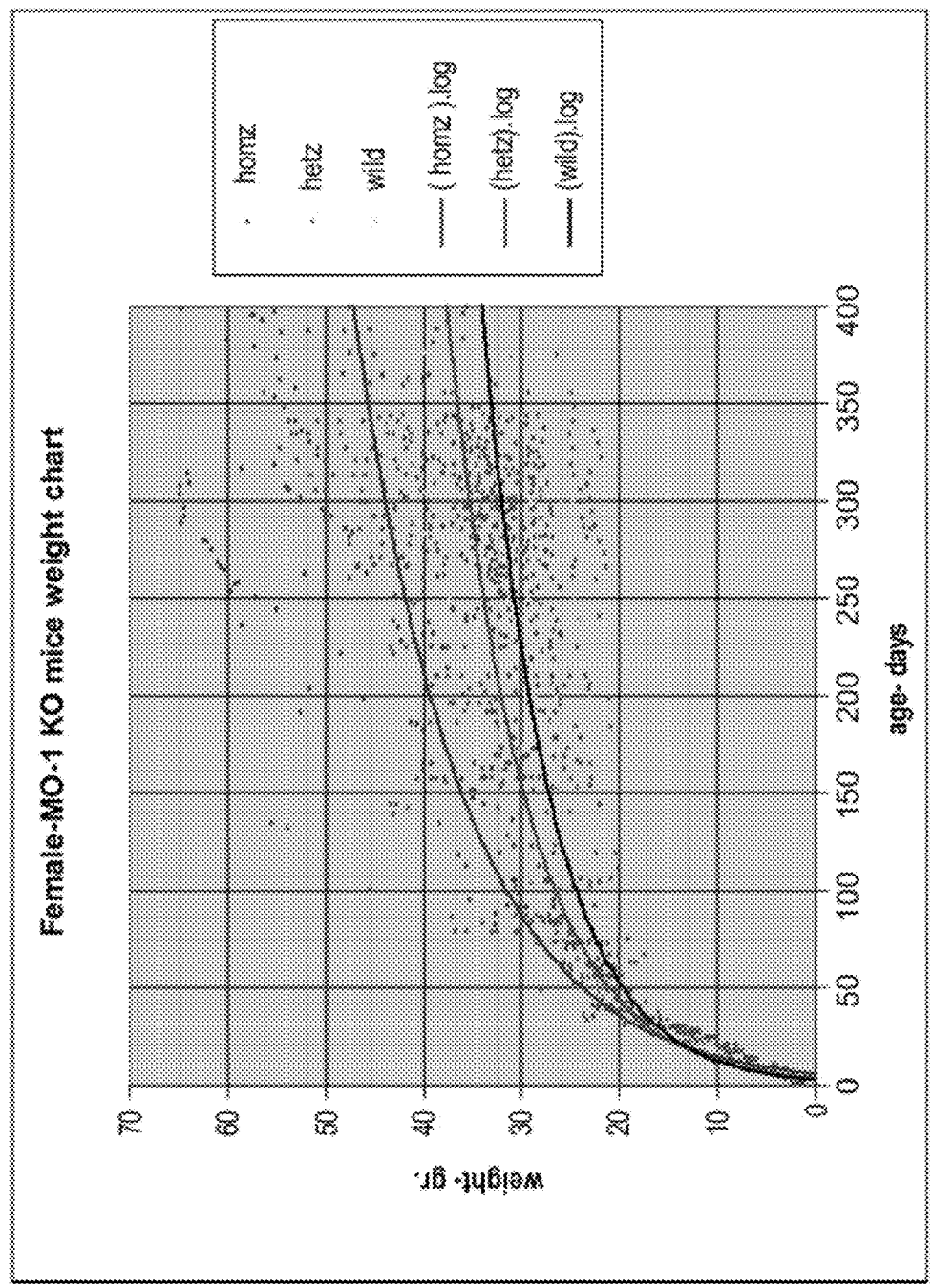

FIG. 50B is a graph depicting female MO-1-KO mice weight chart from birth to 400 days. Female MO-1-KO mice weight chart from birth to 400 days.

Figure 51:
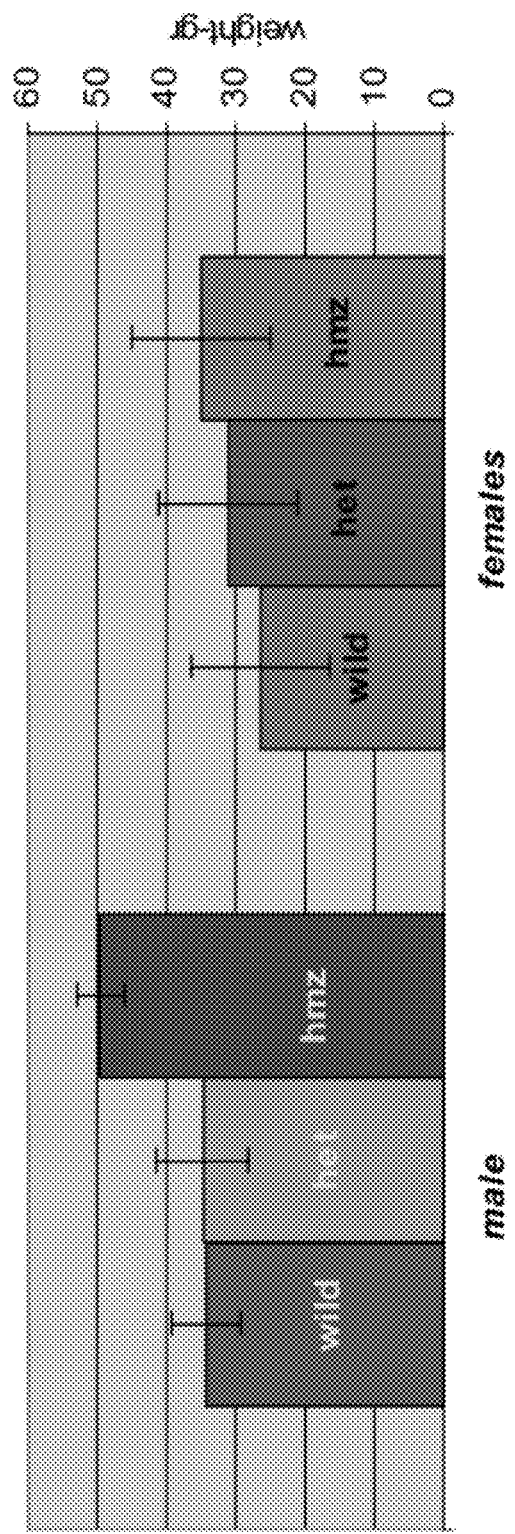

FIG. 51 is bar graph illustrating the average weight of male and female MO-1 gene knock out mice at 4-10 months of age.

Figure 52B:
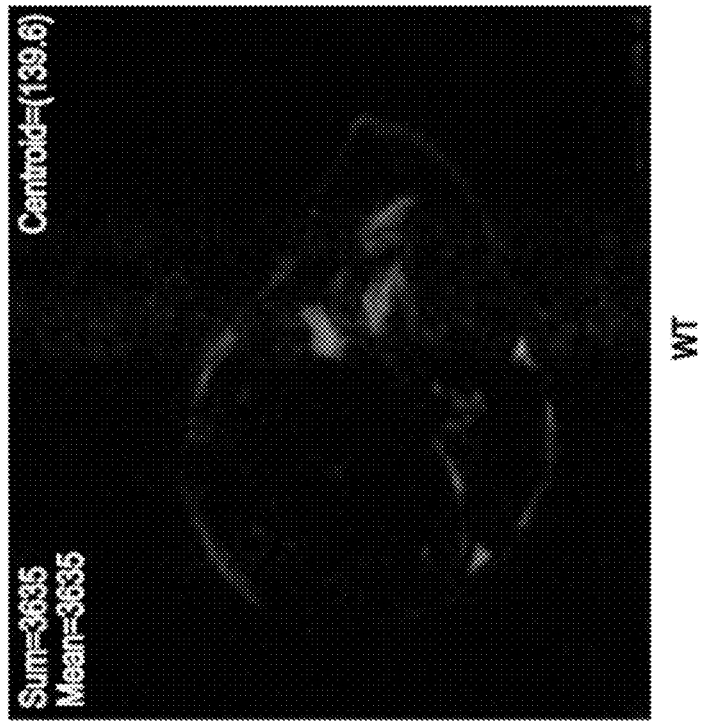
Figure 52A:

FIGS. 52A-B are photographs showing MRI results of the abdominal section of body fat content.

Figure 53:
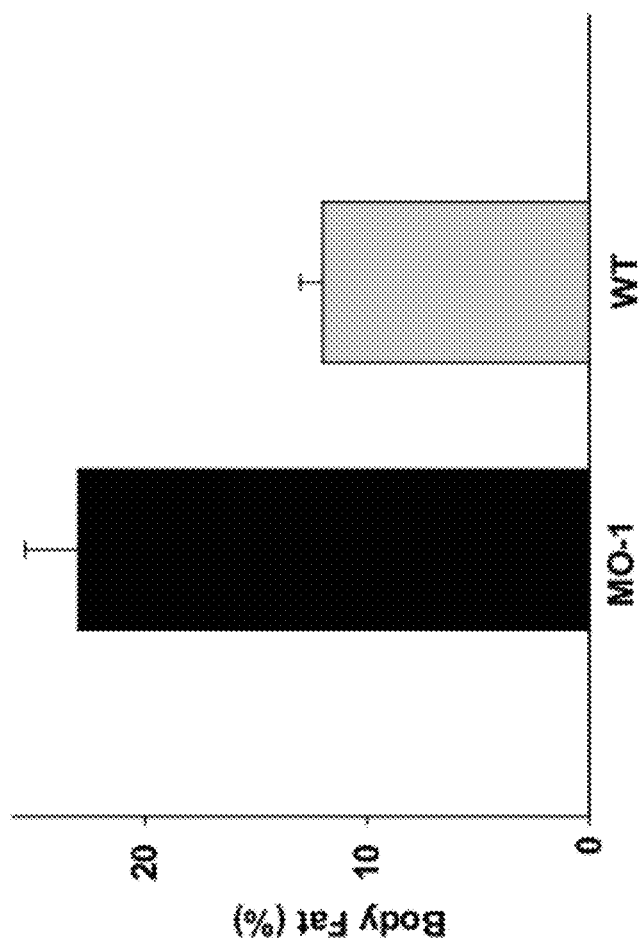

FIG. 53 is a bar graph illustrating body fat content in MO-1 knock out mice (MO-1) compared to wild type mice (WT).

Figure 54A:
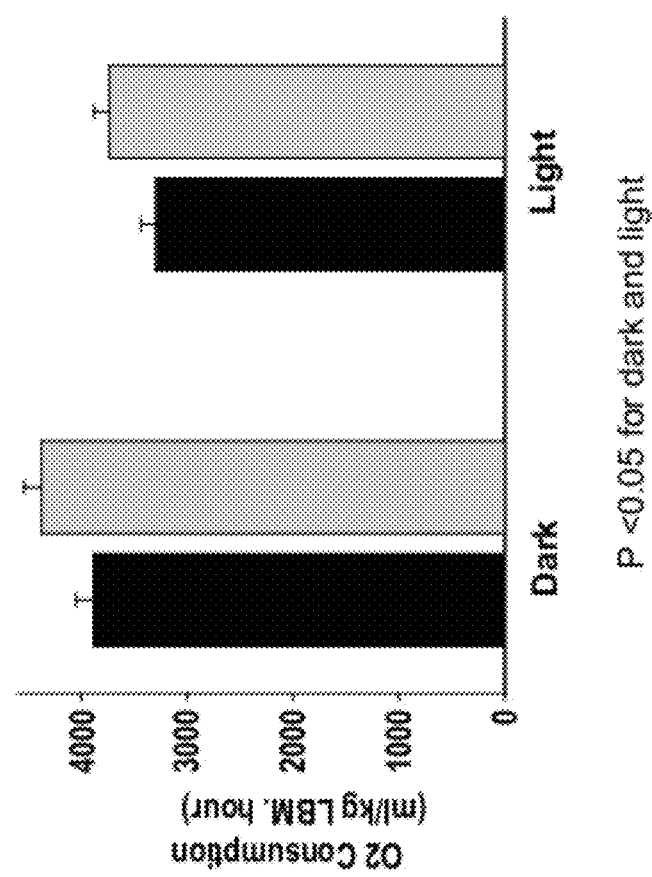
Figure 54B:
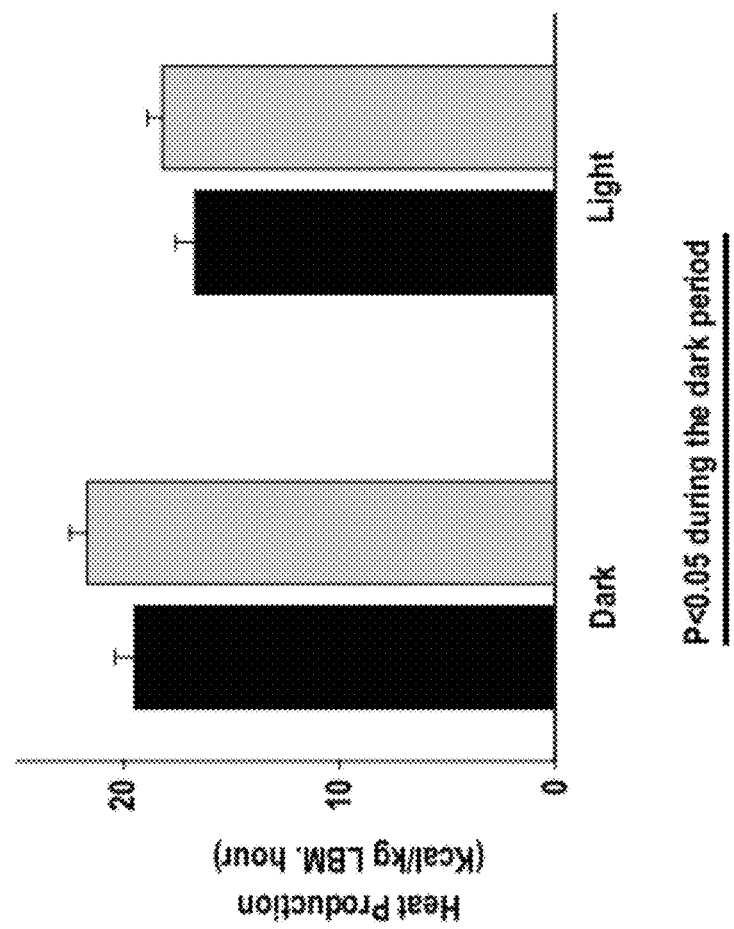
Figure 54C:
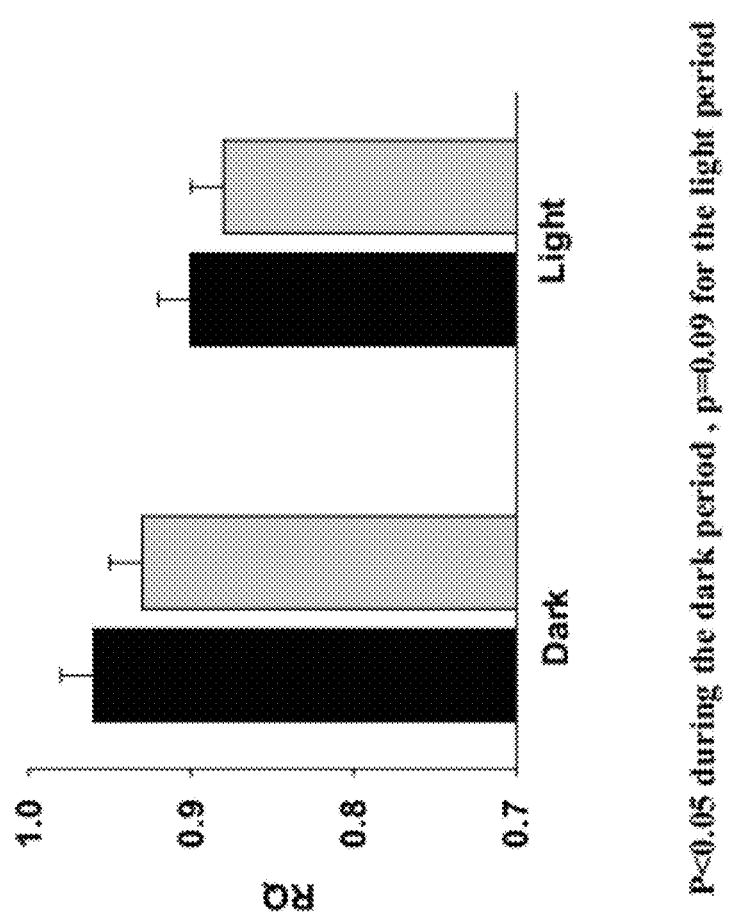

FIGS. 54A-C are bar graphs illustrating energy balance and substrate selection in MO-1 KO and WT mice. FIG. 54A depicts oxygen consumption, FIG. 54B depicts heat production, and FIG. 54C depicts respiratory quotient (RQ) as were assessed by a comprehensive animal metabolic monitoring system (CLAMS) in MO-1 KO and WT mice which were fed a regular diet. Metabolic parameters were measured over a 72 h period in 12 h dark 12 h light cycles, and equivalent time points, which were collected during the first second and third 24 h periods. The results are the mean of the average energy expenditure of each group during light and dark period.

FIG. 55 is a bar graph illustrating anxiety index in MO-1 knock out mice (MO-1), heterozygote and homozygote, compared to wild type mice (WT).

Figure 56:
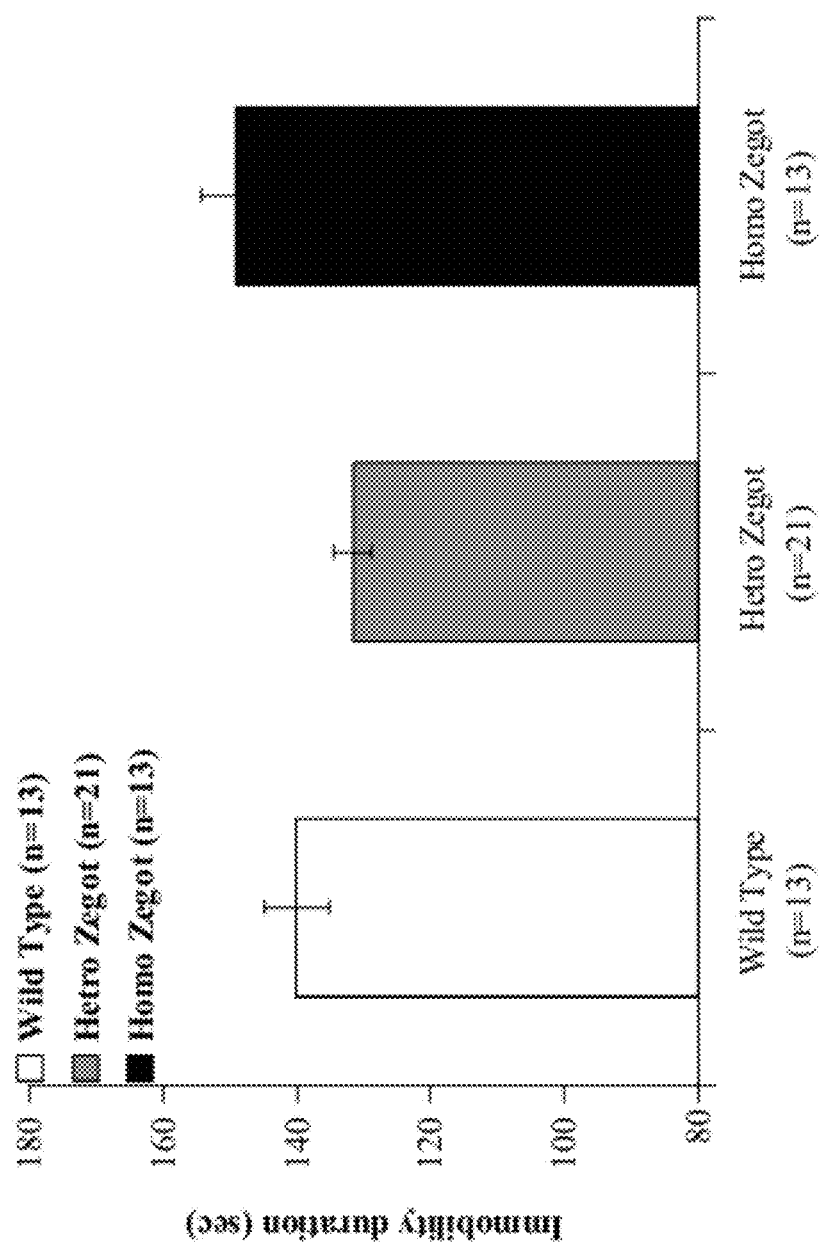

FIG. 56 is a bar graph illustrating immobility duration in MO-1 knock out mice (MO-1), heterozygote and homozygote, compared to wild type mice (WT).

DESCRIPTION OF SPECIFIC EMBODIMENTS OF THE INVENTION

The present invention, in some embodiments thereof, relates to a conditional MO-1 knock-out non-human animal and, more particularly, but not exclusively, to methods of generating and using same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The MO-1 gene is a novel nuclear gene of the metabolic syndrome associated with morbid obesity. This gene encodes a mitochondrial protein with partial structural similarity to phosphoenolpyruvate carboxykinase. A stop codon point mutation in MO-1 gene has been linked to the morbidly obese phenotype. Constitutive knock-out mice for the MO-1 gene have been generated in the past but are of limited use because knock-out of such genes from all cells and tissues may lead to early embryonic lethality. Furthermore, in cases in which the animals do survive, the constitutive gene knock-out leads to many undesirable effects which cannot be separated from the condition or disease being examined (e.g. fatty liver and diabetes).

The present inventor has now generated a conditional knock out mouse for the MO-1 gene.

As is shown herein below and in the Examples section which follows, the present inventor has generated two independent null mouse C57BL/6 substrains, 6J and 6NTac, each with a targeted deletion of the MO-1 gene (i.e. mouse AK005324 gene). As the MO-1 exon 1 is nearly contiguous with the inversely oriented first exon of the phosphatidylinositol glycan anchor biosynthesis, class X gene (PIGX), the knock-out strategy for both lines involved germline removal of MO-1 exon 3, avoiding disruption of the PIGX gene (see FIG. 3). Loss of MO-1 function resulted in obesity (see FIGS. 1A-B), and its co-morbid features including diabetes, cardiac disease, hypertension, and fatty liver in mice. As evident from the results, sex-matched mice had similar birth weights, but by 10 weeks of age differences were first apparent between knock-out and wild type male mice (see FIGS. 50A-B and 51). Measured at their greatest differences, both male and female knock-out mice were nearly 60% heavier than their age- and sex-matched controls. $MO-1^{-/-}$ mice showed markedly elevated levels of both total body fat mass and percentage body fat, with the percentage body fat being 2-fold higher in MO-1 KO mice compared to wild-type mice (see FIGS. 52A-B and 53). While food consumption normalized to lean body mass was similar between MO-1 KO and wild-type mice, an increase in body weight related to food intake was 2-fold greater in MO-1 KO compared to wild-type mice. Furthermore, MO-1 KO mice displayed a decrease in whole body oxygen consumption (see FIG. 54A), a lower locomotor activity (see FIG. 56), a decrease in heat production (see FIG. 54B), a decreased rate of energy expenditure (fed and fasted), a significant increase in whole body fat oxidation differences—the respiratory quotient (RQ, see FIG. 54C) and increased anxiety (see FIG. 55) compared to wild-type mice. Taken together, the results of the present invention demonstrate for the first time the importance of having a MO-1 knock-out model in which the MO-1 gene is selectively not expressed in a specific tissue or organ. This conditional knock-out MO-1 animal model provides novel insights into the molecular basis of obesity, energy homeostasis and fatty liver, being able to observe a targeted MO-1 mutation (e.g. lack of MO-1 in a specific organ) rather than testing an animal completely lacking MO-1 gene expression (i.e. constitutive knock-out mouse).

Thus, according to one aspect of the present invention there is provided a conditional knock-out non-human animal, wherein some cells of the non-human animal but not all the cells comprise a disrupted MO-1 nucleic acid sequence, wherein the disruption results in an inability of the non-human animal to produce detectable levels of the MO-1 protein, as assayed by Southern blot analysis.

As used herein, the term "conditional knock-out non-human animal" or "conditional KO non-human animal" refers to a non-human animal which carries one or more genetic manipulations leading to deactivation of a MO-1 gene in a tissue and optionally time specific manner.

According to an embodiment of the present invention, the non-human animal is a mammal, more specifically a rodent such as a mouse or a rat. Other non-human animals of the present invention include primates, sheep, rabbits, pigs, hamsters, dogs, cows, goats, chickens, amphibians, etc.

Typically, the MO-1 knock-out animal of the present invention exhibits one or more phenotypes including, but not limited to, obesity, diabetes, cardiac disease, hypertension, fatty liver, increased anxiety, decreased locomotion and decreased fertility.

As used herein, "MO-1" refers to proteins or peptides which are endogenously expressed in the non-human animal. The MO-1 proteins or peptides of the present invention typically have an amino acid sequence that is homologous to SEQ ID NO:1, as well as proteins sharing sequence similarity, e.g., 70%, 75%, 80%, 85%, 90%, 95% or 100%, with the amino acid sequence of SEQ ID NO: 1. Further, these proteins have a biological activity in common with the polypeptide having the amino acid sequence of SEQ ID NO: 1, including, but not limited to, antigenic cross-reactivity, auto-inhibition, phosphorylation activity, and the like. It is also contemplated that a MO-1 protein can have one or more conservative or non-conservative amino acid substitutions, or additions or deletions from the amino acid sequence of SEQ ID NO: 1. MO-1 also includes proteins or peptides expressed from different mutations, different spliced forms and various sequence polymorphisms of the MO-1 gene so long as the protein having such sequence alteration shares a biological activity as described above with the polypeptide of SEQ ID NO: 1.

According to a specific embodiment of the present invention, the MO-1 protein of the present invention is a mouse MO-1 homolog, i.e. AK005324 protein product (BAB23954), as set forth in SEQ ID NO: 45. Thus, the MO-1 proteins or peptides of the present invention may comprise an amino acid sequence that is about 70%, about 75%, about 80%, about 85%, about 90%, about 95% or about 100% identity with the amino acid sequence of SEQ ID NO: 45.

As used herein, a "MO-1 gene" refers to a gene that encodes MO-1 as defined herein. The term "MO-1 gene" is understood to include the various sequence polymorphisms and allelic variations that exist within the population. This term relates primarily to an isolated coding sequence, but can also include some or all of the flanking regulatory elements and/or intron sequences (e.g., genomic sequence). The RNA transcribed from a mutant MO-1 gene is mutant MO-1 messenger RNA.

As used herein, the term "disrupted MO-1 nucleic acid sequence" refers to a mutation in a MO-1 gene (e.g. an endogenous MO-1 gene) including nucleotide sequence changes, additions or deletions, including deletion of small or large portions or the entire MO-1 gene. The mutations in the MO-1 gene are not constitutively expressed within the animal but are rather effected in a tissue and/optionally time specific manner, such that only some cells of the animal but not all of them do not express the MO-1 protein. The MO-1 gene disruption results in an inability of the animal to produce a functional MO-1 protein. Typically the KO animal is not able to produce detectable levels of the MO-1 protein. Methods of measuring detectable levels of MO-1 protein are well known in the art and include, without being limited to, Southern blot analysis, Western blotting and PCR techniques [e.g. reverse transcriptase-PCR (RT-PCR)].

Typically, the conditional MO-1 knock-out animal is formed by transfecting embryonic stem cells, with the MO-1 gene, which is later rendered nonfunctional upon activation in a mature organism (explained in further detail below). This involves insertion of a specific DNA sequence, such as a knock-out nucleic acid construct, into the non-human animal DNA.

According to a specific embodiment, the endogenous MO-1 gene is altered by an exogenous DNA molecule that recombines homologously with the endogenous MO-1 in a (e.g., embryonic) cell prior to development of the animal.

As used herein, the term "knock-out nucleic acid construct" is a nucleic acid sequence, such as a DNA construct, which, when introduced into a cell, results in suppression (partial or complete) of expression of a polypeptide or protein encoded by endogenous DNA in the cell.

An exemplary knock-out construct is provided herein. This construct contains at least a portion of an MO-1 gene, wherein exon 3 of the MO-1 gene is flanked by a 5' loxP site and a 3' selectable marker cassette, wherein the selectable marker cassette is flanked by frt sites 3' and a 5' to the frt, and further wherein a loxP site is positioned 3' to the 3' frt site.

Formation of the knock-out or mutant organism is initiated by isolating a MO-1 gene or nucleotide sequence. The isolated sequence can be any of a variety of structures, including genes, gene fragments, polynucleotides, oligonucleotides, and any nucleotide structure that can be substituted into the genome of a host and result in expression of a functional MO-1 polypeptide, until it is desired to mutagenize such structure. While it is preferred to isolate a gene, other hereditary units may be used. Homologous sequences are available, as are orthologs. Functional mutant sequences of MO-1 may be used. Gene fragments are available, as long as the organism properly develops prior to activation of the mutant.

As such, any of a variety of nucleotide sequences can be used, as for example, the homologues of SEQ ID NOs: 2 or 3. Alternatively, any nucleotide sequence which shares at least about 70% identity, at least about 75% identity, at least about 80% identity, at least about 85% identity, at least about 90% identity or at least about 95% identity or more, with the nucleotide sequences set forth in SEQ ID NOs: 2 or 3 may be used according to the present teachings.

According to a specific embodiment of the present invention, the MO-1 nucleotide sequence of the present invention is a mouse MO-1 homolog, i.e. AK005324, as set forth in SEQ ID NO: 44. Any nucleotide sequence which shares at least about 70% identity, at least about 75% identity, at least about 80% identity, at least about 85% identity, at least about 90% identity or at least about 95% identity or more, with the nucleotide sequence set forth in SEQ ID NO: 44 may be used according to the present teachings.

It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad Sci. USA 89:10915 (1992). Algorithms conveniently employed for this purpose are widely available (see, for example, Needleman and Wunsch in J. Mol. Bio. 48:443 (1970).

The knock-out or mutant animal of the present teachings includes organisms formed from transfected embryonic stem cells. The gene selected is preferably isolated from the species in which the gene is to be used. For example, if the procedure is to be conducted in a mouse, then the MO-1 gene is preferably isolated from a mouse. Any of a variety of species, however, may be used (as discussed above).

As mentioned, the MO-1 gene or nucleotide sequence can be derived from a variety of species. Preferably, mammalian organisms are used. According to a specific embodiment, a mammalian gene, in particular mus musculus (mouse), is used. It will be appreciated that although some embodiments of the invention may relate to mouse knockout they are intended to relate to any non-human animal as contemplated herein.

The selected isolated nucleotide sequence is preferably amplified. This is done to provide a sufficient amount of MO-1 or other nucleotide sequence, so that vectors can be formed. A vector is an autonomously self-replicating nucleic acid molecule that transfers a target nucleic acid sequence into a host cell. The vector's target nucleic acid sequence can be a wild type or mutant gene, or fragment derived therefrom. The vector can include a gene expression cassette, plasmid, episome, or fragment thereof. Gene expression cassettes are nucleic acid sequences with one or more targeted genes that can be injected or otherwise inserted into host cells for expression of the encoded polypeptides. Episomes and plasmids are circular, extrachromosomal nucleic acid molecules, distinct from the host cell genome, which are capable of autonomous replication. The vector may contain a promoter, marker or regulatory sequence that supports transcription and translation of the selected target gene. Viruses are vectors that utilize the host cell machinery for polypeptide expression and viral replication.

It may be necessary to amplify one of the foregoing MO-1 nucleic acid sequences, which can be accomplished using standard PCR technology, prior to insertion into a vector. The MO-1 nucleotide sequence can be mutagenized or attached to at least two recombination sites. If a mutation is made, it is made in such a way that the MO-1 gene or nucleotide sequence encodes an inactive MO-1 polypeptide. The resultant mutation can be a frame shift, point, substitution, loss of function, knock-out deletion or conventional deletion mutation. Importantly, the mutant sequence should remain substantially homologous to the wild type animal, but render the resultant gene nonfunctional. A preferred option is to form a mutant MO-1 sequence that is a truncated sequence, which is a shortened sequence that encodes a nonfunctional MO-1 polypeptide. According to a specific embodiment, Exon 3 of the MO-1 sequence is knocked-out, resulting in a truncated nonfunctional MO-1 gene sequence. An example of such a sequence is set forth in SEQ ID NO: 11 (e.g. coordinates 45-58 of the mouse predicted MO-1 polypeptide set in SEQ ID NO: 45). As such, a deletion mutation may be made directly in the sequence.

When the conditional mutant is formed, the MO-1 nucleic acid sequence should be such that it is fully functional throughout the development of the organism until steps are taken to inactivate the nucleotide sequence. Inactivation occurs once the organism has sufficiently developed. Conditional mutant formation is accomplished by placing nucleotide sequences flanked by recombination sequences into the genome so that the recombination sequence can be later activated. The recombination sequence can be used to cleave a gene or exon from the genome. Preferably, a pair of recombination fragments is used. This can be accomplished by placing the sequence in a vector that places recombination sites on either end of the desired nucleotide sequence. The recombination sites are substituted with the nucleotide sequence into the organism, with the recombination sites activated at a later time.

Next, the conditional recombination sequence is inserted into a vector. The vector for forming the conditional mutant includes the targeted MO-1 nucleic acid sequence, preferably flanked by recombination sites. The conditional vector is structured such that the targeted, recombination-site flanked gene or nucleotide sequence is cut from the genome to form a knock-out mutant.

In determining whether a polypeptide or polynucleotide is substantially homologous to a polypeptide or nucleotide suitable for use in the current invention, sequence similarity may be determined by conventional algorithms, which typically allow introduction of a small number of gaps in order to achieve the best fit. In particular, "percent homology" of two polypeptides or two nucleic acid sequences is determined using the algorithm of Karlin and Altschul (Proc. Natl. Acad. Sci. USA 87:2264-2268, 1993). Such an algorithm is incorporated into the NBLAST and XBLAST programs of Altschul et al. (J. Mol. Biol. 215:403-410, 1990). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are employed. See http://wwwdotncbidotnlmdotnihdotgov for more details.

In either mutant, any of a variety of vectors may be used. Formation of the vector follows standard and known procedures and protocols. Suitable vectors include expression vectors, fusion vectors, gene therapy vectors, two-hybrid vectors, reverse two-hybrid vectors, sequencing vectors, and cloning vectors. Vectors are formed from both the isolated nucleic acid sequences and the mutant versions of the isolated nucleic acid sequences.

Eukaryotic and prokaryotic vectors may be used. Specific eukaryotic vectors that may be used include MSCV, Harvey murine sarcoma virus, pFastBac, pFastBac HT, pFastBac DUAL, pSFV, pTet-Splice, pEUK-C1, pPUR, pMAM, pMAMneo, pBI101, pBI121, pDR2, pCMVEBNA, YACneo, pSVK3, pSVL, pMSG, pCH110, pKK232-8, p3'SS, pBlueBacIII, pCDM8, pcDNA1, pZeoSV, pcDNA3, pREP4, pCEP4, and pEBVHis vectors. The MSCV or Harvey murine sarcoma virus is preferred. Prokaryotic vectors that can be used in the present invention include pET, pET28, pcDNA3.1/V5-His-TOPO, pCS2+, pcDNA II, pSL301, pSE280, pSE380, pSE420, pTrcHis, pRSET, pGEMEX-1, pGEMEX-2, pTrc99A, pKK223-3, pGEX, pEZZ18, pRIT2T, pMC1871, pKK233-2, pKK38801, and pProEx-HT vectors.

A variety of selectable markers may be included with the vector. Available markers include antibiotic resistance genes, a tRNA gene, auxotrophic genes, toxic genes, phenotypic markers, colorimetric markers, antisense oligonucleotides, restriction endonuclease, enzyme cleavage sites, protein binding sites, and immunoglobulin binding sites. Specific selectable markers available include LacZ, neo, Fc, DIG, Myc, and FLAG.

For generating a conditional knockout the cre/loxp system is typically involved. Cre is a 38 kDa recombinase protein from bacteriophage P1 which mediates intramolecular (excisive or inversional) and intermolecular (integrative) site specific recombination between loxP sites (see review article by Brian Sauer in Methods of Enzymology; 1993, Vol. 225, 890-900).

A loxP site (locus of X-ing over) consists of two 13 bp inverted repeats separated by an 8 bp asymmetric spacer region.

One molecule of Cre binds per inverted repeat or two Cre molecules line up at one loxP site. The recombination occurs in the asymmetric spacer region. Those 8 bases are also responsible for the directionality of the site. Two loxP sequences in opposite orientation to each other invert the intervening piece of DNA, two sites in direct orientation dictate excision of the intervening DNA between the sites leaving one loxP site behind. This precise removal of DNA can be used to eliminate an endogenous gene or transgene i.e., MO-1 in this case. Thus, the Cre/loxP system is a tool for tissue-specific (and in connection with the tet system also time-specific) knock-out of such genes which cannot be investigated in differentiated tissues because of their early embryonic lethality in mice with conventional knock-outs. It can also be used for the removal of a transgene (which was overexpressed in a specific tissue) at a certain time point to study the invert effect of a downregulation of the transgene in a time course experiment.

Two mouse lines are required for conditional gene deletion. First, a conventional transgenic mouse line with Cre targeted to a specific tissue or cell type, and secondly a mouse strain that embodies a target gene (endogenous gene or transgene) flanked by two loxP sites in a direct orientation ("floxed gene"). Recombination (excision and consequently inactivation of the target gene) occurs only in those cells expressing Cre recombinase. Hence, the target gene remains active in all cells and tissues which do not express Cre.

Thus, according to a specific embodiment, the endogenous MO-1 gene is altered by an exogenous DNA molecule that recombines homologously with the endogenous MO-1 in a (e.g., embryonic) cell prior to development of the animal.

The conditional vector includes recombination sites that cause insertion of a conditional knock-out mutation (MO-1, for example) or a mutant, wherein MO-1 is rendered nonfunctional. This can be achieved by the knock-in of a Cre or Flp recombinase site, or a Cre-Fre site combination thereof, into a specific MO-1 gene locus or loci. The expression of Cre or Flp recombinase is under the control of the endogenous locus in a tissue-specific and optionally time-dependent manner. The temporal/spatial-restricted Cre/Flp expression line leads to a conditional or selective deletion of the target gene (e.g., MO-1) when crossed with an organism in which LoxP or FRT recombination sites flank the target gene. Preferably, neomycin (i.e. neo) marker, flanked by LoxP or FRT recombination sites, is utilized to determine the efficiency of recombination of the target gene. A combination of the Cre/LoxP and Flp/FRT systems also allows selective and simultaneous deletion of the two gene loci of interest. Other alternative recombination systems and marker systems, however, can be devised and used as known in the art.

The two functional units required for in vivo targeted conditional DNA deletion of the MO-1 receptor gene in the Cre-LoxP organism system are: (1) expression of the Cre recombinase gene, often induced by a cell-specific or regulated promoter; and (2) at least one integrated DNA target gene segment that is flanked by LoxP. The LoxP-flanked target DNA is said to be "floxed."

The conditional KO vector is used to transfect any of a variety of cells. It is preferred to transfect embryonic stem (ES) cells, with the MO-1 recombination sequence. Embryonic stem (ES) cells are typically selected for their ability to integrate into and become part of the germ line of a developing embryo so as to create germ line transmission of the transgene. Thus, any ES cell line that can do so is suitable for use herein. For example, the 129/SvPas ES cell line described herein may be used. Alternatively, suitable cell lines which may be used include, but are not limited to, the 129SvEv ES cell line, the 129J ES cell line, the D3 ES or the J1 ES cell line. The cells are cultured and prepared for DNA insertion using methods well-known to the skilled artisan.

Typically, the ES cells are transplanted into the uterus of an adoptive host mother, so that an embryo can gestate from the ES cells (described in further detail below). The vector can also be used to transfect cells (e.g. liver cells) in a mature organism, such as an embryo. The particular type of cell to be transfected influences the vector selected. Also, the cells to be transfected can be grown in vivo or in vitro. The mutant sequence can be used to transfect cells present in an embryo or more mature organisms.

Introduction of the construct into ES cells is accomplished using a variety of methods well-known in the art, including, but not limited to, electroporation, microinjection, microvessel transfer, particle bombardment, liposome mediated transfer and calcium phosphate treatment. For introduction of the DNA sequence, the knock-out construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct.

Screening for cells which contain the transgene (homologous recombinants) is done using a variety of methods. For example, as described herein, cells can be processed as needed to render DNA in them available for screening with specific probes by polymerase chain reaction (PCR).

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Successful incorporation of ES cells into implanted embryos results in offspring termed chimeras. The term "chimera" relates to an individual composed of a mixture of genetically different cells. By definition, genetically different cells of chimeras are derived from genetically different zygotes.

Chimeras capable of germline transmission of the mutant allele are identified by standard methods. Chimeras are bred and the resulting progeny are screened for the presence of the desired alteration (e.g., the modified MO-1 gene). This is done, for example, on the basis of coat color or by obtaining DNA from offspring (e.g., tail DNA) to assess for the transgene, using known methods (e.g., Southern analysis, dot blot analysis, PCR analysis). Transgene expression may also be assessed (e.g., to determine if a replacement construct is expressed) by known methods, such as northern analysis or PCR analysis. Southern hybridization or PCR analysis of progeny DNA (e.g., tail DNA) may be conducted to identify desired genotypes.

Typically, two organism (mouse, for example) lines are required for formation of a conditional knock-out animal: a conventional transgenic line with, for example, Cre-targeted to a specific tissue or cell type, and a strain that embodies a target gene (endogenous gene or transgene) flanked by two recombination (LoxP, for example) sites in a direct orientation ("floxed gene"). When the target gene is the MO-1 gene, recombination occurs by excision and, consequently, inactivation of the floxed MO-1 target gene. Since recombination and MO-1 gene excision occurs only in those cells expressing Cre recombinase, the MO-1 target gene remains active in all cells and tissues that do not express Cre recombinase. Gene excision is induced by a recombination activator, such as PolyI:C or interferon, which in turn triggers Cre recombinase expression. The recombination activator is preferably injected postnatally to ensure organism survival. Most preferably the recombination activator is injected at 0, 1, 2, or days after birth, or anytime thereafter. Cre and FLP recombinase are exemplary recombinases that may be used. Cre recombinase is used to cleave Lox sites flanking the MO-1 gene, such as LoxP and LoxC2 sites. Alternatively, FLP recombinase can be used with FRT recombination sites flanking the MO-1 gene.

Accordingly, the present invention describes a KO mouse wherein the disrupted gene is the MO-1 gene. Conditional disruption of the MO-1 gene was obtained by breeding the KO mice with mice that express frt recombinase (also known as flippase) or Cre recombinase.

According to one embodiment of the present invention, the action of flippase removes the neomycin gene and the action of Cre recombinase removes a critical part of the targeted gene of interest (e.g. exon 3 of MO-1).

In another embodiment of the present invention, the action of Cre recombinase removes both the neomycin gene a critical part of the targeted gene of interest (e.g. exon 3 of MO-1).

The Jackson Laboratory (Bar Harbor, Me.) sells over 70 strains of mice expressing flippase or Cre recombinase. The flippase or Cre recombinase-expressing mouse strains express these enzymes in all mouse tissues, or can express the enzymes under signals that cause them to be present only in specific tissues, such as in liver tissue, kidney tissue, muscle tissue, pancreatic tissue, prostate tissue, or only in a specific cell type, such as astrocytes. In addition to tissue- or cell-specific signals, development-specific signals (such as endogenous developmental factors or diet responsive gene promoters) can be used to control the time of flippase or Cre recombinase expression.

Thus, in order to achieve conditional knock-out animal, two animals may be bred, one expressing the floxed MO-1 gene and the other expressing a Cre recombinase under the control of a tissue or time specific promoter. Alternatively, a knock-out animal may be transfected with two expression constructs, one expressing the floxed MO-1 gene and the other expressing a Cre recombinase under the control of a tissue or time specific promoter.

According to an embodiment of the present invention, a nucleic acid construct system is disclosed. The construct system comprising (i) a first nucleic acid construct which comprises an MO-1 nucleic acid sequence and a selectable marker both flanked by loxP sites and (ii) a second nucleic acid construct which comprises a Cre recombinase under the control of a tissue specific promoter.

Examples of tissue specific promoters which may be used in accordance with the present teachings include, but are not limited to, the liver specific promoter SV40/bAlb, the muscle specific promoters Mb and Desmin, the pancreatic cell specific promoter Elastase-1.

The knock-out organism permits conditional excision of the target MO-1 gene upon the injection of a recombination activator into the organism. The knock-out animal may be a pre-recombination or post-recombination animal, where the pre-recombination animal is the MO-1 mutant animal prior to injection of the recombination activator and the post-recombination animal is the MO-1 mutant animal after injection of the activator.

As described in detail in the Examples section which follows, removal of exon 3 of MO-1 leads to inactivation of the MO-1 gene due to lack of a start codon and thus no production of protein (FIGS. 5-7). Preferably in the MO-1 KO animal of the present teachings, the target gene expression is undetectable or insignificant.

The present invention further provides a method of generating a non-human animal with a targeted conditional disruption in an MO-1 gene. The method comprising: (a) transfecting a nucleic acid construct which comprises an MO-1 nucleic acid sequence and a selectable marker both flanked by loxP sites into a population of murine embryonic stem (ES) cells; (b) selecting a transfected ES cell which expresses the selectable marker; (c) introducing the transfected ES cell into an embryo of an ancestor of the non-human animal; (d) allowing the embryo to develop to term to produce a chimeric non-human animal with a conditional knock-out construct in its germ line; (e) breeding the chimeric non-human animal with a non-human animal expressing flippase to produce a heterozygous non-human animal which does not contain the selectable marker; and (f) breeding the heterozygous non-human animal with a non-human animal expressing a Cre recombinase under the control of a stage- or tissue-specific promoter to produce the non-human animal with the targeted conditional disruption in the MO-1 gene.

According to an embodiment of the present invention a conditional MO-1 KO animal is generated to create an organ/tissue specific conditional MO-1 KO animal.

The organ specific knock out may include at least 1 2 or 3 organs/tissues in which the expression of the MO-1 gene is disrupted, According to a specific embodiment of the present invention the organ specific conditional MO-1 KO animal is a liver specific conditional MO-1 KO animal.

According to a specific embodiment of the present invention the organ specific conditional MO-1 KO animal is a kidney specific conditional MO-1 KO animal.

According to a specific embodiment of the present invention the organ specific conditional MO-1 KO animal is a muscle specific conditional MO-1 KO animal.

According to a specific embodiment of the present invention the organ specific conditional MO-1 KO animal is a pancreas specific conditional MO-1 KO animal.

As mentioned, the MO-1 KO animal comprises some cells (the cells may be germ cells and/or somatic cells) with the disrupted MO-1 nucleic acid sequence, however, not all of the animal's cells comprise the disrupted MO-1 nucleic acid sequence. Thus, for example, liver cells, pancreatic cells, muscle cells, kidney cells and alike may have disrupted MO-1 expression.

According to another specific embodiment, the cells with the disrupted MO-1 nucleic acid sequence are comprised in one or in two or more tissues (e.g. liver and kidney, liver and muscle, etc.).

It will be appreciated that tissues and cells may be obtained from the conditional MO-1 KO animal of the present invention. Such tissues may comprise cells expressing the disrupted MO-1 nucleic acid sequence and cells not expressing the disrupted MO-1 nucleic acid sequence.

The conditional knockout mice, and resultant tissues, described herein are useful for the study the role of the MO-1 gene in the formation, progression and metabolism of obesity, obesity related disorders (e.g. diabetes) and fatty liver.

Furthermore, the conditional KO animals (e.g. MO-1 KO mice) and the tissues obtained therefrom, are useful in screening drugs or therapeutic modalities for the treatment of obesity, fatty liver, diabetes, hypertension, etc.

As described in detail in the Examples section which follows, the MO-1 KO mice of the present invention had fatty livers (see Example 30). Thus, the conditional MO-1 KO animals of the present invention may serve as useful models for studying the cause of fatty livers and metabolic syndrome and for research of therapeutics for the treatment of same by allowing specific organ targeting (e.g. liver MO-1 KO animals, pancreas MO-1 KO animals).

Furthermore, the MO-1 KO mice of the present invention were obese and had high levels of body fat (see Example 30 and FIGS. 50-53). Thus, the conditional MO-1 KO animals of the present invention may serve as useful models for studying the cause of glucose metabolism, diabetes and metabolic syndrome by allowing specific organ targeting (e.g. liver MO-1 KO animals, pancreas MO-1 KO animals).

Thus, according to an embodiment of the present invention, there is provided a method of screening for a test agent which modulates metabolic activity. The method comprising: (a) contacting the agent with the conditional MO-1 KO non-human animal of the present invention or with a tissue isolated therefrom; (b) analyzing a phenotype (e.g. MO-1 expression or activity) of the tissue or the non-human animal; and (c) comparing the phenotype following the contacting to prior to the contacting, wherein an alteration in the phenotype is indicative of an agent which modulates metabolic activity.

As used herein, the term "metabolic activity" refers to the set of chemical reactions that maintain life in any organism. Metabolic activity involves the transformation of energy and matter in the body, two elements that must always be present for life to be sustained. Two types of metabolic processes are anabolism and catabolism. Anabolism is constructive metabolism, during which small molecules are formed into larger ones, requiring an input of energy. Catabolism is the opposite process; it necessitates an output of energy, and large molecules are broken into smaller ones.

Metabolic activity can be assayed by food consumption, the body weight, the oxygen consumption, the locomotor activity, the heat production, the rate of energy expenditure and body fat oxidation in a conditional MO-1 KO animal.

An agent may modulate metabolic activity by enhancing or decreasing glucose concentrations, enhancing or decreasing lipid concentrations, enhancing or decreasing mass of the animal, enhancing or decreasing food consumption by the animal, enhancing or decreasing the rate of energy expenditure and the body fat oxidation.

In certain embodiments, the increase may be a 1.25-, 1.5-, 2-, 4-, 6-, 8-, 10-, or greater fold increase in metabolic activity of conditional MO-1 KO animal or tissue contacted with the test compound compared to the level of same in a control animal or tissue.

In certain embodiments, the decrease may be a 1.25-, 1.5-, 2-, 4-, 6-, 8-, 10-, or greater fold decrease in metabolic activity of conditional MO-1 KO animal or tissue contacted with the test compound compared to the level of same in a control animal or tissue.

The metabolic activity modulating compound may comprise a protein, for example, an antibody; a nucleic acid; or a small molecule. As used herein, the term "small molecule" includes, but is not limited to, organic or inorganic compounds (i.e., including heteroorganic and organometallic compounds) having a molecular weight less than 10,000 grams per mole, organic or inorganic compounds having a molecular weight less than 5,000 grams per mole, organic or inorganic compounds having a molecular weight less than 1,000 grams per mole, organic or inorganic compounds having a molecular weight less than 500 grams per mole, organic or inorganic compounds having a molecular weight less than 100 grams per mole, and salts, esters, and other pharmaceutically acceptable forms of such compounds. Salts, esters, and other pharmaceutically acceptable forms of such compounds are also encompassed.

By way of example, diversity libraries, such as random or combinatorial peptide or nonpeptide libraries can be screened for molecules that specifically modulate metabolic activity in conditional MO-1 KO animals or tissues. Many libraries are known in the art that can be used, e.g., chemically synthesized libraries, recombinant (e.g., phage display libraries), and in vitro translation-based libraries.

Examples of chemically synthesized libraries are described in Fodor et al., Science 251:767-773 (1991); Houghten et al., Nature 354:84-86 (1991); Lam et al., Nature 354:82-84 (1991); Medynski, Bio/Technology 12:709-710 (1994); Gallop et al., J. Medicinal Chemistry 37 (9):1233-1251 (1994); Ohlmeyer et al., Proc. Natl. Acad. Sci. U.S.A. 90:10922-10926 (1993); Erb et al., Proc. Natl. Acad. Sci. U.S.A. 91:11422-11426 (1994); Houghten et al., Biotechniques 13:412 (1992); Jayawickreme et al., Proc. Natl. Acad. Sci. U.S.A. 91:1614-1618 (1994); Salmon et al., Proc. Natl. Acad. Sci. U.S.A. 90:11708-11712 (1993); PCT Publication No. WO 93/20242; and Brenner and Lerner, Proc. Natl. Acad. Sci. U.S.A. 89:5381-5383 (1992).

Examples of phage display libraries are described in Scott and Smith, Science 249:386-390 (1990); Devlin et al., Science, 249:404-406 (1990); Christian, R. B., et al., J. Mol. Biol. 227:711-718 (1992)); Lenstra, J. Immunol. Meth. 152: 149-157 (1992); Kay et al., Gene 128:59-65 (1993); and PCT Publication No. WO 94/18318, published Aug. 18, 1994. In vitro translation-based libraries include but are not limited to those described in PCT Publication No. WO 91/05058, published Apr. 18, 1991; and Mattheakis et al., Proc. Natl. Acad. Sci. U.S.A. 91:9022-9026 (1994).

By way of examples of non-peptide libraries, a benzodiazepine library (see e.g., Bunin et al., Proc. Natl. Acad. Sci. U.S.A. 91:4708-4712 (1994)) can be adapted for use. Peptoid libraries (Simon et al., Proc. Natl. Acad. Sci. U.S.A. 89:9367-9371 (1992)) can also be used. Another example of a library that can be used, in which the amide functionalities in peptides have been permethylated to generate a chemically transformed combinatorial library, is described by Ostresh et al., Proc. Natl. Acad. Sci. U.S.A. 91:11138-11142 (1994).

Screening the libraries can be accomplished by any of a variety of commonly known methods. See, e.g., the following references, which disclose screening of peptide libraries: Parmley and Smith, Adv. Exp. Med. Biol. 251:215-218 (1989); Scott and Smith, Science 249:386-390 (1990); Fowlkes et al., Bio/Techniques 13:422-427 (1992); Oldenburg et al., Proc. Natl. Acad. Sci. U.S.A. 89:5393-5397 (1992); Yu et al., Cell 76:933-945 (1994); Staudt et al., Science 241:577-580 (1988); Bock et al., Nature 355:564-566 (1992); Tuerk et al., Proc. Natl. Acad. Sci. U.S.A. 89:6988-6992 (1992); Ellington et al., Nature 355:850-852 (1992); U.S. Pat. No. 5,096,815, U.S. Pat. No. 5,223,409, and U.S. Pat. No. 5,198,346; Rebar and Pabo, Science 263:671-673 (1993); and PCT Publication No. WO 94/18318, published Aug. 8, 1994.

As would clearly be understood by a person of ordinary skill in the art, any and/or all of the embodiments disclosed herein for identifying an agent, drug, or compound that can modulate metabolic activity in conditional MO-1 KO animals or tissues, including such procedures that incorporate rational drug design, as disclosed herein, can be combined to form additional drug screens and assays, all of which are contemplated by the present invention.

Agents which modulate metabolic activity according to the above screening method are synthesized and optionally further qualified.

For example, in vivo models for metabolic diseases by which the agents of the present invention may be tested can be used. For example, Type I diabetes models include, pancreatectomy in dogs, spontaneous rodent models (e.g. BBDP rats and the NOD mice). Type II diabetes models and obese animal models include, db/db (diabetic) mice, Zucker diabetic fatty (ZDF) rats, sand rats (*Psammomys obesus*) and obese rhesus monkeys.

It will be appreciated that such agents can be used as pharmaceuticals.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of an AK005324 Conditional Knock-Out Mouse Model

The present inventor developed an AK005324 gene conditional knock-out (KO) mouse model. Using the general strategy illustrated in FIG. 3 and explained in detail herein, the development of the AK005324 constitutive and conditional KO mouse lines comprises the following steps:

1. Cloning and sequencing of the targeted region of the murine AK005324 locus in a 129/SvPas genetic background 2. Targeting vector and positive control vector design and construction 3. Set-up of the screening conditions for the detection of homologous recombination events, Cre-mediated and Flp-mediated excision events (PCR and Southern Blot)

4. Homologous recombination in ES cells

5. In vitro Flp-mediated excision of the Neomycin cassette

6. ES cell injection into blastocysts and generation of chimeras

7. Breeding to the F1 generation of chimeras with wild type animals and generation of heterozygous mutant carrying a floxed AK005324 allele.

Example 2

Mouse AK005324 Gene Characterization

Mouse AK005324 Locus

The mouse AK005324 gene is located on chromosome 16 and extends over 8 kb. The C57BL/6 mouse sequence is available on the ENSEMBL database (wwwdotensembldotorg, ENSMUSG00000035790).

ENSEMBL database search revealed that the AK005324 locus is flanked by one gene located very closely to AK005324 in 5' and one neighboring gene in 3', positioned further away (see FIG. 4). The phosphatidylinositol glycan, class X (GenBank Accession No. NM_024464) was found to be located at the 5' end of the AK005324 gene, on the complementary DNA strand (see FIG. 4). Phosphatidylinositol glycan, class X contains 6 exons. The ATG start codon is located in exon 4 and the stop codon in exon 6. The distance between phosphatidylinositol glycan, class X exon 1 and AK005324 exon 1 is 70 bp. This implies that the promoter region of each gene overlaps with that of the other gene. The leucine rich repeat containing 33 gene (GenBank Accession No. NM_146069) is located 34 kb at the 3' end of the AK005324 gene (see FIG. 4). The phosphatidylinositol glycan, class X gene is an ER-resident type I transmembrane enzyme involved in the transfer of glycosyl moieties into N-glycan, GPI-anchor precursors, and serine/threonine residues in many proteins.

Mouse AK005324 Gene Structure

The AK005324 mouse gene consists of 4 exons interrupted by 3 introns. The translation initiation site is located in exon 3 and the stop codon is located in exon 4 (see Table 1, below, and FIG. 5).

TABLE 1

Size of mouse AK005324 exons and introns

| Exon/intron number | Exon length (bp) | Intron length (bp) |
|---|---|---|
| 1 | 310 | 2855 |
| 2 | 78 | 839 |
| 3 | 164 (ATG) | 2858 |
| 4 | 1155 (STOP) | / |

Mouse AK005324 Protein

The mouse AK005324 gene is transcribed into a single mRNA species, which contains at least 1702 nucleotides (GenBank Accession No. NM_025892) and encodes a 163 amino-acids open reading frame. No splicing of the AK005324 mRNA has been previously described. Bioinformatics analysis revealed no specific sites or proteic domains in the AK005324 sequence.

Example 3

Strategy for the Development of AK005324 Conditional Knock-Out Model

Global Strategy for AK005324 Conditional Knock-Out

The present inventor employed the strategy of targeting the AK005324 exon 3. As described above, exon 3 encodes the methionine codon, initiator of AK005324 translation, together with the 43 AK005324 first amino acids. The structure of the targeted AK005324 locus is illustrated in FIG. 6.

Structure of the Targeting Vector

The design of the targeting vector is illustrated in FIG. 7 and displays the following features:

1. Homology arms isogenic with the ES cell line that will be used (129/SvPas)
2. Total homology with targeted allele around 8 kb
3. Insertion of a FRT-PGKpromoter-Neomycin-FRT-LoxP positive selection cassette in the intron 3 sequence. The FRT-flanked selection cassette can be removed in vitro using the Flp recombinase.
4. Insertion of the distal LoxP site in the intron 2 sequence.
5. Presence of the Diphteria Toxin A (DTA) negative selection marker.

Two different vectors were generated:

1. A positive control vector, displaying extended short homology arm. This latter vector reproduced the 3' junction between the final targeting vector and the endogenous AK005324 locus, allowing the setting up of an efficient and reliable PCR strategy for the screening of the homologous recombination.
2. The final targeting vector used for the homologous recombination phase in ES cells, which displayed reduced short homology arm when compared to the positive control vector.

The cloning and sequencing of the homology region, required for the construction of these two vectors and the global strategy for the construction of these two vectors is described detail Example 4, below.

Example 4

Cloning and Sequencing of the AK005324 Homology Region

Cloning of the Mouse AK005324 Homology Region

The first step of the present invention consisted of cloning of about 10 kb mouse genomic DNA fragment encompassing the AK005324 exons 1 to 3. This region was then used to generate the homology arms necessary for the construction of the targeting vector. The amplicon corresponding to the short homology arm presented an extended region that was present in the final targeting vector.

Three different sets of primers for the amplification of the long arm and extended short homology arm were designed. These primers were designed based on the C57BL/6 AK005324 gene full sequence (SEQ ID NO: 44). The primers used are presented in Table 2, below, and FIG. 8 depicts all of the primer locations as used by the present inventor.

TABLE 2

Sequences of the PCR primers used for the cloning of the long homology arm (LA amplicon)

| Primer name | Amplicon | Sequence |
| --- | --- | --- |
| SHA1-A1 | LA | 5'-TCTACTTCTGGCAGTACATCAGTGAGGC-3' (SEQ ID NO: 12) |
| SHA1-A2 | LA | 5'-AAGTGAGAGTGGGTGGGTAAGGGAGTGGG-3' (SEQ ID NO: 13) |
| SHA1-A3 | LA | 5'-TATGCCTCAGTACAGGGGAACGCCAGTGC-3' (SEQ ID NO: 14) |
| SHA1-B1 | LA | 5'-CTGCCTTAGCTGTCTACATTGCTTGG-3' (SEQ ID NO: 15) |
| SHA1-B2 | LA | 5'-CCTCCCCTTCCTTTTCCCTCTCAGTGG-3' (SEQ ID NO: 16) |
| SHA1-B3 | LA | 5'-TGGACCTTTGGAAGAGCAGTCGGGTGC-3' (SEQ ID NO: 17) |

TABLE 3

Sequences of the PCR primers used for the cloning of the extended short homology arm (eSA amplicon)

| Primer name | Amplicon | Sequence |
| --- | --- | --- |
| SHA1-C1 | eSA | 5'-TGAGAATGAAACCGAAGGAAAGAGCCGC-3' (SEQ ID NO: 18) |
| SHA1-C2 | eSA | 5'-GGGGAAAAGGTTTATTCAGCAGGTCC-3' (SEQ ID NO: 19) |
| SHA1-C3 | eSA | 5'-AGTCTCTGGTACGAATGCAGCACACTAAGG-3' (SEQ ID NO: 20) |
| SHA1-D1 | eSA | 5'-TGGCAGCCCACTCACATTGAAACATTCC-3' (SEQ ID NO: 21) |
| SHA1-D2 | eSA | 5'-CTTGGTGATTTCTGCTCCTGTGAGTAGC-3' (SEQ ID NO: 22) |
| SHA1-D3 | eSA | 5'-ACAAAAGGCACCCTCTATCCTCTTGAGC-3' (SEQ ID NO: 23) |

The following PCR conditions were used:

Taq/Pfu DNA polymerases: "Expand Long Template PCR system" kit (Roche diagnostics)

| eSA amplicon | LA amplicon |
| --- | --- |
| 94° C. for 2 min | 94° C. for 2 min |
| 94° C. for 30 s, | 94° C. for 30 s, |
| 65° C. for 30 s, | 65° C. for 30 s, |
| 68° C. for 3 min, | 68° C. for 7 min, |
| 15-20 cycles | 15-20 cycles |

The sizes of the different amplicons are presented in the Table 4 below.

TABLE 4

Sizes of the different homology region amplicons

| Primer set | Amplicon | Size of the amplified fragment |
|---|---|---|
| SHA1-C1/SHA1-D1 | eSA | 2721 bp |
| SHA1-C2/SHA1-D2 | eSA | 2634 bp |
| SHA1-C3/SHA1-D3 | eSA | 2860 bp |
| SHA1-A1/SHA1-B1 | LA | 6681 bp |
| SHA1-A2/SHA1-B2 | LA | 6994 bp |
| SHA1-A3/SHA1-B3 | LA | 6648 bp |

Sequencing of the Mouse AK005324 Homology Regions

The primer set SHA1-C1/SHA1-D1 gave the highest yield and specificity for the amplification of the extended short arm of homology, therefore this PCR product was sub-cloned into the pCR4-TOPO vector (Invitrogen) and 3 independent clones were generated.

The primer set SHA1-A1/SHA1-B1 gave the highest yield and specificity for the amplification of the long arm of homology, therefore this PCR product was sub-cloned into the pCR4-TOPO vector (Invitrogen) and 3 independent clones were generated.

These 6 clones were then entirely sequenced.

Extended Short Arm of Homology

The sequences obtained on 129/Sv genetic background were first aligned with each other to identify putative mutations introduced by the PCR amplification step.

One of the sequenced clones presented only 2 mutations in the whole-amplified region. Moreover, these two mutations were present in the extended arm region, which was not present in the final targeting vector. This clone was chosen for the following cloning steps.

The two other clones presented 3 mutations.

Then, the 129Sv sequences generated were aligned with the C57Bl/6 sequence available in public database. This allowed the present inventor to determine the polymorphism between the C57Bl/6J and 129Sv strains in the region of interest. This alignment suggested that the polymorphism rate within the 2721-bp extended short arm of homology region is null.

Long Arm of Homology

A similar strategy was followed for the analysis of the long arm homology region.

The three sequenced clones (#A10, #B6 and #C6) displayed respectively 3, 2 and 3 mutations in the whole-amplified region. The clone #B6 displayed only one mutation in the AflIII/AspI region, that was used as long homology arm.

Furthermore, it is possible to substitute the mutated region present in the #B6 clone with the non-mutated fragment isolated from the #A10 clone. This single extra NsiI/HindIII restriction cloning step is currently in progress.

Then, the 129Sv sequences generated were aligned with the C57Bl/6 sequence available in public database. This allowed the present inventor to determine the polymorphism between the C57Bl/6J and 129Sv strains in the region of interest. This alignment suggested that the polymorphism rate within the long arm of homology is null.

Thus, the present inventor was successful in amplifying, cloning and sequencing the two arms of homology needed for the generation of the AK005324 targeting vector.

Two mutations were introduced by the PCR amplification step into the extended short arm of homology fragment. These two mutations were located in the extended region, which was not present in the final targeting vector.

The sequencing of two LA clones indicated that one mutation was introduced by the PCR amplification step.

Example 5

Construction of the AK005324 Targeting and Positive Control Vectors

The present inventor constructed the vectors based on the knowledge that (1) it is crucial to limit the size of the floxed region and (2) it is essential to preserve as much as possible the splicing of AK005324 introns 2 and 3. It was considered that loxP sites and selection cassettes should be positioned at least 50 bp apart of the splicing recognition sites. Therefore, the ideal design was to localize the distal loxP site 50 bp upstream of the intron 2 acceptor splice site and the positive selection cassette containing the proximal loxP site 50 bp downstream of the intron 3 donor splice site. The size of the floxed region was thus in the range of 250 to 300 bp.

The AK005324 locus sequence was analyzed in C57Bl/6 genetic background in order to identify restriction sites that could be used for the construction of the vectors. As shown in FIG. 9, an XbaI restriction site was found to be located 85 bp downstream of AK005324 exon 3. The extended short arm could then be isolated as a 2063 bp XbaI/NheI restriction fragment and the short arm could be isolated as a 1687 bp XbaI/ScaI restriction fragment.

However, a useful restriction site located upstream and sufficiently close to exon 3 was not identified. This unique site was required for the insertion of the distal loxP site. To circumvent this issue, insertion of the LoxP sequence was introduced into a synthetic oligonucleotide. This approach presented the advantage of allowing the insertion of the distal loxP site at the position of choice, 50 bp upstream of exon 3. The synthetic oligonucleotide covered the AspI/XbaI 856 bp region, encompassing exon 3 sequence. The long arm could be isolated as a 6127 bp AflIII/XbaI restriction fragment.

Global Strategy

The cloned mouse AK005324 long and short arms of homology were used for the construction of the AK005324 conditional knock-out targeting vector. The global strategy for the targeting vector and positive control vector were subdivided into two major issues:

1. Initial constructions: modified linkers, positive control
2. Targeting vector construction All the cloning steps are schematically illustrated in the FIGS. 10 and 11.

First Constructions

Three plasmids were constructed in parallel at the first stage of the development (circled numbers depicted in FIG. 10).

Step 1: a 86-bp synthetic oligonucleotide comprising the KpnI, AscI, PmlI, NruI, AspI, NheI, PstI, AatII, FseI, SwaI, NotI and SacI restriction sites was KpnI-SacI sub-cloned into the pCR-script plasmid. The sequence of this oligonucleotide is presented in Table 5, below. The 2945-bp resulting plasmid is referred to hereon as SHA1-linker.

TABLE 5

Sequences of the oligonucleotide used to create the SHA1-linker plasmid

| Primer name | Sequence |
|---|---|
| PCR-script-LA | 5'CGGCGCGCCACACGTGATCGCGATGACCT<br>GGTCAGCTAGCACTGCAGAGACGTCAGGCCG |

TABLE 5-continued

Sequences of the oligonucleotide used to create
the SHA1-linker plasmid

| Primer name | Sequence |
|---|---|
| | GCCTATTTAAATTGCGGCCGCGAGCT3'
(SEQ ID NO: 24) |

Step 2: a 916-bp synthetic oligonucleotide comprising respectively of the XhoI and AspI restrictions sites, the 34-bp LoxP sequence, the 3' part of intron 2, the exon 3, the 5' part of intron 3 and the XbaI and SacI restriction sites was KpnI-SacI sub-cloned into the pCR-script plasmid. The sequence of this oligonucleotide is presented in Table 6, below. The 3786-bp resulting plasmid is referred to hereon as SHA1-synthetic-LA.

TABLE 6

Sequences of the oligonucleotide used to create
the SHA1-synthetic LA plasmid

| Primer name | Sequence |
|---|---|
| PCR-script-LA | 5'TGGTCTAGTGGACTTCTCAACACTAAATGTTTATAAAATCA
AAAGTACTGGGGGTGTGGCATAGCCAGTGCAGTGCTTGCCTGTTATG
CTTGAAGCCCTGGGTTCCATCTTGAGCAAGCCCTAAACCAAGGTTAG
TAGCACATACTGTAATTCTAACACTGGCAAATAGAGACAGGAGGAT
CAGAAATCCAGGGTCATCCTCCACTCCATAACAAATTCAAAGCCAAT
CTGGACCACATGAGATACTGTCTGGAAAAAGGAAAAAGTTTAAAGG
AACAAAGAGGCTGAATCAGAGATCCTTTAGCTGAAACATCAAATTA
TTCTGAAGGCCAGCCGGTCAGTTCTTGGGCTCCCAGGAGGTCAGTGT
GTAGTCTCTGGTACGAATGCAGCACACTAAGGGGTCCAGGCCGAAT
GTCATTACCGACTCAGAGATCCAACGAACTGAGTCAAACCTAGACC
AAGACTCACACTGTGTAAGGATACAATCCTGGGGCTAGTCCACAGC
CAGACCCACGGAGGAGAAGGGGAAAAGGTTTATTCAGCAGGTCCCT
CGATTATGCATGATAACTTCGTATAATGTATGCTATACGAAGTTATT
GGTTGTTCTTCTTCAGGAAATTGTTGTACAACTGTCCTATTTGTATCA
GGTTTCTTCCAGTTTACCCTGAGTTACACGAGAAGATGAAATACATT
GCCAAGAAATGTGGAGTTAGGTTCCAGCCTCCAGCTGTGATCTTGAT
TTATGAGAATGAAACCGAAGGAAAGAGCCGCCAGCGTATCATGCCT
GTCCGAAACTTTTCAAAGTTCTCAGGTACCCCTTGTTTTATCTTGCCT
CCTGTCTAGTTCTCTATTTATTTTTATTTATGTATGTATGTATGTGTCT
ATGTGCGTGGGTGT-3'
(SEQ ID NO: 25) |

Step 3: corresponds to the creation of the positive control vector. This step was performed by ligation of a 2062-bp XbaI/NheI fragment isolated from the SHA1-TOPO-SA-4 into the genOway's plasmid containing the FRT-PGK-neo-FRT-LoxP positive selection cassette plasmid restricted using AvrII. The 6761-bp resulting plasmid is referred to hereon as SHA1-C+.

Construction of the Targeting Vector

The construction of the targeting vector is illustrated in detail in FIG. 11 and the corresponding cloning steps are described below.

Step 4: corresponds to the sub-cloning of the corrected LA amplicon into the SHA1-linker plasmid. This step was performed by ligation of a 5012-bp BsaAI/AspI fragment containing the LA isolated from the SHA1-TOPO-LA plasmid into the SHA1-linker plasmid restricted using NruI/AspI. The 7949-bp resulting plasmid is referred to hereon as SHA1-LA.

Step 5: corresponds to the sub-cloning of the SHA1-synthetic LA fragment into the SHA1-LA plasmid. This step was performed by ligation of a 897-bp AspI/XbaI fragment containing the SHA1-synthetic LA isolated from the SHA1-synthetic LA plasmid into the SHA1-LA plasmid restricted using AspI/NheI. The 8839-bp resulting plasmid is referred to hereon as SHA1-LA-LoxP.

Step 6: corresponds to the shortening of the extended short arm and ligation of the resulting SA into the LA-LoxP sequence. This step was performed by ligation of a FseI/ScaI 3770-bp fragment isolated from the SHA1-C+ plasmid into the SHA1-LA-LoxP plasmid restricted using FseI/SwaI. The 12302-bp resulting plasmid is referred to hereon as SHA1-LSA-neo.

Step 7: corresponds to the insertion of the DTA negative selection cassette. This step was performed by ligation of a 3437-bp AscI/EcoRV fragment isolated from genOway's G112 validated plasmid into the SHA1-LSA-neo plasmid restricted by AscI/PmlI. The 15725-bp resulting plasmid is referred to hereon as SHA1-HR.

The targeting vector displayed the following features:
1. Homology arms isogenic with the ES cell line that was used (129/SvPas)
2. Insertion of two loxP sites flanking AK005324 exon 3
3. Short arm of homology of 1.7 kb
4. Long arm of homology of 5.9 kb
5. Presence of a NsiI diagnostic restriction site close to the distal LoxP site
6. Positive selection neomycin gene flanked by FRT sites. The FRT-flanked selection cassette could be removed in vitro using the Flip recombinase or in vivo by breeding with Flip-expressing mice.
7. Presence of the Diphteria Toxin A (DTA) negative selection marker.

Sequencing of the SHA1-HR Targeting Vector

As a final quality control step, the SHA1-HR targeting vector was validated through partial sequencing. The following elements of the vector were sequenced:
1. The AK005324 exon 3
2. The two LoxP sites, including the NsiI diagnostic restriction site
3. The FRT-neo-FRT cassette
4. All the junctions between the different cloned fragments All these elements displayed correct sequences and orientation, demonstrating the validity of the SHA1-HR targeting vector.

Example 6

PCR Screening Procedures

3' PCR Screening for the Detection of the Homologous Recombination Event

It was crucial to devise screening strategies allowing a quick and unequivocal identification of the homologous recombination event in ES cells.

A PCR screening using primers external to the targeting vector and primers hybridizing the Neomycin selection marker was designed for detection of 3' end homologous recombination event (FIG. 12).

In order to obtain a screening allowing the detection of the homologous recombination event in the 3' arm of homology, the present inventor designed three external primers (GX2587, GX2588 and GX2589) and three neomycin primers (GX1406, GX1528 and GW781). The forward primers (GX1406, GX1528 and GW781) were located into the Neo selection cassette. The reverse primers (GX2586, GX2588 and GX2589) were located downstream of the 3' end of the targeting vector and were present in the 3' portion of the positive control vector (SHA1-C+).

Primers location are depicted in FIG. 12 and primer sequences are presented in Table 7, below.

TABLE 7

Sequences of the PCR primers used for 3' screening

| Primer name | Amplicon | Sequence |
|---|---|---|
| GX1406 | 3' screen | 5'-CTACTTCCATTTGTCACGTCCTGCACG-3' (SEQ ID NO: 26) |
| GX2587 | 3' screen | 5'-CTGGATTTGGAAGACGGCTGTGAGC-3' (SEQ ID NO: 27) |
| GX1528 | 3' screen | 5'-CCAGTCATAGCCGAATAGCCTCTCC-3' (SEQ ID NO: 28) |
| GX2588 | 3' screen | 5'-AGCATTAGGAGGCTGAAGCAGGAGG-3' (SEQ ID NO: 29) |
| GW781 | 3' screen | 5'-ATGTGGAATGTGTGCGAGGCCAGAG-3' (SEQ ID NO: 30) |
| GX2589 | 3' screen | 5'-CATATGTGCAGTGCTGGCAGAGACC-3' (SEQ ID NO: 31) |

The different combinations of primers were tested in order to identify the PCR conditions displaying best specificity and sensitivity. The sizes of the different amplicons are indicated in Table 8A, below.

TABLE 8A

Size of the different 3' amplicons

| Primers | Amplicon | Size (bp) |
|---|---|---|
| GX1406/GX2587 | 3' screen | 2108 |
| GX1528/GX2588 | 5' screen | 2674 |
| GW781/GX2589 | 5' screen | 2030 |

The present inventor used the following PCR conditions (see Table 8B, below): Taq/Pfu DNA polymerases: "Expand Long Template PCR system" kit (Roche diagnostics).

TABLE 8B

PCR conditions
Reaction conditions: 3' screening

| Step | Temp. | Time | Cycles |
|---|---|---|---|
| Denaturing | 94° C. | 2 min | 1x |
| Denaturing | 94° C. | 30 s | |
| Annealing | 65° C. | 30 s | 35x |
| Extension | 68° C. | 3 min | |

Validation of the 3' End PCR Screening Using the SHA1-C+ Plasmid

The three sets of primers described above were first tested on serial dilutions of the positive control vector SHA-C+ spiked into genomic DNA extracted from C57/Bl/6J mouse tail biopsies. This protocol was established to test the specificity of the primers pairs together with the sensitivity of the different PCR reactions. As illustrated in FIG. 13, showing representative examples of these tests, the best sensitivity was achieved with the GX781/GX2589 primer set. This PCR reaction allowed the detection of the SHA1-C+ targeting vector/AK005324 locus 3' junction at a sensitivity of 0.1 genomic equivalent copy (lanes 1 and 5 in FIG. 13). Since one copy of the transgene diluted in the whole mouse genome would be the lowest ratio observed in recombinant ES cells, these 3' PCR conditions were relevant for the screening of targeted ES cell clones. In addition, this PCR reaction was highly specific since no signal was observed on genomic DNA extracted from ES cells (see lane 9 in FIG. 13). In order to further validate the 3' PCR screening in conditions similar to ES cells screening, the primer set was tested on genomic DNA extracted from ES cells clones stably transfected of the SHA1-C+ vector.

As presented in FIG. 14, showing representative examples of these tests, the PCR reaction allowed the detection of the SHA1-HR targeting vector/AK005324 locus 3' junction with good sensitivity. Since these conditions mimicked the SHA1-HR targeting vector/AK005324 locus 3' junction in the proper genomic environment, the present inventor considered that these 3' PCR conditions were validated for the screening of targeted ES cell clones.

In Vitro Validation of FRT and LoxP Sites Functionality

In order to validate the functionality of both loxP and FRT sites present in the targeting construct, Cre-expressing and Flip-expressing E coli bacterial strain were transformed with the SHA1-HR targeting vector. PCR were then performed on transformed colonies from both strains. The present inventor designed one forward primer (GX2592) located upstream of the distal loxP site and one reverse primer (GX2593), located upstream of the neomycin selection cassette (see FIG. 15). Primers location are depicted in FIG. 15 and primer sequences are presented in Table 9, below.

TABLE 9

Sequences of the PCR primers used to validate the FRT and loxP sites functionality

| Primer name | Amplicon | Sequence |
|---|---|---|
| GX2592 | Sites valid. | 5'-CTGGACCACATGAGATACTGTCTGG-3' (SEQ ID NO: 32) |
| GX2593 | Sites valid | 5'-GGTCTGCTACAGATCAGTCTGTTGG-3' (SEQ ID NO: 33) |

Expected Fragment Size:

3318 bp on the SHA1-HR vector 1645 bp on the Flp-treated SHA1-HR vector 1231 bp on the on the Cre-treated SHA1-HR vector As indicated in FIG. 16, showing representative examples of the PCR, the PCR described above allowed the amplification of fragments of correct sizes when performed on five independent Cre-expressing colonies (lanes 1 to 5), and Flp-expressing colonies (lanes 6 to 10). These results clearly indicate that the LoxP and FRT sites present in the SHA1-HR targeting vector are fully functional.

PCR Screening Strategy for the Flip-Mediated Excision of the Neomycin Positive Selection Cassette and Cre-Mediated Excision of the Foxed Region The PCR strategy used for detection of the Flip-mediated excision of the neomycin positive selection cassette and Cre-mediated excision of the floxed region is illustrated in FIG. 17. This screening strategy was also used for the genotyping of F1 heterozygous and F2 homozygous animals.

The present inventor designed a reverse external primer (GX2594) located downstream of the neomycin selection cassette and external of the targeted region and one forward internal primer (GX2587), located upstream of the distal loxP site (see FIG. 17). Sequences of these primers are presented in Table 10A below.

TABLE 10A

Sequences of the PCR primers used for Flp-mediated and Cre-mediated excisions screening

| Primer name | Amplicon | Sequence |
|---|---|---|
| GX2594 | Recombinase | 5'-CTTGGGGCTTCAACTGCTACTGTCAGG-3' (SEQ ID NO: 34) |
| GX2587 | Recombinase | 5'-CTGGATTTGGAAGACGGCTGTGAGC-3' (SEQ ID NO: 35) |

The following PCR conditions were used (see Table 10B, below):

Taq/Pfu DNA polymerases: "Expand Long Template PCR system" kit (Roche diagnostics).

TABLE 10B

PCR conditions
Reaction conditions: 3' screening

| Step | Temp. | Time | Cycles |
|---|---|---|---|
| Denaturing | 94° C. | 2 min | 1x |
| Denaturing | 94° C. | 30 s | |
| Annealing | 65° C. | 30 s | 35x |
| Extension | 68° C. | 4 min | |

Expected Fragment Size:

3676 bp on the WT locus 5526 bp on the targeted locus 3853 bp on the Flp-treated locus 3439 bp on the Cre-treated locus As presented in FIG. 18, showing representative examples of the PCR, the PCR conditions described above allowed amplification of the 3676-bp amplicon from genomic DNA extracted from WT ES cells and C56Bl/6 mouse tail biopsy (lanes 1 and 2 in FIG. 18).

Example 7

Southern Blot Validation

Global Strategy for Southern Blot Screening of the Homologous Recombination Event The integrity of both 5' and 3'end regions of the targeted AK005324 locus were next confirmed by Southern blot.

Probes locations as well as restriction sites are indicated in FIGS. 19 and 20.

5' Southern Blot Validation

Generation of the 5' Southern Blot Probe

The 485-bp 5' probe internal N was a HindIII/SphI fragment generated by restriction of the SHA1-TOPO-LA-B6 clone.

Southern Blot Validation of 5' Targeting Event:

Southern blot screening strategy validating the 5' end homologous recombination was based on a EcoNI/SwaI digestion of the genomic DNA and detection using the 485-bp 5' probe internal N (see FIG. 21).

Wild type genomic DNA digested by EcoNI/SwaI and hybridized with 5' probes gave a 7.0 kb band, while recombined genomic DNA was expected to give a 8.1 kb band. The same probe was used to detect a 6.5 kb band, after Flp-mediated excision of the neomycin cassette and a 6.0 kb band after Cre-mediated excision of the floxed region (see FIG. 21).

Southern blots were set up on wild type genomic DNA in order to validate probe specificity before proceeding to the confirmation screening itself.

As presented in FIG. 21, the expected 7.0 kb band was observed after EcoNI/SwaI digestion of WT ES cell genomic DNA and hybridisation with the 5' N probe. This result validated the 5' end Southern blot strategy.

3' Southern Blot Validation

Generation of the 3' Southern Blot Probe

The 3' Southern blot external probe was generated by PCR amplification on 129/SvPas genomic DNA. PCR products were subcloned, amplified, and purified for the Southern blot experiment. Sequences of these primers are presented in the Table 11 below.

TABLE 11

Sequences of the PCR primers used for 3' Southern blot probes generation.

| Primer name | Amplicon | Size | Sequence |
|---|---|---|---|
| GX2597 | 3' probe R | 645 bp | 5'-GATTTGTAAACCCCGTCAGCCAGT GG-3' (SEQ ID NO: 36) |
| GX2598 | 3' probe R | 645 bp | 5'-TGTCAACGCCTTGAAGGCAGATTC C-3' (SEQ ID NO: 37) |

Southern Blot Validation of 3' Targeting Event:

Southern blot screening strategy validating the 3' end homologous recombination was based on a NsiI digestion of the genomic DNA. Detection was performed using a 645-bp 3' external probe (see FIG. 22).

Wild type genomic DNA digested by NsiI and hybridized with 3' probe gave a 9.5-kb band, while recombined genomic DNA was expected to give a 8.5-kb band. The same probes were used to detect a 6.8-kb band, after Flp-mediated excision of the neomycin cassette and a 6.4-kb band after Cre-mediated excision of the floxed region (see FIG. 22).

Southern blots were set up on wild type genomic DNA in order to validate probe specificity before proceeding to the confirmation screening itself. As presented in FIG. 22, the expected 9.5 kb band was observed after NsiI digestion of WT ES cell genomic DNA and hybridisation with the 3' R probe. This result validated the 3' end Southern blot strategy.

So far, the results of the present invention showed the development of a AK005324 conditional knock-out mouse line comprising insertion of two loxP sites at the AK005324 locus, flanking AK005324 exon 3. The present inventor was successful in amplifying, cloning and sequencing the two arms of homology needed for the generation of the AK005324 targeting vector and succeeded in constructing the targeting and positive control vectors. Furthermore, the present inventor designed PCR and Southern blot screening strategies to identify ES cell clones displaying correct homologous recombination at the AK005324 locus. The 3' PCR screening together with the 5' and 3' Southern blot conditions were demonstrated as being specific and sensitive enough to allow the detection of targeted ES cell clones at the level of one copy per genome.

Example 8

Homologous Recombination in ES Cells and Screening of Targeted Clones

SHA1-HR Targeting Vector Preparation

The recombinant SHA1-HR plasmid was amplified and purified by the standard Qiagen midi prep method. Digestions of aliquots of the amplified circular DNA were performed with different restriction enzymes resulting in the appropriate DNA fragments. The SHA1-HR plasmid was linearised by NotI. The fragment was purified by phenol/chloroform extraction and ethanol precipitation. This preparation was used for the electroporation of ES cells.

Homologous Recombination in ES Cells

Using the SHA1-HR targeting vector, one electroporation session was performed in genOway's 129/Sv derived embryonic stem cells, according to genOway' standard procedure (260 Volt, 500° F., 5.10$^6$ cells for 40 µg of linearised DNA). G418 selection was started 48 hours after electroporation, by addition of 200 µg/ml of G418. 190 G418-resistant clones were isolated and amplified in 96-well plates in duplicate. The duplicate set of ES cell clone amplified on gelatine was used for identification of the homologous recombination event. The template of frozen ES cell clones was kept at −80° C. for further amplification of positive clones.

3' PCR Screening for Homologous Recombination Event

The screening of the 190 G418-resistant clones was done, using the 3' PCR strategy previously designed and validated. FIG. 23 illustrates the position of the PCR primers and sizes of the amplicons used to screen for the 3' homologous recombination event. The positive control vector, used to set up these PCR, is also depicted.

The 3' PCR screening was based on the amplification of a 2030 bp fragment using the GW781/GX2589 primers set. The forward primer (GW781) was located into the Neo selection cassette. The reverse primer (GX2589) was located downstream of the 3' end of the targeting vector and is present in the 3' portion of the positive control vector (SHA1-C+). Sequences of the primers are presented in the Table 12A, below.

TABLE 12A

Sequences of the PCR primers used for 3' screening

| Primer name | Amplicon Sequence |
|---|---|
| GW781 | 3' screen 5'-ATGTGGAATGTGTGCGAGGCCAGAG-3' (SEQ ID NO: 38) |
| GX2589 | 3' screen 5'-CATATGTGCAGTGCTGGCAGAGACC-3' (SEQ ID NO: 39) |

The following PCR conditions were used:

Taq/Pfu DNA polymerases: "Expand Long Template PCR system" kit (Roche diagnostics)

TABLE 12B

PCR conditions
Reaction conditions: 3' screening

| Step | Temp. | Time | Cycles |
|---|---|---|---|
| Denaturing | 94° C. | 2 min | 1x |
| Denaturing | 94° C. | 30 s | |
| Annealing | 65° C. | 30 s | 35x |
| Extension | 68° C. | 3 min | |

3' PCR screening using these conditions revealed 8 positive clones out of 190 displaying an amplified fragment at the expected size (2030 bp). Representative example of this screening is illustrated in FIGS. 24A-B.

These PCR results were reproduced (see FIG. 25) and demonstrated that the 8 ES cell clones termed #4A3, #5A5, #3B7, #1A11, #4A2, #1B9, #2A8, and #3B4 displayed a correct targeting event at the 3' end of the AK005324 locus.

PCR Screening for the Detection of the Distal LoxP Site

The presence of the distal loxP site was monitored in the 8 ES cell clones positive for the 3' PCR using the 5' PCR strategy previously designed.

The set of primers GX2590/GX2591 was used. The forward primer (GX2590) was located upstream of the AKOO5324 gene. The reverse primer (GX2591) was located downstream of the distal LoxP site, and internal to the targeted region (see FIG. 26). Sequences of the primers are presented in Table 13A, below.

TABLE 13A

Sequences of the PCR primers used for the detection of the distal LoxP site

| Primer name | Amplicon Sequence |
|---|---|
| GX2590 | 5' screen 5'-ACTGGAGTCGGCTTGTCAGCTTTCC-3' (SEQ ID NO: 40) |
| GX2591 | 5' screen 5'-AAGATCACAGCTGGAGGCTGGAACC-G-3' (SEQ ID NO: 41) |

The following PCR conditions were used (see Table 13B, below):

Tag DNA polymerase from the "Expand Long Template PCR system" kit (Roche diagnostics)

TABLE 13B

| PCR conditions | | |
|---|---|---|
| Reaction Mix | | |
| genomic mouse DNA | 150.0 | ng |
| Primer | 10 | pmol |
| dNTPs | 0.2 | mM |
| Reaction Buffer/15 mM MgCl$_2$ | 0.1 | Vol |
| Taq Polymerase | 1.5 | U |
| Reaction Volume | 50.0 | µl |

| Reaction conditions | | | |
|---|---|---|---|
| Step | Temp. | Time | Cycles |
| Denaturing | 94° C. | 420 s | 1x |
| Denaturing | 94° C. | 30 s | |
| Annealing | 65° C. | 30 s | 35x |
| Extension | 68° C. | 7 min | |
| Completion | 68° C. | 300 s | 1x |

The expected size for this PCR product was 6057 bp for the wild-type allele and 6097 bp for the targeted allele. A representative example of this PCR screening performed on the 8 ES cell clones positive for the 3' screening is illustrated in FIG. 27. The PCR products described above were then sequenced in order to validate the presence of the distal loxP site. The presence of the distal loxP site was demonstrated by the presence of a double sequencing signal corresponding to both the wild type and recombinant alleles. This double signal starts after the genomic sequence immediately downstream of the expected loxP site integration site. If the GX2590/GX2591 amplicon contains only the wild type allele, this indicates absence of the distal LoxP site, and a single sequencing signal should be observed. The direct sequencing of the 8 GX2590/GX2591 PCR products amplified from the ES cell clones #4A3, #5A5, #3B7, #1A11, #4A2, #1B9, #2A8, and #3B4 indicated that the distal LoxP site was present in all sequenced amplicons. Representative examples of the electrophoregrams obtained after sequencing of the GX2590/GX2591 amplicon from ES cell clones #1A11 and #4A3 are illustrated in FIGS. 28A-B.

Southern Blot

The integrity of both 5' and 3'end regions of the targeted AK005324 locus was then confirmed by Southern blot in the 8 ES cell clones positive in the 3' and 5' PCR screenings (#4A3, #5A5, #3B7, #1A11, #4A2, #1B9, #2A8, and #3B4). The locations of the probes as well as restriction sites are indicated in FIGS. 29 and 30. As presented in FIG. 29, Southern blot screening strategy validating the 5' end homologous recombination was based on a EcoNI/SwaI digestion of the genomic DNA and detection using the 485-bp 5' N probe internal. Wild type genomic DNA digested by EcoNI/SwaI and hybridized with 5' probes gave a 7.0-kb band, while recombined genomic DNA was expected to give a 8.1 kb band. The same probes were later used to detect a 6.4 kb band, after Flp-mediated excision of the neomycin cassette and a 6.0 kb band after Cre-mediated excision of the floxed region (FIG. 30). As presented in FIG. 30, Southern blot screening strategy validating the 3' end homologous recombination was based on a NsiI digestion of the genomic DNA. Detection was performed using a 645-bp 3' external probe.

Wild type genomic DNA digested by NsiI and hybridized with 3' probe gave a 9.5 kb band, while recombined genomic DNA was expected to give a 8.5 kb band. The same probes were used to detect a 6.8 kb band, after Flp-mediated excision of the neomycin cassette and a 6.4-kb band after Cre-mediated excision of the floxed region (see FIG. 30).

5' and 3' Southern blotting analysis of the ES cell clones #4A3, #5A5, #3B7, #1A11, #4A2, #1B9, #2A8, and #3B4 are presented in FIGS. 31 and 32, respectively. As presented in FIG. 31, 5' Southern blot of the ES cell clones #4A3, #5A5, #3B7, #1A11, #4A2, #1B9, #2A8, and #3B4 (FIG. 31, lanes 2 to 9) revealed the expected wild type and recombined signals (see arrows in FIG. 31) at 7.0 kb and 8.1 kb, respectively. This result validated the homologous recombination event at the 5' end of the AK005324 locus for these 8 ES cell clone. Moreover, as presented in FIG. 32, 3' Southern blot of the ES cell clones #4A3, #5A5, #3B7, #1A11, #4A2, #1B9, #2A8, and #3B4 (FIG. 32, lanes 2 to 9) revealed the expected wild type and recombined signals (see arrows in FIG. 32) at 9.5 kb and 8.5 kb, respectively. This result validated the homologous recombination event at the 3' end of the AK005324 locus for these 8 ES cell clone.

Combining the results of 5' and 3' end Southern blot, the present inventor identified 8 ES cell clones fully validated for both 5' and 3' end targeted events: the ES cell clones #4A3, #5A5, #3B7, #1A11, #4A2, #1B9, #2A8, and #3B4.

Thus, the present inventors were capable of developing a AK005324 conditional knock-out mouse line. The strategy for AK005324 gene cloning, targeting vector construction and screening set-up and validation for the detection of the homologous recombination, Flip-mediated and CRE-mediated excision events have been presented.

Following SHA1-HR targeting vector electroporation, 190 G418 resistant clones were isolated and amplified in 96-well plates in duplicate. PCR screening at 3' end revealed 8 ES clones (#4A3, #5A5, #3B7, #1A11, #4A2, #1B9, #2A8, and #3B4) displaying the 3' end targeting event. The targeting event of these 8 ES cell clones was further validated through partial sequencing of the distal LoxP site region and by 5' and 3' southern blot.

Combining the PCR screenings, the sequencing results together with those of 5' and 3' end Southern blot, the present inventor then identified 8 ES cell clones (#4A3, #5A5, #3B7, #1A11, #4A2, #1B9, #2A8, and #3B4) fully validated for both 5' and 3' end targeted events. Two ES cell clones were next selected for blastocyst injection sessions, based on cell morphology and growth rate.

Example 9

Recombinant ES Cell Blastocyst Injections and Generation of Chimeras

Injection Sessions

Recipient blastocysts were isolated from pregnant C57BL/6 females (Health status SPF—Specific Pathogens free). ES cell clones #3B4, #3B7, #4A3 and #5A5 were injected into blastocysts. Injected blastocysts were then re-implanted into OF1 pseudo gestational females (Health status SOPF—Specific and Opportunist Pathogens Free). Table 14, below, summarizes the results obtained from the injection sessions.

Chimeras

Clone #3B4 gave rise to 11 pups, among which 6 chimeras were identified: 2 male chimeras with a percentage of chimerism of 40% and 5% and 4 female chimeras with a percentage chimerism ranging from 10% to 30%.

Clone #3B7 gave rise to 8 pups, among which 4 chimeras were identified: 2 male chimeras with a percentage of chimerism of 70% and 50% and 2 female chimeras with a percentage of chimerism of 15% and 20%.

Clone #5A5 gave rise to 5 pups, among which 4 chimeras were identified: 4 male chimeras with a percentage of chimerism ranging from 50% to 98%.

TABLE 14 results of the ES cell blastocyst injection sessions performed.

| Session | Clone no. | Injected blastocysts | Foster mothers reimplanted | Pregnant foster mothers | No. of pups | Still born | Male chimeras (% chimerism) | Female chimeras (% chimerism) |
|---|---|---|---|---|---|---|---|---|
| #1 Jun. 01, 2006 | #3B4 | 24 | 2 | 2 | 11 | 0 | 2 (40% and 5%) | 4 (10%, 10%, 20%, 30%) |
| #2 Jun. 01, 2006 | #3B7 | 24 | 2 | 2 | 8 | 0 | 2 (70% and 50%) | 2 (15% and 20%) |
| #3 Jun. 01, 2006 | #4A3 | 24 | 2 | 0 | 0 | 0 | 0 | 0 |
| #4 Jun. 01, 2006 | #5A5 | 24 | 2 | 1 | 5 | 0 | 4 (50% 90%, 95% and 98%) | 0 |

Table 14: Results from ES cell clones #3B4, #3B7, #4A3 and #5A5 blastocyst injections Based on the ES cell screening results, the present inventor selected four ES cell clones, namely #3B4, #3B7, #4A3 and #5A5, for blastocyst injections. These ES cell clones were injected and re-implanted into a total of 96 blastocysts, giving rise to a total of 14 chimeras with the following rate of chimerism:

ES cell clone #3B4: 6 chimeras (1 male at 40% chimerism, 1 male at 5%, 2 females at 10%, 1 female at 20%, 1 female at 30%).

ES cell clones #3B7: 4 chimeras (1 male at 50% chimerism, 1 male at 70%, 1 female at 15%, 1 female at 20%).

ES cell clones #5A5: 4 chimeras (1 male at 50% chimerism, 1 male at 90%, 1 male at 95%, 1 male at 98%).

The high rate of chimerism observed in most of the chimeras confirmed the quality of the ES cell line that was used.

Example 10

Breeding to F1 Generation with WT Mice and Generation of Heterozygous Mutant Carrying a Floxed AK005324 Allele Breeding of the Chimeras The male chimera generated from the ES clone #3B4 (displaying 60% chimerism) was mated with two WT C57BL/6J females (health status SOPF—Specific and Opportunist Pathogen Free).

The male chimera generated from the ES clone #3B7 (displaying 70% chimerism) was mated with two WT C57BL/6J females (health status SOPF—Specific and Opportunist Pathogen Free).

The two male chimeras generated from the ES clone #5A5 (displaying 95% and 98% chimerism) were mated with two WT C57BL/6J females each (health status SOPF—Specific and Opportunist Pathogen Free).

The results of chimera breeding are shown in Table 15 below.

TABLE 15

The results of chimera breeding

| Parental Chimera | Pups | No. of Agouti mice | Sex of F1 Litters | Mice cat. | Genotyping results (Heterozygote) |
|---|---|---|---|---|---|
| 60% male chimera (ES cell clone #3B4) | 7 | 0 | N/A | N/A | N/A |
| 70% male chimera (ES cell clone #3B7) | 8 | 5 | 4 males 1 female | #34457 #34754 to #34756 #34757 | #34457 |
| 95% male chimera (ES cell clone #5A5) | 0 | N/A | N/A | N/A | N/A |
| 95% male chimera (ES cell clone #5A5) | 0 | N/A | N/A | N/A | N/A |

N/A: Non applicable.

PCR Screening and Identification of Conditional KO F1 Mice

The F1 agouti mouse #34457 obtained from the breeding with WT female were screened using the 3' PCR strategy previously designed and validated FIG. 33 presented below illustrates the position of the PCR primers and sizes of the amplicons that were used to screen for the 3' homologous recombination event. The positive control vector, used to set up these PCR, is also depicted.

The 3' PCR screening was based on the amplification of a 2030 bp fragment using the GW781/GX2589 primers set. The forward primer (GW781) was located into the Neo selection cassette. The reverse primer (GX2589) was located downstream of the 3' end of the targeting vector and was present in the 3' portion of the positive control vector (SHA1-C+). Sequences of the primers are presented in the Table 16A, below.

TABLE 16A

Sequences of the PCR primers used for 3' screening

| Primer name | Amplicon | Sequence |
|---|---|---|
| GW781 | 3' screen | 5'-ATGTGGAATGTGTGCGAGGCCAGAG-3' (SEQ ID NO: 42) |
| GX2589 | 3' screen | 5'-CATATGTGCAGTGCTGGCAGAGACC-3' (SEQ ID NO: 43) |

The inventor used the following PCR conditions (see Table 16B, below):
Taq/Pfu DNA polymerases: "Expand Long Template PCR system" kit (Roche diagnostics)

TABLE 16B

PCR conditions
Reaction conditions: 3' screening

| Step | Temp. | Time | Cycles |
|---|---|---|---|
| Denaturing | 94° C. | 2 min | 1x |
| Denaturing | 94° C. | 30 s | |
| Annealing | 65° C. | 30 s | 35x |
| Extension | 68° C. | 3 min | |

3' PCR screening using these conditions revealed one positive tail biopsy displaying an amplified fragment at the expected size (2030-bp). Representative example of this screening is illustrated in FIG. 34.

As presented in FIG. 34, the 3' PCR screening showed that the #34457 F1 mouse carries the targeted allele.

The aim of the project was to develop an AK005324 gene conditional knock-out mouse model. As presented hereinabove, the present inventor successfully amplified, cloned and sequenced the two arms of homology needed for the generation of the AK005324 targeting vector. The present inventor also succeeded in constructing the targeting and positive control vectors, following state of the art methodologies and according to the initial strategy. The present inventor also established and validated PCR and Southern blot screening strategies.

8 ES cell clones were identified, namely #4A3, #5A5, #3B7, #1A11, #4A2, #1B9, #2A8, and #3B4, fully validated for both 5' and 3' end targeted events. Based on morphological aspect and growth rate, the ES cell clones #3B4, #3B7, #4A3 and #5A5 were selected for blastocyst injections and led to the generation of 8 males chimeras displaying chimerism rate ranging from 40% to 98% were obtained.

As presented here, four chimeras were further bred to the F1 generation as follows: the male chimera generated from the ES clone #3B4 (displaying 60% chimerism) was mated with two WT C57Bl/6J females and the male chimera generated from the ES clone #3B7 (displaying 70% chimerism) was mated with two WT C57Bl/6J females. The two male chimeras generated from the ES clone #5A5 (displaying 95% and 98% chimerism) were mated with two WT C57Bl/6J females. The targeted allele was detected using PCR in one male F1 mouse (#34457), demonstrating germ line transmission of the 70% chimera generated from the ES cell clone #3B7.

Example 11

Breeding to F1 Generation with Wild-Type Mice and Confirmation of the Germline Transmission of the Targeted Allele Five agouti animals were obtained deriving from the breeding of the male chimeras (clone #3B7) with wild-type females, thus demonstrating germline transmission. The animals were further genotyped by PCR and Southern blot.

PCR Screening of the F1 Generation

DNA was prepared from a tail biopsy, taken from the resulting agouti pups and was PCR genotyped according to the genotyping protocol established in the previous subproject. Heterozygous F1 mice should yield an amplification product of 2.0 kb using the primer pair GW781/GX2589, detecting the targeted AK005324 allele. A representative example of the genotyping PCR results is illustrated in FIGS. 35A-B.

As presented in FIGS. 35A-B, the 5' PCR genotyping indicated that among the 5 tested agouti F1 animals born, one animal (#34457) carried the targeted allele (see FIG. 35 lane 1). This result showed that the chimeras derived from the ES cell line #3B7 were able to transmit the mutation to the F1 generation successfully.

Example 12

Southern Blot Validation of Heterozygous F1 Mice for the AK005324 Deletion

The single identified heterozygous F1 mouse identified by PCR was further verified by Southern blot analysis. For confirmation of 3' targeting, the blotted genomic NsiI digestion was tested with the external 3' probe 3E-R. Wild-type genomic DNA digested by NsiI allowed the detection of a 9.5 kb fragment, while recombined genomic DNA was expected to yield an 8.5 kb hybridization signal using the 3' probe.

As presented in FIGS. 36A-B, the Southern blot analysis showed that among the heterozygous F1 animals, the male #34457 was positive for the targeted AK005324 allele in accordance to the PCR result.

In conclusion the results of the PCR and Southern blot screenings have identified one male heterozygous F1 mouse (#34457).

Example 13

Breeding of Chimeras with Flp Deleter Mice and Generation of Neo-Deleted Heterozygous Foxed Mice The 70% chimeric male derived from cell clones #3B7 was mated with two C57BL/6J Flp deleter females (health status SOPF—Specific and Opportunist Pathogen Free) to allow the excision of the neomycin selection cassette.

The results of chimera breeding are shown in Table 17 below.

TABLE 17

Reporting results of chimera breeding with Flp deleter mice

| Parental chimeras | No. of pups born | Date of birth | Still born | No. of agouti pups | Tail biopsy No. |
|---|---|---|---|---|---|
| 70% male chimera (#3B7) | 3 | 23 Apr. 2006 | 0 | 3 | 35367-35369 |
| | 7 | 26 Apr. 2006 | 0 | 7 | 35370-35376 |

Example 14

PCR Genotyping of the F1 Generation Bred with Flp Deleter Mice

DNA was prepared from a tail biopsy, taken from the resulting agouti pups and was genotyped by two different PCR strategies:
1. Flp-excision PCR that was designed for the detection of the Flp-mediated excision of the FRT flanked neomycin cassette within the targeted AK005324 allele. This PCR yielded an amplification product of different size depending on the template used: wild-type, targeted or Flp-excised allele.
2. 3' screening PCR that was already used for detection of homologous recombination event in ES cells. This PCR strategy detected the non-excised, targeted AK005324 allele carrying the exon 3 flanked by LoxP-FRT-neo-FRT cassette and the distal LoxP site.

PCR Screening for the Detection of the Flp-Mediated Excision Event

This PCR was performed using a forward primer GX2595 hybridizing upstream of the targeting vector homology sequence and a reverse primer GX2596 hybridizing downstream of the neomycin selection cassette (see FIGS. 37A-B). Because of its localisation, this primer pair allowed the specific detection of the Flp-mediated excision event.

The excised allele should yield an amplification product of 646 bp using the above primer pair whereas the targeted (non-excised) allele should yield an amplification product of 3.3 kb. Since both primers hybridize to the wild-type non-targeted allele, a further amplification product of 468 bp should be obtained from all animals corresponding to the wild-type allele. A representative example of the genotyping PCR results is illustrated in FIGS. 37A-B.

PCR Screening for the Detection of Partial Excision

To further confirm the excision of the neomycin cassette in F1 heterozygotes mice, the PCR used above to detect the targeted allele was used. Animals scored positive for this PCR thus still have the neomycin cassette integrated within the AK005324 locus. A representative example of the genotyping PCR results is illustrated in FIGS. 38A-B.

Together, the results of these two screening PCRs showed that among the 10 tested agouti F1 animals born, 3 animals (#35367, #35368 and #35372) yielded amplification products corresponding to both the excised and non-excised allele in addition to the wild-type allele thus suggesting the neomycin cassette was still present. These mice thus carry an incomplete excision event, meaning that they are mosaics of excised and non-excised cell types.

Example 15

Southern Genotyping of the F1 Generation Bred with Flp Deleter Mice

The 10 heterozygous F1 mice were verified by Southern blot analysis, as described above in Example 3.

For confirmation of 3' targeting, the blotted genomic NsiI digestions were tested with the external 3' probe 3E-R. Wild-type genomic DNA digested by NsiI allowed the detection of a 9.5 kb fragment, while recombined genomic DNA was expected to yield an 8.5 kb hybridization signal using the 3' probe. The Flp-mediated neo-excised allele was expected to yield a 6.8 kb hybridization signal.

As presented in FIGS. 39A-B, the Southern blot analysis showed that among the 10 tested heterozygous F1 animals, the mice #35367, #35368 and #35372 were positive for both the AK005324 excised and non-excised allele, in addition to the wild-type allele. These mice thus carry an incomplete excision event, meaning that they are mosaics of excised and non-excised cell types.

The 3 incomplete excised heterozygotes were then bred with C57BL/6J wild-type mice in order to generate the excised conditional knock-out mice.

Example 16

Further Breeding of the Mosaic Excised F1 Mice

The identified mosaic animals were expected to carry germ cells showing the excised allele and germ cells showing the non-excised allele. By breeding further these animals with C57BL/6 wild-type mice, line of pure excised heterozygous mice could be obtained.

Two mosaic excised animals (#35367 and #35368) were each mated with two C57BL/6J wild-type mice (health status SOPF—Specific and Opportunist Pathogen Free). Table 18 below summarizes the results mice obtained from this breeding.

TABLE 18

Results of the further breeding of the mosaic excised mice

| Parental mouse | No. of pups born | Still born | Tail biopsy No. |
|---|---|---|---|
| #35367 | 0 | N/A | N/A |
| #35368 | 6 | 0 | 36173-36179 |

Example 17

Southern Validation of the Heterozygous Floxed F1 Mice

The 6 heterozygous excised F1 mice were verified by Southern blot analysis, as described above in Example 3.

As presented in FIGS. 40A-B, the Southern blot analysis showed that among the heterozygous F1 animals, the males #36175 and #36176 were positive for the AK005324 Flp-mediated neo-excised allele.

Example 18

Breeding with 129Sv Cre Deleter Mice

The 70% chimeric male (derived from cell clones #3B7), the F1 heterozygote mice #34457 and #35372 were each mated with two 129/Sv Cre deleter females (health status SOPF—Specific and Opportunist Pathogen Free) to allow the excision of the floxed region (exon 3) and thus the generation of the constitutive Knock-out allele.

Since Cre deleter mice on an 129/Sv genetic background were used for breeding with the chimera, coat colour genetics could no longer be used to establish the F1 mice derived from the targeted ES cells used in the blastocyst injection experiment. Consequently, all of the mice from these breeding were genotyped.

Table 19 below summarizes the results of chimeras breeding with 129Sv Cre deleter mice.

TABLE 19

Results of the Cre deleter breeding

| Parental mice | No. of pups born | Still born | Tail biopsy No. |
|---|---|---|---|
| #35457 heterozygous | 32 | 2 | #35444 to #35458 #35663 to #35722 #35979 to #35984 |
| 70% chimera (#3B7) | 5 | 0 | #36169 to #36172 |
| #35372 Partial neo-excised heterozygous | 15 | 0 | #35985 to #35992 #36290 to #36296 |

Example 19

PCR Genotyping of the F1 Generation Bred with Cre Deleter Mice

The F1 mice obtained were first screened using the two PCR strategies described above (data not shown).

Together, the results of these two screening PCRs showed that among the 9 F1 animals tested, two animals (#35450 and #36296) yielded amplification products corresponding to the recombined Cre-mediated excised allele and wild-type allele, suggesting these mice to be heterozygous for the constitutive Knock-out allele. Furthermore these animals showed no amplification product for a PCR specific for the targeted non-excised allele, thus confirming the excision event. Surprisingly, 6 animals (#35445, #35448, #35453, #35979, #35981 and #35982) could be identified which yielded amplification products corresponding to both the excised and non-excised alleles, with no detection of the wild-type allele.

Finally, one animal (#36295) yielded amplification products corresponding to the non-excised allele only, with no detection of both the excised and the wild-type allele.

Example 20

Southern Genotyping of the F1 Generation Bred with Cre Deleter Mice 9 out of the 9 F1 mice screened by PCR were further verified by Southern blot analysis. As presented in FIGS. 41A-B, the Southern blot analysis confirmed the PCR screening results:

The mouse #35450 was positive for the AK005324 Cre-mediated excised allele, in addition to the wild-type allele. This male mouse thus carried a complete Cre-mediated excision event, and was heterozygous for AK005324 constitutive Knock-out. The present inventor identified another female mouse (#36296) displaying the same genotype (data not shown). These results were consistent with the PCR screening results described above. Of note, the constitutive AK005324 Knock-out male #35450 died at the age of three weeks, with no noticeable phenotype.

Three animals (#35445, #35448, #35453) were positive for both the excised and non-excised alleles, with no detection of the wild-type allele. A similar genotype was confirmed using Southern in the 3 other mice #35979, #35981 and #35982 (data not shown).

Finally, one animal (#36295) was positive for the non-excised allele only, with the detection of neither the excised nor the wild-type allele (data not shown).

Example 21

Generation of Exon 3-Deleted Constitutive Knock-Out Heterozygous Mice

The constitutive AK005324 Knock-out female #36296 was bred with a wild-type C57BL/6J male in order to obtain additional constitutive AK005324 Knock-out animals. Table 20 below summarizes the results of this breeding.

TABLE 20

Reporting results of the further breeding

| Parental mice | No. of pups born | Still born | Tail biopsy No. |
|---|---|---|---|
| #36296 AK005324 constitutive Knock-out | | 0 | #37144 to #37149 |

Furthermore, the present inventor continued the breeding described above in Example 5 and in Table 4. The additional litters obtained are detailed in Table 21 below.

TABLE 21

Results of the further breeding with Cre deleter mice

| Parental mice | No. of pups born | Still born | Tail biopsy No. |
|---|---|---|---|
| #35372 Partial neo-excised heterozygous | 4 | 0 | #36548 to #36551 |

Finally, the present inventor bred the transmitting chimera with the second Cre deleter line (C57BL/6J genetic background). However, this breeding did not lead to any pregnancy.

Example 22

PCR Genotyping of the Constitutive AK005324 Knock-Out Mice

DNA was Prepared from Tail Biopsies, Taken from the Resulting Pups and was Genotyped by two Different PCR Strategies:

1. Flp-excision PCR that was designed for the detection of the Flp-mediated excision of the FRT flanked neomycin cassette within the targeted AK005324 allele. This PCR yielded an amplification product of different size depending on the template used: wild-type, targeted or Flp-excised allele.

2. 3' screening PCR that was already used for detection of homologous recombination event in ES cells. This PCR strategy detected the non-excised, targeted AK005324 allele carrying the exon 3 flanked by LoxP-FRT-neo-FRT cassette and the distal LoxP site.

Together, the results of these two screening PCRs showed that among 10 tested F1 animals born, three animals (#37145, #37148 and #37149) yielded amplification products corresponding to the recombined Cre-mediated excised allele and wild-type allele, suggesting these mice to be heterozygous for the constitutive Knock-out allele.

Furthermore these animals showed no amplification product for a PCR specific for the targeted non-excised allele, thus confirming the excision event. The other 7 animals were identified as wild-type, recombined or Flp-mediated neomycin excised.

Example 23

Southern Genotyping of the Constitutive AK005324 Knock-Out Mice

The 10 mice screened by PCR, together with our two 129Sv and C57BL/6J Cre deleter lines, were further genotyped using two different Southern blot analysis:
1. The NsiI, 3' external probe approach described hereinabove (see Examples 3 and 4 above.
2. A novel approach, based on AflII restriction, used in combination of the 3 external probes.

The results of these Southern blot analysis are shown in FIGS. 42A-B and FIGS. 43A-B.

As presented in FIGS. 43A-B, the Southern blot analysis confirmed the PCR screening results. The present inventor identified three mice (#37145, #37148 and #37149) positive for the AK005324 Cre-mediated excised allele, in addition to the wild-type allele. These animals thus carry a complete Cre-mediated excision event, and are heterozygous for constitutive AK005324 Knock-out alelle.

Example 24

Possible Explanation for the Results Obtained with the 129Sv Cre Deleter Line

As presented above in Example 5, three hypotheses were raised in order to explain the unexpected results obtained after breeding with the 129Sv Cre deleter line. These hypotheses are discussed below.

Hypothesis #1: Genotyping Technical Issue

In order to validate the Southern results based on NsiI restriction, the present inventor decided to genotype F1 mice using a different Southern strategy.

Due to the specific targeting strategy, a very limited number of restriction sites were available for this experiment. The inventor chose an AflII restriction but the difference in size of the detected restriction fragments was particularly small. Thus, the inventor struggled hard to achieve enough resolution of this Southern and this explains the low quality of the blot presented in FIG. 43B.

However, and as presented in FIG. 43B, the inventor observed the expected fragments (7.2 and 7.0 kb) for the female #36296, thus confirming its genotype as heterozygous for the constitutive Knock-out. This validated the Southern approach based on NsiI restriction.

Hypotheses #2 and #3: alteration of the AK005324 locus in the 129/Sv Cre deleter line.

Another explanation was that the present 129/Sv Cre deleter line was heterozygote at the AK005324 locus, possibly due to insertion of the Cre transgene or cryptic LoxP sites in the vicinity of the locus.

As presented in FIGS. 42A-B and FIGS. 43A-B, the inventor observed NsiI and AflII restriction fragment length polymorphisms using the 129Sv Cre deleter line. One extra fragment was in fact observed using the 3' probe after NsiI or AflII restriction. These fragments were observed in neither wild-type C57BL/6J mice nor C57BL/6J Cre deleter.

The unexpected results obtained after breeding with the 129Sv Cre deleter line could thus be due to this unexpected polymophism at the AK005324 in these deleter mice.

Germline Transmission—Generation of Mice Heterozygous for the Targeted Allele

After reaching sexual maturity, four highly chimeric males generated from the ES cell clone #3B7, 5A5, and #3B4 mated with wild-type C57BL/6J females to investigate whether the targeted ES cells have contributed to the germ layer.

The chimera breeding resulted in the generation of 1 agouti F1 pup, which was subsequently genotyped by PCR. The agouti F1 pup scored positive for the presence of the targeted AK005324 allele by PCR. This PCR positive animal was further validated by Southern blot analysis.

This result demonstrated ES cell germline transmission of the targeted AK005324 allele.

In Vivo Deletion of the Neomycin Selection Cassette—Generation of Floxed Heterozygous Mice Transmitting chimeras were then bred with C57BL/6J Flp recombinase expressing deleter mice to excise the neomycin selection cassette. This breeding resulted in the generation of 10 agouti F1 pups, which were subsequently genotyped by Southern blot analysis. Three partially excised agouti mice were identified which were then bred a generation further with C57BL/6J mice to obtain a pure line of floxed mice. Southern blot analysis revealed two animals heterozygous for the floxed AK005324 allele. The floxed AK005324 line, suitable for the generation of a conditional Knock-out line was thus available.

In Vivo Deletion of the Floxed Region—Generation of Heterozygotes Knock-Out Mice Transmitting chimeras, together with F1 heterozygote #34457 and Flp-mediated neo-exised heterozygote #35372 were bred with 129/Sv Cre recombinase expressing deleter mice to excise the floxed region. This breeding resulted in the generation of 52 F1 pups, among which 9 were subsequently genotyping by PCR and Southern analysis.

Two pups revealed the presence of the wild-type and excised alleles and were thus heterozygous for the constitutive AK005324 Knock-out allele. The inventor also observed unexpected results following the in vivo deletion of the floxed region and the generation of the heterozygote Knock-out mice.

Indeed, surprisingly, 6 pups revealed the presence of the recombined and excised alleles and one pup revealed the presence of the recombined allele only.

A restriction fragment length polymorphism at the AK005324 locus of the 129Sv Cre deleter line could explain the results obtained after Cre deleter breeding.

To obtain more heterozygous pups carrying the constitutive AK005324 allele, the inventor bred the identified constitutive Knock-out AK005324 female with a wild-type male and obtained three additional pups heterozygous for the constitutive AK005324 Knock-out allele.

The constitutive AK005324 Knock-out line was thus available.

Table 22 summarizes all the mice currently available.

TABLE 22

Available mice resulting from the breeding experiments

| Mouse | Sex | Genotype | Model |
|---|---|---|---|
| #34457 | M | F1 heterozygote, neo-present | |
| #35372 | F | Flp-mediated neo-excised (partial) | |
| #36175 | M | Flp-mediated neo-excised (total) | AK005324 conditional Knock-out |
| #36176 | M | Flp-mediated neo-excised (total) | AK005324 conditional Knock-out |
| #36296 | F | Cre-mediated ex3-excised (total) | AK005324 constitutive Knock-out |
| #37145 | M | Cre-mediated ex3-excised (total) | AK005324 constitutive Knock-out |
| #37148 | F | Cre-mediated ex3-excised (total) | AK005324 constitutive Knock-out |
| #37149 | F | Cre-mediated ex3-excised (total) | AK005324 constitutive Knock-out |

Example 25

Breeding of F1 Heterozygous and Generation of F2 Homozygous AK005324 Knock-Out Mice Breeding of the Heterozygous Mouse for Scale-Up of the Colony Three heterozygous female mice (#36296, #30798 and #31034) for the Cre-excised AK005324 recombined allele (Knock-out allele), generated as described above, were mated with wild-type C57BL/6J males (health status SOPF—Specific and Opportunist Pathogen Free) to generate extra heterozygous mice of both sexes for further breeding to homozygous generation.

Table 23 below summarizes the results of heterozygous generation breeding for scale up of the colony.

TABLE 23

Reporting results of female heterozygotes breeding with wild-type C57BL/6J males

| Parental female | clone ID | No. of pups born | Still born | Tail biopsy No. | ID number |
|---|---|---|---|---|---|
| #36296 | #3B7 | 1 | 0 | #34891 | 207 |
| #31304 | #3B7 | 3 | 0 | #35100 To #35102 | 208 to 210 |
| | | 5 | 0 | #37042 to #37046 | 251 to 255 |
| #30798 | #3B7 | 2 | 0 | #35912 to #35913 | 239 and 240 |
| | | 4 | 0 | #36887 to #36890 | 247 to 250 |

The biopsies recovered from the 15 pups derived from the interbreeding of F1 AK005324 Knock-out mice were tested using the PCR genotyping protocol described above. This PCR was performed using a forward primer GX2595 hybridizing upstream of the targeting vector homology sequence and a reverse primer GX2596 hybridizing downstream of the neomycin selection cassette (see FIG. 44). Because of its localization, this primer pair allowed the distinction between the Flp-mediated neomycin-deleted floxed allele, the Cre-mediated exon 3 deleted allele and the wild-type allele.

The conditional Knock-out allele (or floxed allele) should yield an amplification product of 646 pb, the constitutive knock-out allele should yield an amplification product of 232 pb whereas the wild-type allele should yield an amplification product of 468 pb.

PCR genotyping showed that among the 15 animals tested, 4 male mice (#35100, #36887, #37043 and #37045) and 3 female mice (#35913, #3688 and #37046) yielded amplification products corresponding to the recombined Cre-mediated excised allele and wild-type allele, suggesting these mice to be heterozygous for the constitutive Knock-out allele (data not shown).

Four positive PCR pups (mice #35100, #36887, #35913 and #3688) for the Cre-excised allele were further analyzed by Southern blot, in order to confirm their genotype. The Southern blot validating the 3' end homologous recombination was used for identification of the different AK005324 alleles.

The Southern blot analysis (FIGS. 45A-B) shows that the 4 tested animals (#35100, #36887, #35913 and #3688) carried the wild-type and Cre-mediated excised alleles meaning that they are heterozygous AK005324 knock-out mice.

In conclusion, the results of the PCR and Southern blot screenings allowed the characterization of 4 extra AK005324 Knock-out heterozygous mice (mice #35100, #36887, #35913 and #3688).

Breeding to the F2 Homozygous Generation

One F1 heterozygous male was mated with two F1 heterozygous females to generate the F2 homozygous generation. 11 pups were obtained and genotyped.

Table 24 below summarizes the results of F2 breeding.

TABLE 24

Reporting results of heterozygous mice interbreeding.

| Parental F1 heterozygous | N° of pups born | Still born | ID number | Tail biopsy N°. |
|---|---|---|---|---|
| Male #35100 | 11 | 0 | 281 | 14281 |
| Females #31034 | | | 282 | 14282 |
| #35913 | | | 283 | 14283 |
| | | | 284 | 14284 |
| | | | 285 | 14285 |
| | | | 286 | 14286 |
| | | | 287 | 14287 |
| | | | 288 | 14288 |
| | | | 289 | 14289 |
| | | | 290 | 14290 |
| | | | 291 | 14291 |
| | | | 292 | 14292 |
| | | | 293 | 14293 |
| | | | 294 | 14294 |
| | | | 295 | 14295 |

PCR Genotyping of the F2 Generation

DNA was prepared from a tail biopsy, taken from the resulting pups and was genotyped according to the protocol previously described.

Homozygous mice should yield a single amplification product of 0.2 kb using the primer pair GX2995/GX2995, detecting the Knock-out AK005324 allele. Heterozygous F2 mice should yield two amplification products of 0.5 kb and 0.2 kb corresponding to both the wild-type and to the Knock-out AK005324 alleles, respectively.

A representative example of the genotyping PCR results is illustrated in FIGS. 46A-B.

The initial PCR genotyping indicated that among the 11 tested F2 animals, 3 male mice (#14281, #14283 and #14286) yielded only the Knock-out AK005324 allele PCR amplification products of 0.2 kb suggesting that these mice were homozygous for the Cre-excised AK005324 allele.

Southern Blot Validation of Knock-Out AK005324 Homozygous Mice

F2 mice, identified by PCR as homozygous, were further verified by Southern blot analysis according to the protocol previously described.

F2 homozygous mice should yield only one NsiI fragment at 6.4 kb (see FIG. 47A).

The result of the Southern blot analysis is shown in FIG. 46A-B. The Southern blot analysis showed that the three homozygous F2 animals tested (males #14281, #14283 and #14286) displayed the expected signal corresponding to the Knock-out AK005324 allele and not the signal for wild-type allele in accordance to PCR results and confirming their homozygous status.

In conclusion the results of the PCR and Southern blot screenings have identified 3 male homozygous F2 mice AK005324.

Example 26

Breeding of F1 Heterozygous and Generation of F2 Homozygous Floxed AK005324

Breeding of the Heterozygous Mouse for Scale Up of the Colony

Two heterozygous male mice (#36176 and #30860), for the flp-excised AK005324 recombined allele (floxed allele), generated as described above, were mated with wild-type C57BL/6J males (health status SOPF—Specific and Opportunist Pathogen Free) to generate extra heterozygous mice of both sexes for further breeding to homozygous generation.

Table 25 below summarizes the results of heterozygous generation breeding for scale up of the colony.

TABLE 25

Reporting results of male heterozygotes breeding with wild-type C57BL/6J females.

| Parental male | Clone ID | N° of pups born | Still born | Tail biopsy N°. | ID number |
|---|---|---|---|---|---|
| #36176 | #3B7 | 11 | 0 | #35103 to #35113 | 211 to 221 |
|  |  | 6 | 0 | #36497 to #36502 | 241 to 246 |
| #30798 | #3B7 | 0 | — | — | — |

The biopsies recovered from the 17 pups derived from the breeding were tested using the PCR genotyping protocol previously described. This PCR was performed using a forward primer GX2595 hybridizing upstream of the targeting vector homology sequence and a reverse primer GX2596 hybridizing downstream of the neomycin selection cassette.

PCR genotyping showed that among the 17 animals tested, 3 males (#35105, #36499 and #36500) and 4 females (#35108, #35112, #36501 and #36502) yielded amplification products corresponding to the recombined Flp-mediated excised allele and wild-type allele, suggesting these mice to be heterozygous for the floxed allele (data not shown).

All positive PCR pups (mice #35105, #36499, #36500, #35108, #35112, #36501 and #36502) for the Flp-excised allele were further analyzed by Southern blot, in order to confirm their genotype. The Southern blot validating the 3' end homologous recombination was used for identification of the different AK005324 alleles. The strategy for Southern blot analysis was based on a NsiI digestion of the genomic DNA and hybridization with an internal 3' external probe, which led to the detection of the different specific DNA fragments.

The Southern blot analysis shows that the 7 tested animals (#35105, #36499, #36500, #35108, #35112, #36501 and #36502) carried the wild-type and Flp-mediated excised alleles meaning that they were heterozygous for the floxed AK005324 allele.

In conclusion, the results of the PCR and Southern blot screenings allowed the characterization of 7 extra AK005324 conditional Knock-out heterozygous mice ((#35105, #36499, #36500, #35108, #35112, #36501 and #36502).

Breeding to the F2 Homozygous Generation

Two F1 heterozygous males (#35105 and #36499) were mated with two F1 heterozygous females each (females #35108, #35112, #36501 and #36502) to generate the F2 homozygous generation. Eight pups were obtained and genotyped. The mating was stopped before male #36499 could generate litters.

Table 26 below summarizes the results of F2 breeding for male #35105.

TABLE 26

Reporting results of heterozygous mice interbreeding.

| Parental F1 heterozygous | No. of pups born | Still born | ID number | Tail biopsy No. |
|---|---|---|---|---|
| Male #35105 | 8 | 0 | 263 | #13676 |
| Females #35108 |  |  | 264 | #13677 |
| #35112 |  |  | 265 | #13678 |
|  |  |  | 266 | #13679 |
|  |  |  | 267 | #13680 |
|  |  |  | 268 | #13681 |
|  |  |  | 269 | #13682 |
|  |  |  | 270 | #13683 |

PCR Genotyping of the F2 Generation

DNA was prepared from a tail biopsy, taken from the resulting pups and was genotyped according to the protocol previously described.

Homozygous F2 mice should yield only one amplification product of 0.6 kb using the primer pair GX2995/GX2995, detecting the floxed AK005324 allele. Heterozygous F2 mice should yield two amplification products of 0.5 kb and 0.6 kb corresponding to both the wild-type and to the floxed AK005324 alleles, respectively.

A representative example of the genotyping PCR results is illustrated in FIGS. 48A-B.

The initial PCR genotyping indicated that among the 8 tested F2 animals, 2 males (mice #13677 and #13680) yielded only the Flp-excised AK005324 allele PCR amplification products of 0.6 kb suggesting that these mice were homozygous for the Flp-excised AK005324 allele.

Example 27

Southern Blot Validation of Knock-Out AK005324 Homozygous Mice

F2 mice, identified by PCR as homozygous, were further verified by Southern blot analysis according to the protocol previously described. For confirmation of the homozygous status, the NsiI digestion was tested with the external 3' probe. F2 homozygous mice should yield only one NsiI fragment at 6.4 kb (see FIG. 49A).

The result of the Southern blot analysis is shown in FIG. 49B.

The Southern blot analysis showed that the 2 homozygous F2 animals tested (mice #13677 and #13680) displayed the expected signal corresponding to the Flp-excised allele AK005324 allele and not the signal for wild-type allele in accordance to PCR results and confirming their homozygous status.

In conclusion, the results of the PCR and Southern blot screenings have identified 2 male homozygous (#13677 and #13680) F2 mice for the floxed AK005324 allele.

The aim of this project was to develop a mouse line carrying a constitutive Knock-out mutation of the AK005324 gene. A mouse line carrying a floxed allele suitable for the generation of a conditional AK005324 gene Knock-out was also developed.

For both constitutive and conditional lines, heterozygous mice obtained hereinabove were mated with wild type partners to scale up the colonies. The heterozygous mice were then interbred to generate the homozygous animals.

The genotyping strategy previously designed allowed a quick and unequivocal identification of the homozygous Knock-out (Cre-excised allele) and floxed (Flp-mediated excised allele) AK005324 gene mice within the F2 animals as follows:

An initial PCR pre-screening of the generated animals detected the Knock-out or floxed allele. The Southern blot analysis allowed further confirmation of the zygosity of the PCR positive animals.

Example 28

Generation of F2 Homozygous for the Foxed AK005324 Gene Mouse Model i.e. Constitutive Knock-Out Line The F2 breeding resulted in the generation of 11 pups, which were first genotyped by PCR and 3 pups scored positive for the presence of the Knock-out AK005324 allele only. PCR positive animals were further investigated by Southern blot analysis validating the homozygous status. Combining the results of the PCR and Southern blot screenings, the present inventor identified 3 male homozygous F2 mice (#14281, #14283 and #14286).

Example 29

Generation of F2 Homozygous for the Flp-Excised AK005324 Gene Mouse Model i.e. Conditional Knock-Out Line The F2 breeding resulted in the generation of 11 F2 pups, which were first genotyped by PCR and 3 F2 pups scored positive for the presence of the floxed AK005324 allele only. PCR positive animals were further investigated by Southern blot analysis validating the homozygous status. Combining the results of the PCR and Southern blot screenings, the present inventor identified 2 male homozygous F2 mice (#13677 and #13680).

Example 30

Significant Weight Change

Beginning between 5-10 days after birth, mice were weighed at intervals of 3-7 days. To keep track of individual mice, they were labeled with color pen markers before permanent labeling at about 20 days of age. MO-1 mice became obese at the age of approximately 2 to 4 months. The obese mice consumed abnormally large amounts of food. See FIGS. 50A-B and 51 for weight charts. Of note is the high weight found within the homozygous mice (HOMZ), as opposed to the other 2 groups, and the discrepancy between these and the weights of the heterozygotes (HETZ) and the wild.

Measured at their greatest differences, both male and female knock-outs were nearly 60% heavier than their age- and sex-matched controls. Total body fat mass and percentage body fat, as measured by MRI, were markedly elevated in MO-1$^{-/-}$ mice (FIG. 52). Percentage body fat was 2-fold greater in MO-1 KO mice compared to WT animals (24.4%+ 3.9 and 11.9%+1.8, respectively, n=10, p=0.002, FIG. 53).

Mice were phenotyped in metabolic cages, and while food consumption normalized to lean body mass was similar between MO-1 KO and wild-type mice a number of key differences were identified. Importantly, the increase in body weight related to food intake was 2-fold greater in MO-1 KO compared to wild-type mice (FIG. 53). In addition, locomotor activity, whole body oxygen consumption, heat production and rate of energy expenditure (fed and fasted) were all decreased in MO-1 KO mice (FIGS. 54A-B). Finally, and suggestive of differences in whole body fat oxidation differences, the respiratory quotient (RQ) was significantly increased in MO-1 KO compared to wild-type mice (0.96+ 0.01 compared to 0.93+0.01, n=10, p<0.05) (FIG. 54C). Furthermore, MO-1 KO mice were found to have fatty livers (data not presented).

Thus, loss of MO-1 in mice resulted in obesity, and its co-morbid features including diabetes, cardiac disease, and hypertension.

Example 31

Histopathological Examination

The pancreatic tissue of a MO-1 mouse according to the present invention (homozygote) and the pancreatic tissue of a normal mouse (KOR mouse) were fixed with 10% formalin, then embedded in paraffin, stained with hematoxylin-eosin (H-E) by an ordinary method, and then observed under a microscope (at 400× magnification).

The results showed that in the mouse according to the present invention, no damage or destruction of pancreatic islet (Langerhans islet) beta cells was observed although partial atrophy of the pancreatic tissue, in particular in pancreatic islet beta cells, was observed when compared to the normal mouse (data not shown).

Example 32

Neurological Disorders

MO-1-deficient mice also have certain neurological disorders. For instance, the mice are unusually very anxious. In order to detect anxiety-like behaviors, the present inventor has calculated anxiety index (distance made in periphery relative to total distance), immobility duration and immobility frequency.

A significant difference in the anxiety index was found using the "open field" and the "startle box" instruments [$F(2, 44)=14.078$, $p<0.0001$]. The hetrozygote showed a decreased anxiety index compared with the wild type ($p<0.0002$) and homo zygote ($p<0.0001$). The latter showed a tendency of increase compared with the wild type (FIG. 55).

A significant difference in immobility duration [$F(2,44) =5.184$, $p<0.01$] and frequency [$F(2,44)=39.98$, $p<0.0001$] were found. The homo zygote showed an increase in immobility duration compared with the hetrozygote ($p<0.003$), and a tendency in increase compared with the wild type (FIG. 56).

The hetrozygote showed the highest immobility frequency (wild type, p<0.001; homo zygote, p<0.0001), and the homo zygote showed the lowest (wild type, p<0.0001) one.

Example 33

Infertility

Transgenic mice homozygous for MO-1 mutation are infertile. This observation was clearly noted throughout many mating attempts with both Heterozygous and wild female mice, during more than 3 years. One cause of infertility in these mice is their inability to produce sperm (oligospermia).

Example 34

Cell Lines Derived from Transgenic Animals

Standard techniques known in the art are used to generate cell lines from the cells of the present transgenic mammals. For instance, primordial germ cell lines are established by techniques conventionally used for establishing ES cell lines.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A conditional knock-out non-human animal, wherein some cells of the non-human animal but not all the cells comprise a disrupted MO-1 nucleic acid sequence, wherein the disrupted MO-1 nucleic acid sequence encodes a disrupted MO-1 mRNA consisting of a knocked-out exon 3, and wherein the disruption results in an inability of the non-human animal to produce detectable levels of an MO-1 protein, as assayed by Western blot analysis, and further wherein the disruption results in at least one phenotype of the non-human animal selected from the group consisting of obesity, diabetes, cardiac disease, hypertension, fatty liver, anxiety, locomotion deficiency and decreased fertility.

2. The conditional knock-out non-human animal of claim 1, wherein said disrupted MO-1 nucleic acid sequence comprises an endogenous nucleic acid sequence encoding MO-1.

3. The conditional knock-out non-human animal of claim 1, wherein said disrupted MO-1 nucleic acid sequence has been introduced into said non-human animal by homologous recombination in an embryonic stem cell of said non-human animal.

4. The conditional knock-out non-human animal of claim 1, wherein said disrupted MO-1 nucleic acid sequence has been introduced into said non-human animal by a knock-out nucleic acid construct.

5. The conditional knock-out non-human animal of claim 4, wherein said knock-out nucleic acid construct comprises at least a portion of an MO-1 gene, wherein exon 3 of said MO-1 gene is flanked by a 5' loxP site and a 3' selectable marker cassette, wherein said selectable marker cassette is flanked by frt sites 3' and a 5' to said frt, and further wherein a loxP site is positioned 3' to the 3' frt site.

6. The conditional knock-out non-human animal of claim 1, comprising a recombinant MO-1 allele containing a neomycin gene and loxP sites flanking at least a portion of said exon 3 of said MO-1 gene.

7. The conditional knock-out non-human animal of claim 1, wherein said conditional disruption is induced by breeding the non-human animal with a non-human animal expressing a Cre recombinase under the control of a stage- or tissue-specific promoter.

8. The conditional knock-out non-human animal of claim 1, wherein said conditional disruption is induced by expressing in the non-human animal a transgene encoding a Cre recombinase under the control of a stage- or tissue-specific promoter.

9. The conditional knock-out non-human animal of claim 1, wherein said some cells of the non-human animal comprising said disrupted MO-1 nucleic acid sequence comprise liver cells.

10. The conditional knock-out non-human animal of claim 1, wherein said some cells of the non-human animal comprising said disrupted MO-1 nucleic acid sequence comprise pancreatic cells.

11. The conditional knock-out non-human animal of claim 1, wherein said some cells of the non-human animal comprising said disrupted MO-1 nucleic acid sequence comprise muscle cells.

12. The conditional knock-out non-human animal of claim 1, wherein said some cells of the non-human animal comprising said disrupted MO-1 nucleic acid sequence comprise kidney cells.

13. The conditional knock-out non-human animal of claim 1, wherein said some cells of the non-human animal are comprised in two or more tissues.

14. An isolated tissue of the conditional knock-out non-human animal of claim 1, wherein the tissue comprises said some cells which comprise a disrupted MO-1 nucleic acid sequence, wherein the disrupted MO-1 nucleic acid sequence encodes a disrupted MO-1 mRNA consisting of a knocked-out exon 3, and wherein the disruption results in an inability of the non-human animal to produce detectable levels of an MO-1 protein, as assayed by Western blot analysis.

15. A nucleic acid construct system comprising:
(i) a first nucleic acid construct which comprises an MO-1 nucleic acid sequence wherein the disrupted MO-1 nucleic acid sequence encodes a disrupted MO-1 mRNA consisting of a knocked-out exon 3, and a selectable marker both flanked by loxP sites;
(ii) a second nucleic acid construct which comprises a Cre recombinase under the control of a tissue specific promoter.

16. A method of generating a non-human animal with a targeted conditional disruption in an MO-1 gene, the method comprising:
(a) transfecting said first nucleic acid construct of claim 15 into a population of murine embryonic stem (ES) cells;
(b) selecting a transfected ES cell which expresses said selectable marker;
(c) introducing said transfected ES cell into an embryo of an ancestor of said non-human animal;
(d) allowing said embryo to develop to term to produce a chimeric non-human animal with a conditional knock-out construct in its germ line;
(e) breeding said chimeric non-human animal with a non-human animal expressing flippase to produce a heterozygous non-human animal which does not contain said selectable marker; and
(f) breeding said heterozygous non-human animal with a non-human animal expressing a Cre recombinase under the control of a stage- or tissue-specific promoter to produce the non-human animal with the targeted conditional disruption in the MO-1 gene.

17. The nucleic acid construct system of claim 15, wherein said first nucleic acid construct comprises a portion of an MO-1 gene, wherein exon 3 of said MO-1 gene is flanked by a 5' loxP site and a 3' selectable marker cassette, wherein said selectable marker cassette is flanked by frt sites 3' and a 5' to said frt, and further wherein a loxP site is positioned 3' to the 3' frt site.

18. The conditional knock-out non-human animal of claim 1, wherein the non-human animal is selected from the group consisting of a mouse, a rat, a rabbit, a hamster and a sheep.

19. The conditional knock-out non-human animal of claim 18, wherein said mouse comprises a C57BL/6J mouse.

20. A conditional knock-out non-human animal, wherein some cells of the non-human animal but not all the cells comprise a disrupted MO-1 nucleic acid sequence, wherein the disrupted MO-1 nucleic acid sequence encodes a disrupted MO-1 mRNA consisting of a knocked-out exon 3, and wherein the disruption results in an inability of the non-human animal to produce detectable levels of an MO-1 protein, as assayed by Western blot analysis, and further wherein the disruption and said inability to produce detectable levels of said MO-1 protein result in at least one phenotype of the non-human animal selected from the group consisting of obesity, diabetes, cardiac disease, hypertension, fatty liver, anxiety, locomotion deficiency and decreased fertility.

\* \* \* \* \*